United States Patent
Chen et al.

(10) Patent No.: US 11,253,509 B2
(45) Date of Patent: Feb. 22, 2022

(54) METHODS OF TREATMENT FOR CYSTIC FIBROSIS

(71) Applicant: Vertex Pharmaceuticals Incorporated, Boston, MA (US)

(72) Inventors: Weichao George Chen, San Diego, CA (US); Eric L. Haseltine, Melrose, MA (US); Samuel Moskowitz, Waban, MA (US); Sarah Robertson, Somerville, MA (US); David Waltz, Waban, MA (US)

(73) Assignee: Vertex Pharmaceuticals Incorporated, Boston, MA (US)

(*) Notice: Subject to any disclaimer, the term of this patent is extended or adjusted under 35 U.S.C. 154(b) by 0 days.

(21) Appl. No.: 16/620,265

(22) PCT Filed: Jun. 8, 2018

(86) PCT No.: PCT/US2018/036610
§ 371 (c)(1),
(2) Date: Dec. 6, 2019

(87) PCT Pub. No.: WO2018/227049
PCT Pub. Date: Dec. 13, 2018

(65) Prior Publication Data
US 2021/0113547 A1    Apr. 22, 2021

Related U.S. Application Data

(60) Provisional application No. 62/517,049, filed on Jun. 8, 2017, provisional application No. 62/533,381, filed (Continued)

(51) Int. Cl.
*A61K 31/47* (2006.01)
*A61P 11/00* (2006.01)
(Continued)

(52) U.S. Cl.
CPC ........ *A61K 31/47* (2013.01); *A61K 31/4045* (2013.01); *A61K 31/443* (2013.01); *A61K 31/4439* (2013.01); *A61P 11/00* (2018.01)

(58) Field of Classification Search
CPC .. A61K 31/47; A61K 31/4045; A61K 31/443; A61K 31/4439; A61K 31/454; A61P 11/00; A61P 11/12
(Continued)

(56) References Cited

U.S. PATENT DOCUMENTS

| 5,410,061 A | 4/1995 | Gilmore et al. |
| 6,441,004 B1 | 8/2002 | Faull et al. |

(Continued)

FOREIGN PATENT DOCUMENTS

| AU | 2013231151 A1 | 10/2013 |
| AU | 2013270464 A1 | 1/2014 |

(Continued)

OTHER PUBLICATIONS

Anilkumar, G.N. et al. (2011) "II. Novel HCV NS5B polymerase inhibitors: Discovery of indole C2 acyl sulfonamides" *Biogranic & Medicinal Chemistry Letters*, 22(1):713-717.
(Continued)

*Primary Examiner* — Taylor V Oh
(74) *Attorney, Agent, or Firm* — Finnegan, Henderson, Farabow, Garrett & Dunner, LLP

(57) ABSTRACT

Compound I of the formula (formula) A pharmaceutically acceptable salt of Compound I. Pharmaceutical compositions containing at least Compound I and methods of treating cystic fibrosis comprising administering at least Compound I. Pharmaceutical compositions containing a pharmaceutically acceptable salt of at least Compound I and methods of treating cystic fibrosis comprising administering a pharmaceutically acceptable salt of at least Compound I.

(Continued)

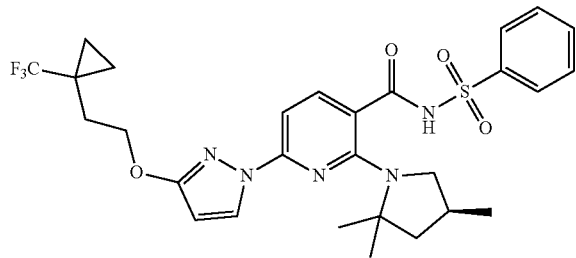

21 Claims, 10 Drawing Sheets

Related U.S. Application Data on Jul. 17, 2017, provisional application No. 62/562,044, filed on Sep. 22, 2017, provisional application No. 62/623,757, filed on Jan. 30, 2018, provisional application No. 62/633,021, filed on Feb. 20, 2018, provisional application No. 62/649,266, filed on Mar. 28, 2018.

(51) Int. Cl.
  *A61K 31/4045* (2006.01)
  *A61K 31/443* (2006.01)
  *A61K 31/4439* (2006.01)

(58) Field of Classification Search
  USPC .......................................................... 514/312
  See application file for complete search history.

(56) References Cited

U.S. PATENT DOCUMENTS

| | | | |
|---|---|---|---|
| 6,787,651 B2 | 9/2004 | Stolle et al. | |
| 6,949,572 B2 | 9/2005 | Bertinato et al. | |
| 6,979,692 B2 | 12/2005 | Bertinato et al. | |
| 7,368,573 B2 | 5/2008 | Bertinato et al. | |
| 8,058,299 B2 | 11/2011 | Bolin et al. | |
| 9,663,508 B2 | 5/2017 | Bregman et al. | |
| 9,782,408 B2 | 10/2017 | Miller et al. | |
| 9,981,910 B2 | 5/2018 | Altenbach et al. | |
| 10,118,916 B2 | 11/2018 | Altenbach et al. | |
| 10,131,670 B2 | 11/2018 | Strohbach et al. | |
| 10,138,227 B2 | 11/2018 | Altenbach et al. | |
| 10,208,053 B2 | 2/2019 | Strohbach et al. | |
| 10,258,624 B2 | 4/2019 | Miller et al. | |
| 10,570,115 B2 | 2/2020 | Alcacio et al. | |
| 10,654,829 B2 | 5/2020 | Dhamankar et al. | |
| 10,793,547 B2 | 10/2020 | Abela et al. | |
| 2002/0055631 A1 | 5/2002 | Augeri et al. | |
| 2002/0086887 A1 | 7/2002 | Augeri et al. | |
| 2004/0006237 A1 | 1/2004 | Dolitzky et al. | |
| 2005/0171185 A1 | 8/2005 | Yamasaki et al. | |
| 2005/0197376 A1 | 9/2005 | Kayakiri et al. | |
| 2007/0105833 A1 | 5/2007 | Ruah et al. | |
| 2010/0227888 A1 | 9/2010 | Hadida Ruah et al. | |
| 2011/0165118 A1 | 7/2011 | Chan et al. | |
| 2013/0072483 A1 | 3/2013 | Wenge et al. | |
| 2013/0267493 A1 | 10/2013 | Bhattacharya et al. | |
| 2013/0317000 A1 | 11/2013 | Chowdhury et al. | |
| 2013/0317001 A1 | 11/2013 | Andrez et al. | |
| 2014/0080825 A1 | 3/2014 | Hadida-Ruah et al. | |
| 2014/0296200 A1 | 10/2014 | Brown et al. | |
| 2015/0320736 A1 | 11/2015 | Phenix et al. | |
| 2015/0322002 A1 | 11/2015 | Dehnhardt et al. | |
| 2016/0095858 A1* | 4/2016 | Miller .................. | A61K 31/497 514/253.09 |
| 2018/0099932 A1 | 4/2018 | Altenbach et al. | |
| 2018/0141954 A1 | 5/2018 | Strohbach et al. | |
| 2018/0170938 A1 | 6/2018 | Strohbach et al. | |
| 2018/0244611 A1 | 8/2018 | Altenbach et al. | |
| 2018/0244640 A1 | 8/2018 | Altenbach et al. | |
| 2019/0055220 A1 | 2/2019 | Bear et al. | |
| 2019/0077784 A1 | 3/2019 | Altenbach et al. | |
| 2019/0153000 A1 | 5/2019 | Munoz et al. | |
| 2019/0240197 A1 | 8/2019 | Chu et al. | |
| 2019/0269683 A1 | 9/2019 | Miller et al. | |
| 2020/0138798 A1 | 5/2020 | Chen et al. | |
| 2020/0171015 A1 | 6/2020 | Haseltine et al. | |
| 2020/0369608 A1 | 11/2020 | Angell et al. | |
| 2020/0392109 A1 | 12/2020 | Dhamankar et al. | |
| 2021/0032272 A1 | 2/2021 | Abela et al. | |
| 2021/0047295 A1 | 2/2021 | Abela et al. | |
| 2021/0052584 A1 | 2/2021 | Miller et al. | |
| 2021/0069174 A1 | 3/2021 | Chu et al. | |
| 2021/0113547 A1 | 4/2021 | Chen et al. | |
| 2021/0139514 A1 | 5/2021 | Abela et al. | |

FOREIGN PATENT DOCUMENTS

| | | |
|---|---|---|
| CA | 2145473 A1 | 9/1995 |
| EP | 0 194 599 A2 | 9/1986 |
| EP | 0 673 930 A1 | 9/1995 |
| EP | 1 318 978 B1 | 2/2006 |
| JP | 10-114654 A | 5/1998 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/31226 A1 | 7/1998 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A1 | 10/2004 |
| WO | WO 2004/111014 A1 | 12/2004 |
| WO | WO 2005/049018 A1 | 6/2005 |
| WO | WO 2005/054191 A1 | 6/2005 |
| WO | WO 2005/070006 A2 | 8/2005 |
| WO | WO 2005/075435 A1 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/002421 A2 | 1/2006 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |
| WO | WO 2007/019397 A2 | 2/2007 |
| WO | WO 2007/021982 A2 | 2/2007 |

(56) References Cited

FOREIGN PATENT DOCUMENTS

| | | |
|---|---|---|
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/113327 A2 | 10/2007 |
| WO | WO 2007/117715 A2 | 10/2007 |
| WO | WO 2007/134279 A2 | 11/2007 |
| WO | WO 2008/005457 A2 | 1/2008 |
| WO | WO 2008/100867 A2 | 8/2008 |
| WO | WO 2008/127399 A2 | 10/2008 |
| WO | WO 2008/141385 A1 | 11/2008 |
| WO | WO 2009/006315 A1 | 1/2009 |
| WO | WO 2009/027730 A1 | 3/2009 |
| WO | WO 2009/032116 A1 | 3/2009 |
| WO | WO 2009/038683 A2 | 3/2009 |
| WO | WO 2009/064848 A1 | 5/2009 |
| WO | WO 2009/071947 A2 | 6/2009 |
| WO | WO 2009/073757 A1 | 6/2009 |
| WO | WO 2009/076142 A2 | 6/2009 |
| WO | WO 2009/127822 A2 | 10/2009 |
| WO | WO 2009/138758 A2 | 11/2009 |
| WO | WO 2010/003444 A2 | 1/2010 |
| WO | WO 2010/007116 A2 | 1/2010 |
| WO | WO 2010/019239 A2 | 2/2010 |
| WO | WO 2010/022307 A2 | 2/2010 |
| WO | WO 2010/025295 A2 | 3/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/065824 A2 | 6/2010 |
| WO | WO 2010/078103 A1 | 7/2010 |
| WO | WO 2010/083441 A2 | 7/2010 |
| WO | WO 2010/102758 A2 | 9/2010 |
| WO | WO 2010/108155 A1 | 9/2010 |
| WO | WO 2010/108162 A1 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/019413 A1 | 2/2011 |
| WO | WO 2011/068560 A1 | 6/2011 |
| WO | WO 2011/072241 A1 | 6/2011 |
| WO | WO 2011/102514 A1 | 8/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/128251 A1 | 10/2011 |
| WO | WO 2011/133751 A2 | 10/2011 |
| WO | WO 2011/133951 A1 | 10/2011 |
| WO | WO 2011/150016 A1 | 12/2011 |
| WO | WO 2012/027247 A2 | 3/2012 |
| WO | WO 2012/027731 A2 | 3/2012 |
| WO | WO 2012/052540 A1 | 4/2012 |
| WO | WO 2012/087938 A1 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A1 | 10/2012 |
| WO | WO 2012/166415 A1 | 12/2012 |
| WO | WO 2012/170061 A1 | 12/2012 |
| WO | WO 2013/033068 A1 | 3/2013 |
| WO | WO 2013/037955 A1 | 3/2013 |
| WO | WO 2013/038373 A1 | 3/2013 |
| WO | WO 2013/041602 A1 | 3/2013 |
| WO | WO 2013/070961 A1 | 5/2013 |
| WO | WO 2013/082102 A1 | 6/2013 |
| WO | WO 2013/112804 A1 | 8/2013 |
| WO | WO 2013/118805 A1 | 8/2013 |
| WO | WO 2013/130669 A1 | 9/2013 |
| WO | WO 2013/158121 A1 | 10/2013 |
| WO | WO 2013/177224 A1 | 11/2013 |
| WO | WO 2013/185112 A1 | 12/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 A2 | 3/2014 |
| WO | WO 2014/071122 A1 | 5/2014 |
| WO | WO 2014/071247 A1 | 5/2014 |
| WO | WO 2014/071378 A1 | 5/2014 |
| WO | WO 2014/086723 A1 | 6/2014 |
| WO | WO 2014/086739 A1 | 6/2014 |
| WO | WO 2014/086751 A1 | 6/2014 |
| WO | WO 2014/096388 A2 | 6/2014 |
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/105484 A1 | 6/2016 |
| WO | WO 2016/105485 A2 | 6/2016 |
| WO | WO 2016/128529 A1 | 8/2016 |
| WO | WO 2016/160945 A1 | 10/2016 |
| WO | WO 2017/053455 A1 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/113089 A1 | 6/2019 |
| WO | WO 2019/113476 A1 | 6/2019 |
| WO | WO 2019/152940 A1 | 8/2019 |
| WO | WO 2019/026075 A1 | 10/2019 |
| WO | WO 2019/191620 A1 | 10/2019 |
| WO | WO 2019/195739 A1 | 10/2019 |
| WO | WO 2019/200246 A1 | 10/2019 |
| WO | WO 2020/214921 A1 | 10/2020 |
| WO | WO 2020/242935 A1 | 12/2020 |

OTHER PUBLICATIONS

Anonymous: "Vertex Announces Positive Phase 1 & Phase 2 Data from Three Different Triple Combination Regimens in People with Cystic Fibrosis Who Have One F508del Mutation and One Minimal Function Mutation (F508del/Min): Vertex Pharmaceuticals", Jul. 18, 2017 (Jul. 18, 2017), XP055574958, Retrieved from the Internet: URL:https://investors.vrtx.com/news-releases/news-release-details/vertex-announces-positive-phase-1-phase-2-data-three-different [retrieved on Mar. 27, 2019].

Atzrodt J, Derdau V, Fey T, Zimmermann J. "The Renaissance of H/D Exchange" Angew. Chem. Int. Ed. 2007: 46, 7744-7765.

(56) References Cited

OTHER PUBLICATIONS

Atzrodt J, Derdau V, Kerr W, Reid M. "C—H functionalization for hydrogen isotope exchange" Angew. Chem. Int. Ed. 2018: 57, 3022-3047.
Belikov, V.G., (2007) *Farmatsevticheskaya khimiya* (*Pharmaceutical Chemistry*), Moscow: MEDpress-inform, pp. 27-29.
Borhade, S.R. et al. (2013) "Synthesis of Novel Aryl and Heteroaryl Acyl Sulfonimidamides via Pd-Catalyzed Carbonylation Using a Nongaseous Precursor" *Organic Lett*, 15(5):1056-1059.
Braman, V.; Liu, J. F.; Harbeson, S.; Uttamsingh, V.; Bridson, G.; Wu, L.; Shipley, J. E. "Preliminary Clinical Outcomes for CTP-354, a Novel Subtype-Selective GABA(A) Modulator" Presented at the American Neurological Association (ANA) 2014 Annual Meeting, Baltimore, MD, Oct. 12-14, 2014.
Byrn, S. et al. (1995) "Pharmaceutical solids: A strategic approach to regulatory considerations," (12): 945-954.
Caira, M. R. (1998) "Crystalline Polymorphism of Organic Compounds," *Topics in Current Chemistry*, 163-208.
Cargnin S, Serafini M, Pirali T. "A primer of deuterium in drug design" Future Med. Chem. 2019; 11(16): 2039-2042.
Chen, Y. (Jan. 26, 2016) "N-Monoacylation of Sulfonimidamides" *Synthesis*, 48(7):1019-1028.
Czeskis B, Elmore, CS, Haight A, Hesk D, Maxwell BD, Miller SA, Raglione T, Schildknegt K, Traverse JF, Wang P. "Deuterated active pharmaceutical ingredients: A science-based proposal for synthesis, analysis, and control. Part 1: Framing the problem" J. Label. Compd. Radiopharm. 2019, 62: 690-694. DOI: 10.1002/jlcr.3743.
Dao HT, Li C, Michaudel Q, Maxwell BD, Baran PS. J. Am. Chem. Soc. 2015; 137, 8046-8049.
Database Caplus, Accession No. 1965:51408. Abstract of French Patent No. FR M2868, filed Nov. 23, 1964, by Roussel-UCLAF [online]. Retrieved Jan. 6, 2017 (1 page).
Database Caplus, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).
Database Pubchem, CID: 20050716. Compound Summary, 1-[2-[[2-[(2-Amino-3-methylbutanoyl)amino]-3-methylpentanoyl]amino]-3-phenylpropanoyl]pyrrolidine-2-carboxylic acid. NIH, U.S. National Library of Medicine, National Center for Biotechnology Information; Modify Date: Nov. 30, 2019. [online]. Retrieved from https://pubchem.ncbi.nlm.nih.gov/compound/20050716, on Dec. 3, 2019 (7 pages).
Database Pubchem, CID: 20091118. Compound Summary, [4-(5-Hexylpyrimidin-2-yl)phenyl] 2-methoxypropanoate. NIH, U.S. National Library of Medicine, National Center for Biotechnology Information; Modify Date: Nov. 30, 2019. [online]. Retrieved from https://pubchem.ncbi.nlm.nih.gov/compound/20091118, on Dec. 3, 2019 (9 pages).
Database Pubchem, CID: 20120819. Compound Summary, 4-(Cyclopentyloxy)-3-fluorobenzene-1-sulfonyl chloride. NIH, U.S. National Library of Medicine, National Center for Biotechnology Information; Modify Date: Nov. 30, 2019. [online]. Retrieved from https://pubchem.ncbi.nlm.nih.gov/compound/20120819, on Dec. 3, 2019 (8 pages).
Database Pubchem, CID: 2545578. Compound Summary, 75339296. NIH, U.S. National Library of Medicine, National Center for Biotechnology Information; Modify Date: Jan. 16, 2016. [online]. Retieved from https://pubchem.ncbi.nlm.nih.gov/compound/2545578, on Jan. 22, 2016 (9 pages).
Database Pubchem, CID: 44419393. Compound Summary, *CHEMBL374189*. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).
Database Pubchem, CID: 49774135. Compound Summary, *SCHEMBL13395127*. NIH, U.S. National Library of Medicine, National Center for Biotechnology Information; Modify Date: Jan. 16, 2016 [online]. Retrieved from https://pubchem.ncbi.nlm.nih.gov/compound/49774135, on Jan. 22, 2016 (10 pages).
Database Pubchem, CID: 58132855. Compound Summary, *SCHEMBL831192*. NIH, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).
Dorwald, F. A. (2006) "Side Reactions in Organic Synthesis" Wiley: VCH, Weinheim p. IX of Preface p. 1-15.
Gant TG. "Using Deuterium in Drug Discovery: Leaving the Label in the Drug" J Med. Chem. 2014; 57(9): 3595-3611.
Garg, V. et al. "Pharmacokinetic and Drug-Drug Interaction Profiles of the Combination of Tezacaftor/Ivacaftor", Clinical and Translational Science—CTS, vol. 12, No. 3, Jan. 29, 2019 (Jan. 29, 2019), pp. 267-275, XP055719490, US ISSN: 1752-8054, DOI: 10.1111/cts.12610.
Halford B. "The deuterium switcheroo" Chemical & Engineering News 2016; 94(27), 32-36.
Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.
International Patent Application No. PCT/US2015/54316: International Search Report and Written Opinion, dated Feb. 5, 2016 (11 pages).
International Patent Application No. PCT/US2017/025381: International Search Report and Written Opinion, dated Jun. 6, 2017 (11 pages).
International Patent Application No. PCT/US2017/054611: International Search Report and Written Opinion, dated Jan. 3, 2018 (10 pages).
International Patent Application No. PCT/US2017/065425: International Search Report and Written Opinion, dated Feb. 27, 2018 (10 pages).
International Patent Application No. PCT/US2018/036610: International Search Report and Written Opinion, dated Sep. 19, 2018 (9 pages).
International Patent Application No. PCT/US2018/040427: International Search Report and Written Opinion, dated Oct. 9, 2018 (15 pages).
International Patent Application No. PCT/US2018/042415: International Search Report and Written Opinion, dated Oct. 31, 2018 (12 pages).
International Patent Application No. PCT/US2018/042486: International Search Report and Written Opinion, dated Nov. 7, 2018 (13 pages).
International Patent Application No. PCT/US2018/044963: International Search Report and Written Opinion, dated Sep. 25, 2018 (15 pages).
International Patent Application No. PCT/US2018/056772: International Search Report and Written Opinion, dated Jan. 29, 2019 (13 pages).
International Patent Application No. PCT/US2018/063871: International Search Report and Written Opinion, dated Feb. 25, 2019 (16 pages).
International Patent Application No. PCT/US2019/016537: International Search Report and Written Opinion, dated Apr. 23, 2019 (13 pages).
International Patent Application No. PCT/US2018/064522: International Search Report and Written Opinion, dated Jun. 25, 2019 (21 pages).
International Patent Application No. PCT/US2019/018042: International Search Report and Written Opinion, dated Apr. 17, 2019 (10 pages).
International Patent Application No. PCT/US2019/024890: International Search Report and Written Opinion, dated Jun. 17, 2019 (13 pages).
International Patent Application No. PCT/US2019/026075: International Search Report and Written Opinion, dated Jun. 17, 2019 (13 pages).
International Patent Application No. PCT/US2019/027202: International Search Report and Written Opinion, dated Jun. 17, 2019 (10 pages).

(56) References Cited

OTHER PUBLICATIONS

International Patent Application No. PCT/US2020/028699: International Search Report and Written Opinion, dated Jul. 20, 2020 (9 pages).
International Patent Application No. PCT/US2020/034199: International Search Report and Written Opinion, dated Aug. 11, 2020 (15 pages).
Jain, B.C. et al. (1947) "Studies in Sulphanilamides. Part XIII. Reaction With Dicarboxylic Acids. Some New N1- and N4-Acyl and Heterocyclic Derivatives" *Journal of the Indian Chemical Society*, 24:173-176.
Kettle, J.G. et al. (2004) "N-Benzylindole-2-carboxylic acids: potent functional antagonists of the CCR2b chemokine receptor" *Bioorganic & Medicinal Chemistry Letters*, 14(2): 405-408.
Kieltsch, I. et al. LAUREATES: Awards and Honors SCS Fall Meeting 2007 260 Recent Advances in Electrophilic CF 3-Transfer Using Hypervalent Iodine(III) Reagents 11, A Chimia Chimia Schweizerische Chemische Gesellschaft ISSN, vol. 62, No. 62, Jan. 1, 2008 (Jan. 1, 2008), pp. 260-263, XP055591571, DOI: 10.2533/chimia.2008.260.
Lai, J.T. et al. (1980) "Rearrangement of 2,2,6,6-tetramethyl-4-piperidone in phase-transfer catalyzed reactions," *Journal of Organic Chemistry*, 45(8):1513-1514.
Liu, J. F. et al. "CTP-354: A Novel Deuterated Subtype-Selective GABA(A) Modulator for Treatment of Neuropathic Pain, Spasticity and Anxiety Disorders" Presented at the American College of Neuropsychopharmacology (ACNP) 51st Annual Meeting, Hollywood, FL, Dec. 2-6, 2012.
Matter, H. et al. (2002) "Design and Quantitative Structure-Activity Relationship of 3-Amidinobenzyl-1H-indole-2-carboxamides as Potent, Nonchiral, and Selective Inhibitors of Blood Coagulation Factor Xa" *Journal of Medicinal Chemistry*, 45(13):2749-2769.
Maxwell BD, Tran SB, Lago M, Li J, and Bonacorsi Jr SJ. "The syntheses of [14C]BMS-823778 for use in a human ADME clinical study and of [13CD313CD2]BMT-094817, a stable-isotope labeled standard of a newly detected human metabolite" J. Label. Compd. Radiopharm. 2016; 59, 255-259.
Montemayor, Kristina et al. "Unmasking catamenial hemoptysis in the era of CFTR modulator therapy", Journal of Cystic Fibrosis, Elsevier, NL, vol. 19, No. 4, Jan. 24, 2020 (Jan. 24, 2020), XP086202454, ISSN: 1569-1993, DOI: 10.1016/J.JCF.2020.01.005 [retrieved on Jan. 24, 2020].
Norman, P. (2014) "Novel picolinamide-based cystic fibrosis transmembrane regulator modulators: evaluation of WO2013038373, WO2013038376, WO2013038381, WO2013038386, and WO2013038390," *Expert Opinion on Therapeutic Patents*, 24(7):829-837.
Notice of Allowance and Fee(s) Due for U.S. Appl. No. 15/836,627, dated Jun. 18, 2020.
Notman, N. (2016) "2Heavy drugs gaining momentum" [online] Retrieved from the internet: https://www.chemistryworld.com/features/2heavy-drugs-gaining-momentum/1010186.article, on Oct. 7, 2019.
Passarella, D. et al. (2001) "Cyclodimerization of indol-2-ylacetylenes. An example of intermolecular enyne-alkyne cycloaddition" *Journal of the Chemical Society, Perkin Transactions 1*, 127-129.
Pirali T, Serafini M, Cargnin S, Genazzani AA. "Applications of Deuterium in Medicinal Chemistry" J Med. Chem. 2019; 62(11): 5276-5297.
Qun, C. et al. "Synthesis of 3,3,3-trifluoro-2,2-dimethylpropionic acid", Huaxue Shiji—Chemical Reagents, Beijing : Huaxue Huaxue Shiji Keji Qingbao Zhongxinzhan, CN, vol. 38, No. 4, Jan. 1, 2016 (Jan. 1, 2016), pp. 386-388, XP009513488, ISSN: 0258-3283, DOI: 10.13822/J.CNKI.HXSJ.2016.04.026.
Rosebraugh, C.J. (2015) "Highlights of Prescribing Information for Orkambi," [online] Retrieved from the Internet: https://www.accessdata.fda.gov/drugsatfda_docs/label/2015/206038Orig1s000lbl.pdf, on Aug. 24, 2017.

Schmidt C. "First deuterated drug approved" Nat. Biotechnol. 2017, 35, 493-494.
Silverman, R. (2004) The Organic Chemistry of Drug Design and Drug Action, Elsevier, pp. 29-32.
Soloducho, J. (1989) "Synthesis of Some Pyrido [2,3-c][1,2,6]triazinone Derivatives" *Journal für Pracktische Chemie*, 331(3):503-506.
Tsong-Long H. et al. "Synthesis and pharmacological characterization of 2-aminobenzaldehyde oxime analogs as dual inhibitors of neutrophil elastase and proteinase 3", Bioorganic & Medicinal Chemistry, vol. 23, No. 5, Jan. 16, 2015, pp. 1123-1134, XP029199003.
U.S. Appl. No. 16/635,346, filed Jan. 30, 2020, by Angell et al.
U.S. Appl. No. 16/836,155, filed Mar. 31, 2020, by Miller et al.
Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.
Venkatesh, S. et al. (2000) "Role of the development scientist in compound lead selection and optimization" *J. Pharm. Sci.* 89(2), 145-154.
Verado, G. et al. (1999) "Reductive One Batch Synthesis of N-Substituted Pyrrolidines from Primary Amines and 2,5-Dimethoxytetrahydrofuran" *Synthesis*, (1):74-79.
Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.
Vertex Pharmaceuticals, Inc. (Jul. 18, 2017) "Vertex Announces Positive Phase 1 & Phase 2 Data from Three Different Triple Combination Regimens in People with Cystic Fibrosis Who Have One F508del Mutation and One Minimal Function Mutation (F508del/Min)", Retrieved from the Internet: URL: http://investors.vrtx.com/news-releases/news-release-details/vertex/announces-positive-phase-1-phase-2-data-three-different [retrieved on Mar. 27, 2019].
Vertex Pharmaceuticals, Inc. (Nov. 3, 2017) "Vertex announces presentations of data at North American Cystic Fibrosis Conference that Demonstrate Important Progress Toward Goal of Helping All People with CF," Health and Medicine Week, vol. 3, p. 196.
Vodak, D. (2014) "Design and Development of HPMCAS-Based Spray-Dried Dispersions," 303-322.
Wainwright, C.E. et al. (2015) "Lumacaftor-Ivacaftor in Patients with Cystic Fibrosis Homozygous for Phe508del CFTR," *The New England Journal of Medicine*, 373(3):220-231.
Willson T. M. et al. (1996) "Bone targeted drugs 2. Synthesis of estrogens with hydroxyapatite affinity," Bioorg. & Med. Chem. Lett., (6):1047-1050.
Winn, M. et al. (1993) "2-(Alkylamino)nicotinic Acid and Analogs. Potent Angiotensin II Antagonists" *Journal of Medicinal Chemistry*, 36(18):2676-2688.
Yarnell AT. "Heavy-Hydrogen Drugs Turn Heads, Again" Chemical & Engineering News 2009; 87(25), 36-39.
Bhattacharya, S. et al. (1999) Polymorphism in Pharmaceutical Solids: Thermoanalytical and Crystallographic Methods (Brittain H. ed., 2d ed. Informa Healthcare USA, Inc. 2009) 318-335.
Boyle, M. "A CFTR corrector (lumacaftor) and a CFTR potentiator (ivacaftor) for treatment of patients with cystic fibrosis who have a phe508del CFTR mutation: a phase 2 randomised controlled trial," The Lancet Respiratory Medicine (Jul. 1, 2014) Retrieved from the Internet: https://www-clinicalkeycom-ez03.infotrieve.com/#!/content/playContent/1-s2.0S2213260014701328?returnurl=null&referrer=null.
Ivanisevic, I. (2011) "Uses of X-Ray Powder Diffraction in the Pharmaceutical Industry," Pharm. Form. Qual. 30-33.
NCT03029455 "A Study to Evaluate Safety and Pharmacokinetics of VX-659 in Healthy Subjects and in Adults With Cystic Fibrosis". Vertex Pharmaceuticals Incorporated, Retrieved from the Internet: https://clinicaltrials.gov/ct2/show/study/NCT03029455.
Notice of Allowance and Fee(s) Due for U.S. Appl. No. 16/702,891, dated Jul. 21, 2021.
Notice of Allowance and Fee(s) Due for U.S. Appl. No. 16/267,222, dated Jun. 16, 2021.

(56) References Cited

OTHER PUBLICATIONS

Notice of Allowance and Fee(s) Due for U.S. Appl. No. 16/829,765, dated Jun. 23, 2021.
Sołoducho, J. et al. "Synthesis of Some Pyrido[3,2g][1,2,5]triazocine Derivatives," *Polish Journal of Chemistry*, vol. 59, No. 10-12, Jan. 1, 1985, pp. 1115-1120.
Table 2 : List of the mutations or SNP tested in this study (https://www.jmdjournal.org/cms/10.2353/jmoldx.2008.080056/attachment/2286a276-d0b2-4a8a-83f8-8273bef9a761/mmc1.doc). Accessed Jan. 25, 2021.
"Vertex Provides Update on Ongoing Phase 3 Program for VX-661 in Combination with Ivacaftor for the Treatment of Cystic Fibrosis" (Aug. 15, 2016) Retrieved from the Internet: https://www.businesswire.com/news/home/20160815006099/en/Vertex-Update-Ongoing-Phase-3-Program-VX-661.

\* cited by examiner

FIG. 3

| Mutation cDNA Name | Mutation Protein Name | Mutation Legacy Name |
| --- | --- | --- |
| c.1A>G | p.? (unknown) | M1V |
| c.54-5940_273+10250del21kb | pSer18ArgfsX16 | CFTRdele2,3 |
| c.91C>T | p.Arg31Cys | R31C |
| c.115C>T | p.Gln39X | Q39X |
| c.137C>A | p.Ala46Asp | A46D |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88IlefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.Ile105SerfsX2 | 444delA |
| c.325_327delTATinsG | p.Tyr109GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.Ile148LeufsX5 | 574delA |
| c.443T>C | p.Ile148Thr | I148T |
| c.489+1G>T | No protein name | 621+1G->T |

FIG. 3 (continued)

| Mutation cDNA Name | Mutation Protein Name | Mutation Legacy Name |
|---|---|---|
| c.531delT | p.Ile177MetfsX12 | 663delT |
| c.532G>A | p.Gly178Glu | G178R |
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| C.595OT | p.His199Tyr | H199Y |
| C.613CM | p.Pro205Ser | P205S |
| c.617T>G | p.Leu206Trp | L206W |
| C.658OT | p.Gln220X | Q220X |
| c.680T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ile | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A; 1079C>A] | p.[Gln359Lys;Thr360Lys] | Q359K/T360K |
| c.1081delT | p.Trp361GlyfsX8 | 1213delT |
| c.1116+1G>A | No protein name | 1248+1G->A |
| c.1127_1128insA | p.Gln378AlafsX4 | 1259insA |
| c.1153_1154insAT | p.Asn386IlefsX3 | 1288insTA |

FIG. 3 (continued)

| Mutation cDNA Name | Mutation Protein Name | Mutation Legacy Name |
|---|---|---|
| c.1202G>A or c.1203G>A | p.Trp401X | W401X |
| c.1209+1G>A | No protein name | 1341+1G->A |
| c.1210-12[5] | No protein name | 5T |
| c.1210-12[7] | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1G47T>G | p.Ser549Arg | S549R |
| | | |
| c.1646G>A | p.Ser549Asn | S549N |
| c.1650delA | p.Gly551ValfsX8 | 1782delA |
| c.1651G>A | p.Gly551Ser | G551S |

FIG. 3 (continued)

| Mutation cDNA Name | Mutation Protein Name | Mutation Legacy Name |
|---|---|---|
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9ins | pSer641ArgfsX5 | 2055del9->A |
| c.1973_1985del13insAGAAA | p.Arg658 LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |
| c.2051_2052delAAinsG | p.Lys684SerfsX38 | 2183AA->G+ |
| c.205 I_2052delAAinsG | p.Lys684SerfsX38 | 2183delAA->G# |

FIG. 3 (continued)

| Mutation cDNA Name | Mutation Protein Name | Mutation Legacy Name |
|---|---|---|
| c.2052_2053insA | p.Gln685Th rfsX4 | 2184insA |
| c.2052delA | p.Lys684AsnfsX38 | 2184delA |
| c.2125oT | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547oA | p.Tyr849X | Y849X |
| c.2551C>T | p.Arg851X | R851X |
| c.2583delT | p.Phe861LeufsX3 | 2711delT |
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |
| c.2737_2738insG |  | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |

FIG. 3 (continued)

| Mutation cDNA Name | Mutation Protein Name | Mutation Legacy Name |
|---|---|---|
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |
| c.3205G>A | p.Gly1069Arg | G1069R |
| c.3208C>T | p.Arg1070Trp | R1070W |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |
| c.3484C>T | p.Arg1162X | R1162X |

FIG. 3 (continued)

| Mutation cDNA Name | Mutation Protein Name | Mutation Legacy Name |
|---|---|---|
| c.3485G>T | p.Arg1162Leu | R1162L |
| c.3528delC | p.Lys1177SerfsX15 | 3659delC |
| c.3535_3536insTCAA | p.Thr1179IlefsX17 | 3667ins4 |
| c.3587C>G | p.Ser1196X | S1196X |
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |
| c.3691delT | p.Ser1231ProfsX4 | 3821delT |
| c.3700A>G | p.Ile1234Val | I1234V |
| c.3705T>G | p.Ser1235Arg | S1235R |
| c.3717+12191C>T | No protein name | 3849+10kbC->T |
| c.3715-1G>A | No protein name | 3850-1G->A |
| c.3731G>A | p.Gly1244Glu | G1244E |
| c.3744delA | p.Lys1250ArgfsX9 | 3876delA |
| c.3752G>A | p.Ser1251Asn | S1251N |
| c.3763T>C | p.Ser1255Pro | S1255P |
| c.3764C>A | p.Ser1255X | S1255X |
| c.3773_3774insT | p.Leu1258PhefsX7 | 3905insT |
| c.3808G>A | p.Asp1270Asn | D1270N |
| c.3846G>A | p.Trp1282X | W1282X |
| c.3873+1G>A | No protein name | 4005+1G->A |
| c.3883delA | p.Ile1295PhefsX33 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |
| c.3964-78_4242+577del | NULL | CFTRdele22,23 |

FIG. 3 (continued)

| Mutation cDNA Name | Mutation Protein Name | Mutation Legacy Name |
|---|---|---|
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+IG>T | No protein name | 4374+IG->T |
| c.4251delA | p.Glu1418ArgfsX14 | 4382delA |
| c.4296_4297insGA | p.Ser1435GlyfsX14 | 4428insGA |

METHODS OF TREATMENT FOR CYSTIC FIBROSIS

This application is a national stage application under 35 U.S.C. § 371 of international application number PCT/US2018/036610, filed Jun. 8, 2018, which designated the U.S. and claims priority to U.S. Provisional Application 62/517,049, filed Jun. 8, 2017, U.S. Provisional Application 62/533,381, filed Jul. 17, 2017, U.S. Provisional Application 62/562,044, filed Sep. 22, 2017, U.S. Provisional Application 62/623,757, filed Jan. 30, 2018, U.S. Provisional Application 62/633,021, filed Feb. 20, 2018, U.S. Provisional Application 62/649,266, filed Mar. 28, 2018, all of which are incorporated herein by reference in their entirety.

Disclosed herein is a modulator of Cystic Fibrosis Transmembrane Conductance Regulator (CFTR), pharmaceutical compositions containing the modulator, methods of treatment of cystic fibrosis, and a process for making the modulator.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence, and is commonly referred to as the F508del mutation. This mutation occurs in approximately 70% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $N^+$—$K^+$ ATPase pump and Cl— channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $N^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Accordingly, there is a need for novel treatments of CFTR mediated diseases.

Disclosed herein is Compound I and pharmaceutically acceptable salts thereof. Compound I can be depicted as having the following structure:

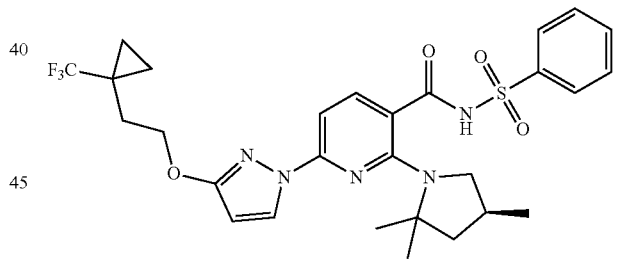

A chemical name for Compound I is N-(benzenesulfonyl)-6-[3-[2-[1-(trifluoromethyl)cyclopropyl]ethoxy]pyrazol-1-yl]-2-[(4(S))-2,2,4-trimethylpyrrolidin-1-yl]pyridine-3-carboxamide.

Also disclosed herein are pharmaceutical compositions comprising Compound I and/or at least one pharmaceutically acceptable salt thereof, which compositions may further include at least one additional active pharmaceutical ingredient and/or at least one carrier. Also disclosed are methods of treating the CFTR-mediated disease cystic fibrosis comprising administering Compound I and/or at least one pharmaceutically acceptable salt thereof, optionally as part of a pharmaceutical composition comprising at least one additional component, to a subject in need thereof. A process of making Compound I and/or pharmaceutically acceptable salts thereof is also disclosed.

Also disclosed are methods of treating the CFTR-mediated disease cystic fibrosis comprising administering N-(benzenesulfonyl)-6-[3-[2-[1-(trifluoromethyl)cyclopropyl]ethoxy]pyrazol-1-yl]-2-[(4(S))-2,2,4-trimethylpyrrolidin-1-yl]pyridine-3-carboxamide (Compound I), (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II), and N-[2,4-bis(1,1-dimethylethyl)-5-hydroxyphenyl]-1,4-dihydro-4-oxoquinoline-3-carboxamide (Compound III) or N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (Compound III-d), optionally as part of at least one pharmaceutical composition comprising at least one additional component, to a patient in need thereof.

BRIEF DESCRIPTION OF THE DRAWINGS

FIG. 3 is a representative list of CFTR genetic mutations.

DEFINITIONS

Figure 1:
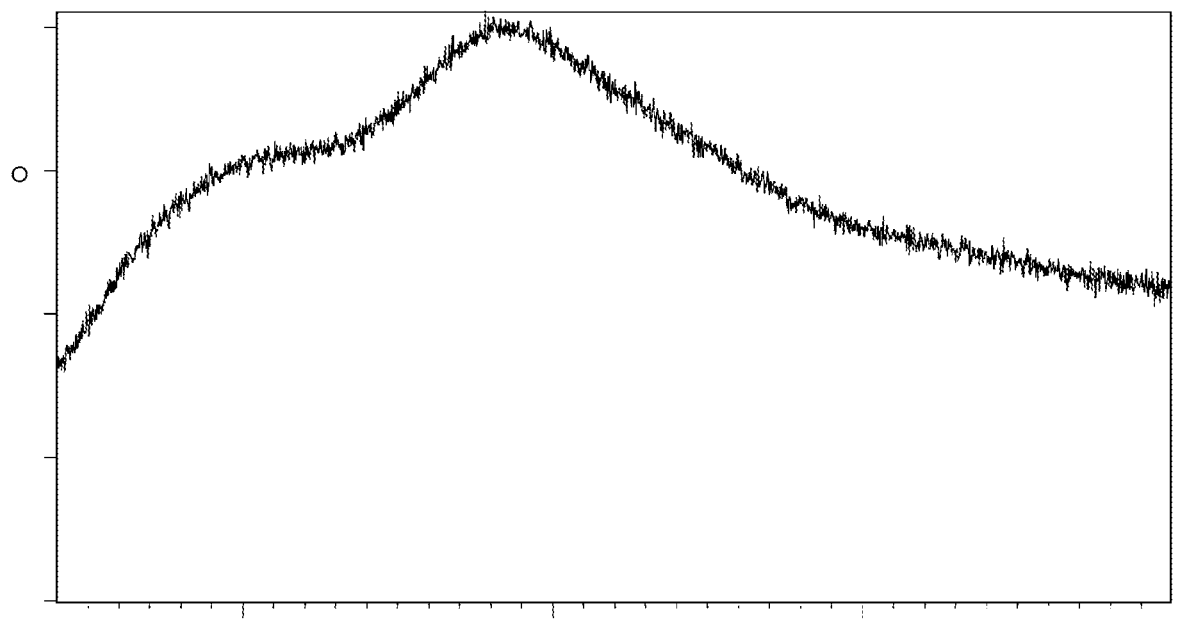
FIG. 1 is an XRPD of a spray dried dispersion of Compound I with HPMCAS-HG.

As used herein, "CFTR" means cystic fibrosis transmembrane conductance regulator.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on each allele.

As used herein, a patient who is "heterozygous" for a particular gene mutation has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compounds I and II disclosed herein are CFTR correctors.

As used herein, the term "CFTR potentiator" refers to a compound that increases the channel activity of CFTR protein located at the cell surface, resulting in enhanced ion transport. Compound III and III-d disclosed herein are CFTR potentiators.

As used herein, the term "active pharmaceutical ingredient" or "therapeutic agent" ("API") refers to a biologically active compound.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describes pharmaceutically acceptable salts in detail in *J. Pharmaceutical Sciences*, 1977, 66, 1-19.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material. In some embodiments, a solid material may comprise an amorphous compound, and the material may, for example, be characterized by a lack of sharp characteristic crystalline peak(s) in its XRPD spectrum (i.e. the material is not crystalline, but is amorphous, as determined by XRPD). Instead, one or several broad peaks (e.g. halos) may appear in the XRPD pattern of the material. See US 2004/0006237 for a comparison of XRPDs of an amorphous material and crystalline material. A solid material, comprising an amorphous compound, may be characterized by, for example, a wider temperature range for the melting of the solid material, as compared to the range for the melting of a pure crystalline solid. Other techniques, such as, for example, Raman spectroscopy, infrared spectroscopy, and solid state NMR may be used to characterize crystalline or amorphous forms.

In some embodiments, a solid material may comprise a mixture of crystalline solids and amorphous solids. A solid material prepared to comprise an amorphous compound may also, for example, contain up to 30% of a crystalline solid. In some embodiments, a solid material prepared to comprise an amorphous compound may also, for example, contain up to 25%, 20%, 15%, 10%, 5%, or 2% of a crystalline solid. In embodiments wherein the solid material contains a mixture of crystalline solids and amorphous solids, the characterizing data, such as XRPD, may contain indicators of both crystalline and amorphous solids. As used herein, the term "substantially amorphous" refers to a solid material having little or no long range order in the position of its molecules. For example, substantially amorphous materials have less than 15% crystallinity (e.g., less than 10% crystallinity or less than 5% crystallinity). It is also noted that the term 'substantially amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase, and the drug constitute the continuous phase. Or, a solid dispersion includes the drug constituting the dispersed phase, and the polymer constituting the continuous phase.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The term "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

Each of Compounds I, II, III, and III-d, and their pharmaceutically acceptable salts thereof independently can be administered once daily, twice daily, or three times daily. In some embodiments, at least one compound chosen from Compound I and pharmaceutically acceptable salts thereof is administered once daily. In some embodiments, at least one compound chosen from Compound I and pharmaceutically acceptable salts thereof are administered twice daily. In some embodiments, at least one compound chosen from Compound II and pharmaceutically acceptable salts thereof is administered once daily. In some embodiments, at least one compound chosen from Compound II and pharmaceutically acceptable salts thereof is administered twice daily. In some embodiments, at least one compound chosen from Compound III or III-d and pharmaceutically acceptable salts thereof is administered once daily. In some embodiments, at least one compound chosen from Compound III or III-d and pharmaceutically acceptable salts thereof is administered twice daily.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "100 mg of at least one compound chosen from Compound I and pharmaceutically acceptable salts thereof" includes 100 mg of Compound I and a concentration of a pharmaceutically acceptable salt of Compound I equivalent to 100 mg of Compound I.

As stated above, disclosed herein is Compound I, which can be depicted as having the following structure:

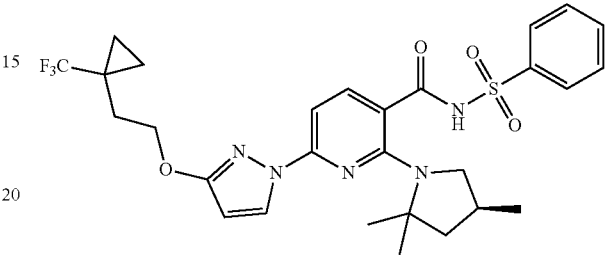

A chemical name for Compound I is N-(benzenesulfonyl)-6-[3-[2-[1-(trifluoromethyl)cyclopropyl]ethoxy]pyrazol-1-yl]-2-[(4(S))-2,2,4-trimethylpyrrolidin-1-yl]pyridine-3-carboxamide. Compound I may be in the form of a pharmaceutically acceptable salt thereof.

In some embodiments, Compound I (and/or at least one pharmaceutically acceptable salt thereof) can be administered in combination with at least one additional active pharmaceutical ingredient. In some embodiments, the at least one additional active pharmaceutical ingredient is chosen from:

(a) Compound II:

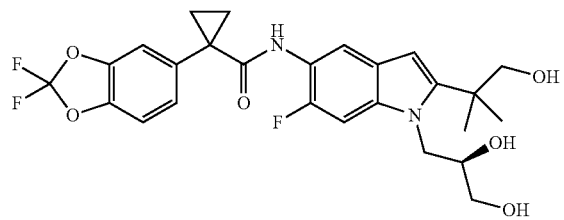 [SMILES: CC(C)(CO)c1cc2cc(NC(=O)C3(c4ccc5c(c4)OC(F)(F)O5)CC3)c(F)cc2n1C[C@@H](O)CO]

and pharmaceutically acceptable salts thereof.

A chemical name for Compound II is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide;

(b) Compound III or Compound III-d:

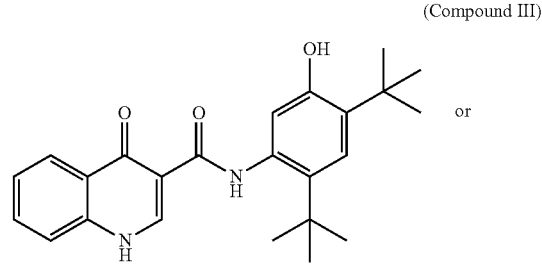

(Compound III)

or

-continued (Compound III-d)

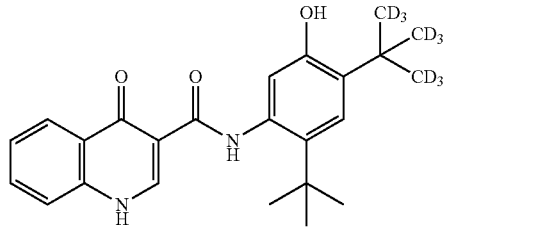

and pharmaceutically acceptable salts thereof

A chemical name for Compound III is N-(5-hydroxy-2,4-di-tert-butyl-phenyl)-4-oxo-1H-quinoline-3-carboxamide and a chemical name for Compound III-d is N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide; and (c) Compound IV:

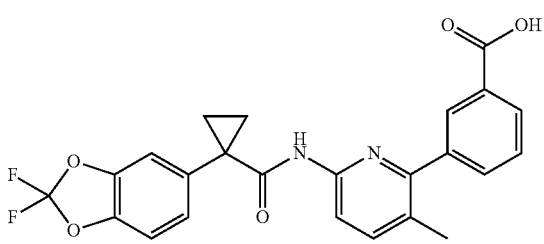 [SMILES: Cc1ccc(NC(=O)C2(c3ccc4c(c3)OC(F)(F)O4)CC2)nc1-c1cccc(C(=O)O)c1]

and pharmaceutically acceptable salts thereof.

A chemical name for Compound IV is 3-(6-(1-(2,2-difluorobenzo[d][1,3]dioxol-5-yl)cyclopropanecarboxamido)-3-methylpyridin-2-yl)benzoic acid.

Suitable pharmaceutically acceptable salts are, for example, those disclosed in S. M. Berge, et al. *J. Pharmaceutical Sciences,* 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

In some embodiments, at least one compound chosen from Compound I and pharmaceutically acceptable salts thereof is administered in combination with at least one compound chosen from Compound II and pharmaceutically acceptable salts thereof. In some embodiments, at least one compound chosen from Compound I and pharmaceutically acceptable salts thereof is administered in combination with at least one compound chosen from Compound III and pharmaceutically acceptable salts thereof. In some embodiments, at least one compound chosen from Compound I and pharmaceutically acceptable salts thereof is administered in combination with at least one compound chosen from Compound IV and pharmaceutically acceptable salts thereof. In some embodiments, at least one compound chosen from Compound I and pharmaceutically acceptable salts thereof is administered in combination with Compounds II or a pharmaceutically acceptable salt thereof and at least one compound chosen from Compound III and pharmaceutically acceptable salts thereof. In some embodiments, at least one compound chosen from Compound I and pharmaceutically acceptable salts thereof is administered in combination with at least one compound chosen from Compound III and pharmaceutically acceptable salts thereof and at least one compound chosen from Compound IV and pharmaceutically acceptable salts thereof. In some embodiments, at least one compound chosen from Compound I and pharmaceutically acceptable salts thereof is administered in combination with at least one compound chosen from Compound III-d and pharmaceutically acceptable salts thereof. In some embodiments, at least one compound chosen from Compound I and pharmaceutically acceptable salts thereof is administered in combination with at least one compound chosen from Compound IV and pharmaceutically acceptable salts thereof. In some embodiments, at least one compound chosen from Compound I and pharmaceutically acceptable salts thereof is administered in combination with Compounds II or a pharmaceutically acceptable salt thereof and at least one compound chosen from Compound III-d and pharmaceutically acceptable salts thereof. In some embodiments, at least one compound chosen from Compound I and pharmaceutically acceptable salts thereof is administered in combination with at least one compound chosen from Compound III-d and pharmaceutically acceptable salts thereof and at least one compound chosen from Compound IV and pharmaceutically acceptable salts thereof.

Each of Compounds I, II, III, III-d, and IV and their pharmaceutically acceptable salts thereof independently can be administered once daily, twice daily, or three times daily. In some embodiments, at least one compound chosen from Compound I and pharmaceutically acceptable salts thereof is administered once daily. In some embodiments, at least one compound chosen from Compound I and pharmaceutically acceptable salts thereof is administered twice daily. In some embodiments, Compound II or its pharmaceutically acceptable salts thereof are administered once daily. In some embodiments, Compound II or its pharmaceutically acceptable salts thereof are administered twice daily. In some embodiments, Compound III or its pharmaceutically acceptable salts thereof are administered once daily. In some embodiments, Compound III or its pharmaceutically acceptable salts thereof are administered twice daily. In some embodiments, Compound III-d or its pharmaceutically acceptable salts thereof are administered once daily. In some embodiments, Compound III-d or its pharmaceutically acceptable salts thereof are administered twice daily. In some embodiments, Compound IV or its pharmaceutically acceptable salts thereof are administered once daily. In some embodiments, Compound IV or its pharmaceutically acceptable salts thereof are administered twice daily.

In some embodiments, at least one compound chosen from Compound I and pharmaceutically acceptable salts thereof is administered in an amount of 10 mg to 900 mg, 20 mg to 800 mg, 80 mg to 800 mg, 30 mg to 720 mg, 40 mg to 600 mg, 60 mg to 100 mg, 60 mg to 500 mg, 80 mg to 400 mg, 120 mg to 240 mg, 120 mg to 360 mg, 160 mg to 320 mg, 240 mg to 400 mg, 320 mg to 480 mg, or 360 mg to 640 mg daily. In some embodiments, 80 mg, 120 mg, 160 mg, 240 mg, 320 mg, 400 mg, 480 mg, 560 mg, 640 mg, or 720 mg of Compound I or its pharmaceutically acceptable salts are administered once daily. In some embodiments, 80 mg, 120 mg, 160 mg, 240 mg, 320 mg, or 400 mg of Compound I or its pharmaceutically acceptable salts are administered twice daily.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "100 mg of Compound I or its pharmaceutically acceptable salt" includes 100 mg of Compound I and a concentration of a pharmaceutically acceptable salt of Compound I equivalent to 100 mg of Compound I.

Compounds I, II, III, III-d, IV, and their pharmaceutically acceptable salts thereof can be comprised in a single pharmaceutical composition or separate pharmaceutical compositions. Such pharmaceutical compositions can be administered once daily or multiple times daily, such as twice daily. As used herein, the phrase that a given amount of API (e.g., Compound I, II, III, III-d, IV, or a pharmaceutically acceptable salt thereof) is administered once or twice daily or per day means that said given amount is administered per dosing once or twice daily. For example, the phrase that 50 mg of Compound II or a pharmaceutically acceptable salt thereof is administered twice daily or per day means that 50 mg of Compound II or a pharmaceutically acceptable salt thereof is administerd per dosing twice per day (e.g., 50 mg of Compound II or a pharmaceutically acceptable salt thereof is administerd in the morning and 50 mg of Compound II or a pharmaceutically acceptable salt thereof is administered in the evening).

In some embodiments, at least one compound chosen from Compound I and pharmaceutically acceptable salts thereof is comprised in a first pharmaceutical composition; at least one compound chosen from Compound II and pharmaceutically acceptable salts thereof is comprised in a second pharmaceutical composition; and at least one compound chosen from Compound III or III-d and pharmaceutically acceptable salts thereof is comprised in a third pharmaceutical composition.

In some embodiments, at least one compound chosen from Compound I and pharmaceutically acceptable salts thereof is comprised in a first pharmaceutical composition; at least one compound chosen from Compound II and pharmaceutically acceptable salts thereof is comprised in a second pharmaceutical composition; at least one compound chosen from Compound III or III-d and pharmaceutically acceptable salts thereof is comprised in a third pharmaceutical composition; and at least one compound chosen from Compound IV and pharmaceutically acceptable salts thereof is comprised in a third pharmaceutical composition.

In some embodiments, at least one compound chosen from Compound I and pharmaceutically acceptable salts thereof is comprised in a first pharmaceutical composition; and at least one compound chosen from Compound II and pharmaceutically acceptable salts thereof and at least one compound chosen from Compound III or III-d and pharmaceutically acceptable salts thereof are comprised in a second pharmaceutical composition. In some embodiments, the second pharmaceutical composition comprises a half of a daily dose of said at least one compound chosen from Compound III or III-d and pharmaceutically acceptable salts thereof, and the other half of said at least one compound chosen from Compound III or III-d and pharmaceutically acceptable salts thereof is administered in a third pharmaceutical composition.

In some embodiments, at least one compound chosen from Compound I and pharmaceutically acceptable salts thereof is comprised in a first pharmaceutical composition; at least one compound chosen from Compound II and pharmaceutically acceptable salts thereof; and at least one compound chosen from Compound III or III-d and pharmaceutically acceptable salts thereof are comprised in a first pharmaceutical composition. In some embodiments, the first pharmaceutical composition is administered to the patient twice daily.

In some embodiments, the disclosure features a pharmaceutical composition comprising at least one compound chosen from Compound I and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound II and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound III or III-d and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound II and pharmaceutically acceptable salts thereof, at least one compound chosen from Compound III or III-d and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound III or III-d and pharmaceutically acceptable salts thereof, at least one compound chosen from Compound IV and pharmaceutically acceptable salts thereof, and at least one pharmaceutically acceptable carrier.

In some embodiments, pharmaceutical compositions disclosed herein comprise at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises Compound I and at least two additional active pharmaceutical ingredients, one of which is a CFTR corrector and one of which is a CFTR potentiator.

In some embodiments, at least one additional active pharmaceutical ingredient is selected from mucolytic agents, bronchodilators, antibiotics, anti-infective agents, and anti-inflammatory agents.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure, including a pharmaceutical composition comprising combinations described previously, can be employed in combination therapies; that is, the compositions can be administered concurrently with, prior to, or subsequent to, at least one additional active pharmaceutical ingredient or medical procedures.

Pharmaceutical compositions comprising these combinations are useful for treating cystic fibrosis.

In some embodiments, a pharmaceutical composition disclosed herein comprises at least one compound chosen from Compound I and pharmaceutically acceptable salts thereof, and at least one pharmaceutically acceptable carrier. In some embodiments, the pharmaceutically acceptable carrier is a polymer. In some embodiments, the pharmaceutically acceptable carrier is HPMCAS. In some embodiments, the pharmaceutically acceptable carrier is HPMCAS-HG. In some embodiments, the pharmaceutical composition comprises a solid dispersion of compound I in HPMCAS-HG. In some embodiments, the solid dispersion comprises compound I in HPMCAS-HG in a 1:1 weight ratio. In some embodiments, the solid dispersion comprises substantially amorphous compound I.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

It will also be appreciated that a pharmaceutical composition of this disclosure, including a pharmaceutical composition comprising any of the combinations described previously, can be employed in combination therapies; that is, the compositions can be administered concurrently with, prior to, or subsequent to, at least one active pharmaceutical ingredients or medical procedures.

In some embodiments, the methods of the disclosure employ administering to a patient in need thereof at least one compound chosen from Compound I and pharmaceutically acceptable salts thereof; and at least one compound chosen from Compound II, Compound III or III-d, Compound IV; and pharmaceutically acceptable salts of any of the foregoing.

Any suitable pharmaceutical compositions known in the art can be used for Compound I, Compound II, Compound III or III-d, Compound IV, and pharmaceutically acceptable salts thereof. Some exemplary pharmaceutical compositions for Compound I and its pharmaceutically acceptable salts are described in the Examples. Some exemplary pharmaceutical compositions for Compound II and its pharmaceutically acceptable salts can be found in WO 2011/119984 and WO 2014/015841, all of which are incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, and some exemplary pharmaceutical compositions for Compound III-d and its pharmaceutically acceptable salts can be found in U.S. Pat. Nos. 8,865,902, 9,181,192, and 9,512,079 all of which are incorporated herein by reference. Some exemplary pharmaceutical compositions for Compound IV and its pharmaceutically acceptable salts can be found in WO 2010/037066, WO 2011/127241, WO 2013/112804, and WO 2014/071122, all of which are incorporated herein by reference.

In some embodiments, a pharmaceutical composition comprising at least one compound chosen from Compound I and pharmaceutically acceptable salts thereof is administered with a pharmaceutical composition comprising Compound II and Compound III or III-d. Pharmaceutical compositions comprising Compound II and Compound III are disclosed in PCT Publication No. WO 2015/160787, incorporated herein by reference. An exemplary embodiment is shown in the following Table:

TABLE 2

Exemplary Tablet Comprising 100 mg of Compound II and 150 mg of Compound III.

| | Ingredient | Amount per tablet (mg) |
|---|---|---|
| Intra-granular | Compound II SDD (spray dried dispersion) (80 wt % Compound II; 20 wt % HPMC) | 125 |
| | Compound III SDD (80 wt % Compound III; 19.5 wt % HPMCAS-HG; 0.5 wt % sodium lauryl sulfate) | 187.5 |
| | Microcrystalline cellulose | 131.4 |
| | Croscarmellose Sodium | 29.6 |
| | Total | 473.5 |
| Extra-granular | Microcrystalline cellulose | 112.5 |
| | Magnesium Stearate | 5.9 |
| | Total | 118.4 |
| Total uncoated Tablet | | 591.9 |
| Film coat | Opadrn | 17.7 |
| Total coated Tablet | | 609.6 |

In some embodiments, a pharmaceutical composition comprising Compound I is administered with a pharmaceutical composition comprising Compound III or III-d. Pharmaceutical compositions comprising Compound III are disclosed in PCT Publication No. WO 2010/019239, incorporated herein by reference. An exemplary embodiment is shown in the following Table:

TABLE 3

Ingredients for Exemplary Tablet of Compound III.

| Tablet Formulation | Percent Dose % Wt./Wt. | Dose (mg) | Batch (g) |
|---|---|---|---|
| Compound III SDD (80 wt % Compound III; 19.5 wt % HPMCAS-HG; 0.5 wt % sodium lauryl sulfate) | 34.09% | 187.5 | 23.86 |
| Microcrystalline cellulose | 30.51% | 167.8 | 21.36 |
| Lactose | 30.40% | 167.2 | 21.28 |
| Sodium croscarmellose | 3.000% | 16.50 | 2.100 |
| SLS | 0.500% | 2.750 | 0.3500 |
| Colloidal silicon dioxide | 0.500% | 2.750 | 0.3500 |
| Magnesium stearate | 1.000% | 5.500 | 0.7000 |
| Total | 100% | 550 | 70 |

Additional pharmaceutical compositions comprising Compound III are disclosed in PCT Publication No. WO 2013/130669, incorporated herein by reference. Exemplary mini-tablets (~2 mm diameter, ~2 mm thickness, each mini-tablet weighing about 6.9 mg) was formulated to have approximately 50 mg of Compound III per 26 mini-tablets and approximately 75 mg of Compound III per 39 mini-tablets using the amounts of ingredients recited in Table 4, below.

TABLE 4

Ingredients for mini-tablets for 50 mg and 75 mg potency

| Tablet Formulation | Percent Dose % Wt./Wt. | Dose (mg) 50 mg potency | Dose (mg) 75 mg potency | Batch (g) |
|---|---|---|---|---|
| Compound III SDD (80 wt % Compound III; 19.5 wt % HPMCAS-HG; 0.5 wt % sodium lauryl sulfate) | 35 | 62.5 | 93.8 | 1753.4 |
| Mannitol | 13.5 | 24.1 | 36.2 | 675.2 |
| Lactose | 41 | 73.2 | 109.8 | 2050.2 |
| Sucralose | 2.0 | 3.6 | 5.4 | 100.06 |
| Croscarmellose sodium | 6.0 | 10.7 | 16.1 | 300.1 |
| Colloidal silicon dioxide | 1.0 | 1.8 | 2.7 | 50.0 |
| Magnesium stearate | 1.5 | 2.7 | 4.0 | 74.19 |
| Total | 100 | 178.6 | 268 | 5003.15 |

In some embodiments, the pharmaceutical compositions are a tablet. In some embodiments, the tablets are suitable for oral administration.

These combinations are useful for treating cystic fibrosis.

The compounds, pharmaceutically acceptable salts thereof, and deuterated analogs of any of the foregoing, and the pharmaceutical compositions can be used for treating cystic fibrosis.

A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect).

Mutations that affect CFTR function include mutations that cause defective gating (Class III defect) and mutations that cause defective conductance (Class IV defect).

In some embodiments, disclosed herein methods of treating, lessening the severity of, or symptomatically treating cystic fibrosis in a patient comprising administering an effective amount of a compound, pharmaceutically acceptable salt thereof, or a deuterated analog of any of the foregoing; or a pharmaceutical composition, of this disclosure to a patient, such as a human, wherein said patient has cystic fibrosis. In some embodiments, the patient has F508del/minimal function (MF) genotypes, F508del/F508del genotypes, F508del/gating genotypes, or F508del/residual function (RF) genotypes.

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance. Table C below includes a non-exclusive list of CFTR minimal function mutations, which are detectable by an FDA-cleared genotyping assay. In some embodiments, a mutation is considered a MF mutation if it meets at least 1 of the following 2 criteria:

(1) biological plausibility of no translated protein (genetic sequence predicts the complete absence of CFTR protein), or
(2) in vitro testing that supports lack of responsiveness to Compound II, Compound III or the combination of Compound II and Compound III, and evidence of clinical severity on a population basis (as reported in large patient registries).

In some embodiments, the minimal function mutations are those that result in little-to-no functioning CFTR protein and are not responsive in vitro to Compound II, Compound III, or the combination of Compound II and Compound III.

In some embodiments, the minimal function mutations are those that are not responsive in vitro to Compound II, Compound III, or the combination of Compound II and Compound III. In some embodiments, the minimal function mutations are mutations based on in vitro testing met the following criteria in in vitro experiments:
baseline chloride transport that was <10% of wildtype CFTR, and
an increase in chloride transport of <10% over baseline following the addition of TEZ, IVA, or TEZ/IVA in the assay.

In some embodiments, patients with at least one minimal function mutation exhibit evidence of clinical severity as defined as:
average sweat chloride >86 mmol/L, and
prevalence of pancreatic insufficiency (PI)>50%.

Patients with an F508del/minimal function genotype are defined as patients that are heterozygous F508del-CFTR with a second CFTR allele containing a minimal function mutation. In some embodiments, patients with an F508del/minimal function genotype are patients that are heterozygous F508del-CFTR with a second CFTR allele containing a mutation that results in a CFTR protein with minimal CFTR function (little-to-no functioning CFTR protein) and that is not responsive in vitro to Compound II, Compound III, or the combination of Compound II and Compound III.

In some embodiments, minimal function mutations can be determined using 3 major sources:
biological plausibility for the mutation to respond (i.e., mutation class)
evidence of clinical severity on a population basis (per CFTR2 patient registry; accessed on 15 Feb. 2016)
average sweat chloride >86 mmol/L, and
prevalence of pancreatic insufficiency (PI) >50%
in vitro testing
mutations resulting in baseline chloride transport <10% of wild-type CFTR were considered minimal function
mutations resulting in chloride transport <10% of wild-type CFTR following the addition of Compound II and/or Compound III were considered nonresponsive.

As used herein, a "residual function mutations" refer to are Class II through V mutations that have some residual chloride transport and result in a less severe clinical phenotype. Residual function mutations are mutation in the CFTR gene that result in reduced protein quantity or function at the cell surface which can produce partial CFTR activity.

Non-limiting examples of CFTR gene mutations known to result in a residual function phenotype include a CFTR residual function mutation selected from 2789+5G→A, 3849+1 OkbC→T, 3272-26A→G, 711+3A→G, E56K, P67L, R74W, D11OE, D11OH, R117C, L206W, R347H, R352Q, A455E, D579G, E831X, S945L, S977F, F1052V, R1070W, F1074L, D1152H, D1270N, E193K, and K1060T. For example, CFTR mutations that cause defective mRNA splicing, such as 2789+507 A, result in reduced protein synthesis, but deliver some functional CFTR to the surface of the cell to provide residual function. Other CFTR mutations that reduce conductance and/or gating, such as R117H, result in a normal quantity of CFTR channels at the surface of the cell, but the functional level is low, resulting in residual function. In some embodiments, the CFTR residual function mutation is selected from R117H, S1235R, I1027T, R668C, G576A, M470V, L997F, R75Q, R1070Q, R31C, D614G, G1069R, R1162L, E56K, A1067T, E193K, and K1060T. In some embodiments, the CFTR residual function mutation is selected from R117H, S1235R, I1027T, R668C, G576A, M470V, L997F, R75Q, R1070Q, R31C, D614G, G1069R, R1162L, E56K, and A1067T.

Residual CFTR function can be characterized at the cellular (in vitro) level using cell based assays, such as an FRT assay (Van Goar, F. et al. (2009) PNAS Vol. 106, No. 44, 18825-18830; and Van Goor, F. et al. (2011) PNAS Vol. 108, No. 46, 18843-18846), to measure the amount of chloride transport through the mutated CFTR channels. Residual function mutations result in a reduction but not complete elimination of CFTR dependent ion transport. In some embodiments, residual function mutations result in at least about 10% reduction of CFTR activity in an FRT assay. In some embodiments, the residual function mutations result in up to about 90% reduction in CFTR activity in an FRT assay.

Patients with an F508del/residual function genotype are defined as patients that are heterozygous F508del-CFTR with a second CFTR allele that contains a mutation that results in reduced protein quantity or function at the cell surface which can produce partial CFTR activity.

Patients with an F508del/gating mutation genotype are defined as patients that are heterozygous F508del-CFTR with a second CFTR allele that contains a mutation associated with a gating defect and clinically demonstrated to be responsive to Compound III. Examples of such mutations include: G178R, S549N, S549R, G551D, G551S, G1244E, S1251N, S1255P, and G1349D.

In some embodiments, the methods of treating, lessening the severity of, or symptomatically treating cystic fibrosis disclosed herein are each independently produces an increase in chloride transport above the baseline chloride transport of the patient.

In some embodiments, in the methods of treating, lessening the severity of, or symptomatically treating cystic fibrosis disclosed herein, the patient is heterozygous for F508del, and the other CFTR genetic mutation is any CF-causing mutation. In some embodiments, the paient is heterozygous for F508del, and the other CFTR genetic mutation is any CF-causing mutation, and is expected to be and/or is responsive to any of the novel compounds disclosed herein, such as Compound 1, Compound II, Compound III and/or Compound IV genotypes based on in vitro and/or clinical data. In some embodiments, the paient is heterozygous for F508del, and the other CFTR genetic mutation is any CF-causing mutation, and is expected to be and/or is responsive to any combinations of (i) the novel compounds disclosed herein, such as Compound 1, and (ii) Compound II, and/or Compound III and/or Compound IV genotypes based on in vitro and/or clinical data.

In some embodiments, in the methods of treating, lessening the severity of, or symptomatically treating cystic fibrosis disclosed herein, the patient possesses a CFTR genetic mutation selected from any of the mutations listed in Table A.

TABLE A

| CF Mutations | | |
|---|---|---|
| 078delT | 2043delG | 3121- |
| 1078delT | 2055del9→A | 977_3499+248del2515 |
| 11234V | 2105- | 3132delTG |
| 1154insTC | 2117del13insAGAAA | 3141del9 |
| 1161delC | 2118del14 | 3171delC |
| 1213delT | 2143delT | 3195del6 |
| 1248+1G→A | 2183AA->G+ | 3199del6 |
| 1249-1G→A | 2183AA→G | 3272-26A->G |
| 124del23bp | 2183AA→G$^a$ | 3500-2A→G |
| 1259insA | 2183delAA->G# | 3600+2insT |
| 1288insTA | 2183delAA→G | 365-366insT |
| 1341+1G->A | 2184delA | 3659delC |
| 1342-2A->C | 2184insA | 3667ins4 |
| 1461ins4 | 2307insA | 3737delA |
| 1471delA | 2347delG | 3791delC |
| 1497delGG | 2556insAT | 3821delT |
| 1507del | 2585delT | 3849+10kbC→T |
| 1525-1G→A | 2594delGT | 3849+IOkbC->T |
| 1525-2A→G | 2622+1G->A | 3850-1G->A |
| 1548delG | 2622+IG->A | 3850-3T->G |
| 1577delTA | 2659delC | 3850-IG->A |
| 1609del CA | 2711delT | 3876delA |
| 1677delTA | 271delT | 3878delG |
| 1716G/A | 2721del11 | 3905InsT |
| 1717-1G→A | 2732insA | |
| 1717-8G→A | | 3905insT |
| 1782delA | 2789+2insA | 394delTT |
| 1811+1.6kbA->G | 2789+5G→A | 4005+1G->A |
| 1811+1G->C | 2790-1G->C | 4005+2T->C |
| 1811+1.6kbA→G | 2790-IG->C | 4005+1G→A |
| 1811+1G→C | 2869insG | 4005+IG->A |
| 1812-1G->A | 2896insAG | 4010del4 |
| 1898+1G->A | 2942insT | 4015delA |
| 1812-1G→A | 2957delT | 4016insT |
| 1824delA | 296+1G→A | 4021dupT |
| 182delT 1119delA | 2991del32 | 4040delA |
| 185+1G→T | 3007delG | 405+1G→A |
| 1898+1G->T | 3028delA | 405+3A→C |
| 1898+1G→A | 3040G→C | 405+IG->A |
| | 306insA | 406-1G→A |

TABLE A-continued

| CF Mutations | | |
|---|---|---|
| 1898+1G→C | 306insA 1138insG | 406-IG->A |
| 1898+3A->G | 3120G→A | 4209TGTT->A |
| 1898+5G->T | 3121-1G→A | 4209TGTT→AA |
| 1924del7 | 3121-2A→G | 4279insA |
| 1949del84 | | 4326delTC |
| 4374+1G→T | D192G | G27R |
| 4374+IG->T | D443Y | G27X |
| 4382delA | D513G | G314E |
| 4428insGA | D579G | G330X |
| 442delA | D614G | G458V |
| 457TAT→G | D836Y | G463V |
| 541delC | D924N | G480C |
| 574delA | D979V | G542X |
| 5T | E1104X | G550X |
| 621+1G→T | E116K | G551D |
| 621+3A->G | E1371X | G551S |
| 663delT | E193K | G576A |
| 663delT 1548delG | E193X | G622D |
| 675del4 | E403D | G628R |
| 711+1G->T | E474K | G628R(G->A) |
| 711+3A->G | E56K | G970D |
| 711+1G→T | E585X | G673X |
| 711+3A→G | E588V | G85E |
| 711+5G→A | E60K | G91R |
| 712-1G->T | E822K | G970R |
| 7T | E822X | G970R |
| 852del22 | E831X | H1054D |
| 935delA | E92K | H1085P |
| 991del5 | E92X | H1085R |
| A1006E | F1016S | H1375P |
| A120T | F1052V | H139R |
| A234D | F1074L | H199R |
| A349V | F1099L | H199Y |
| A455E | F191V | H609R |
| A613T | F311del | H939R |
| A46D | F311L | I1005R |
| A46Db | F508C | I1027T |
| A559T | F508del | I1234V |
| A559Tb | F575Y | I1269N |
| A561E | G1061R | I1366N |
| C276X | G1069R | I148T |
| C524R | G1244E | I175V |
| C524X | G1249R | I3336K |
| CFTRdel2, 3 | G126D | I502T |
| CFTRdele22-23 | G1349D | I506S |
| D110E | G149R | I506T |
| D110H | G178R | I507del |
| D1152H | G194R | I507del |
| D1270N | G194V | I601F |
| I618T | P5L | R1283S |
| I807M | P67L | R170H |
| I980K | P750L | R258G |
| IVS14b+5G->A | P99L | R31C |
| K710X | Q1100P | R31L |
| K710X | Q1291H | R334L |
| K710X | Q1291R | R334Q |
| L102R | Q1313X | R334W |
| L1065P | Q1382X | R347H |
| L1077P | Q1411X | R347L |
| L1077Pb | Q1412X | R347P |
| L1254X | Q220X | R352Q |
| L1324P | Q237E | R352W |
| L1335P | Q237H | R516G |
| L138ins | Q452P | R553Q |
| L1480P | Q290X | R553X |
| L15P | Q359K/T360K | R560K |
| L165S | Q39X | R560S |
| L206W | Q414 | R560T |
| L218X | Q414X | R668C |
| L227R | E585X | R709X |
| L320V | Q493X | R74W |
| L346P | Q525X | R751L |
| L453S | Q552X | R75Q |
| L467P | Q685X | R75X |
| L467Pb | Q890X | R764X |
| L558S | Q890X | R792G |
| L571S | Q98R | R792X |
| L732X | Q98X | R851X |

TABLE A-continued

CF Mutations

| | | |
|---|---|---|
| L927P | R1066C | R933G |
| L967S | R1066H | S1118F |
| L997F | R1066M | S1159F |
| M1101K | R1070Q | S1159P |
| M1101R | R1070W | S1196X |
| M152V | R1102X | S1235R |
| M1T | R1158X | S1251N |
| M1V | R1162L | S1255P |
| M265R | R1162X | S1255X |
| M470V | R117C | S13F |
| M952I | R117G | S341P |
| M952T | R117H | S434X |
| N1303K | R117L | S466X |
| P205S | R117P | S489X |
| P574H | R1283M | S492F |
| S4X | Y122X | |
| S549N | Y161D | |
| S549R | Y161S | |
| S549R(A->C) | Y563D | |
| S549R(T->G) | Y563N | |
| S589N | Y569C | |
| S737F | Y569D | |
| S912L | Y569Db | |
| S912X | Y849X | |
| S945L | Y913C | |
| S977F | Y913X | |
| T1036N | | |
| T1053I | | |
| T1246I | | |
| T338I | | |
| T604I | | |
| V1153E | | |
| V1240G | | |
| V1293G | | |
| V201M | | |
| V232D | | |
| V456A | | |
| V456F | | |
| V520F | | |
| V562I | | |
| V754M | | |
| W1089X | | |
| W1098C | | |
| W1098R | | |
| W1098X | | |
| W1204X | | |
| W1282R | | |
| W1282X | | |
| W361R | | |
| W401X | | |
| W496X | | |
| W57G | | |
| W57R | | |
| W57X | | |
| W846X | | |
| Y1014C | | |
| Y1032C | | |
| Y1092X | | |
| Y109N | | |

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, 621+3A→>G, 1949del84, 3141del9, 3195del6, 3199del6, 3905InsT, 4209TGTT→A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G→A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, I980K, L102R, L1324P, L1335P, L138ins, L1480P, L15P, L165S, L320V, L346P, L453S, L571S, L967S, M1101R, M152V, M1T, M1V, M265R, M952I, M952T, P574H, PSL, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R (A→C), S549R(T→G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, the patient has at least one combination mutation chosen from: G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G.

In some embodiments, the patient has at least one combination mutation chosen from: 1949del84, 3141del9, 3195del6, 3199del6, 3905InsT, 4209TGTT→A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G→A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, I980K, L102R, L1324P, L1335P, L138ins, L1480P, L15P, L165S, L320V, L346P, L453S, L571S, L967S, M1101R, M152V, M1T, M1V, M265R, M952I, M952T, P574H, PSL, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A→C), S549R(T→G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, in the methods of treating, lessening the severity of, or symptomatically treating cystic fibrosis disclosed herein, the patient possesses a CFTR genetic mutation G551D. In some embodiments, the patient is homozygous for the G551D genetic mutation. In some embodiments, the patient is heterozygous for the G551D genetic mutation. In some embodiments, the patient is heterozygous for the G551D genetic mutation, having the G551D mutation on one allele and any other CF-causing mutation on the other allele. In some embodiments, the patient is heterozygous for the G551D genetic mutation on one allele and the other CF-causing genetic mutation on the other allele is any one of F508del, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T. In some embodiments, the patient is heterozygous for the G551D genetic mutation, and the other CFTR genetic mutation is F508del. In some embodiments, the patient is heterozygous for the G551D genetic mutation, and the other CFTR genetic mutation is R117H.

In some embodiments, in the methods of treating, lessening the severity of, or symptomatically treating cystic fibrosis disclosed herein, the patient possesses a CFTR genetic mutation F508del. In some embodiments, the patient is homozygous for the F508del genetic mutation. In some embodiments, the patient is heterozygous for the F508del genetic mutation wherein the patient has the F508del genetic mutation on one allele and any CF-causing genetic mutation on the other allele. In some embodiments, the patient is heterozygous for F508del, and the other CFTR genetic mutation is any CF-causing mutation, including, but not limited to G551D, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T. In some embodiments, the patient is heterozygous for F508del, and the other CFTR genetic mutation is G551D. In some embodiments, the patient is heterozygous for F508del, and the other CFTR genetic mutation is R117H.

In some embodiments, the patient has at least one combination mutation chosen from:
D443Y; G576A; R668C,
F508C; S1251N,
G576A; R668C,
G970R; M470V,
R74W; D1270N,
R74W; V201M, and
R74W; V201M; D1270N.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V and G1069R. In some embodiments, the patient possesses a CFTR genetic mutation selected from G178R, G551S, G970R, G1244E, S1255P, G1349D, S549N, S549R and S1251N. In some embodiments, the patient possesses a CFTR genetic mutation selected from E193K, F1052V and G1069R. In some embodiments, the method produces an increase in chloride transport relative to baseline chloride transport of the patient of the patient.

In some embodiments, in the methods of treating, lessening the severity of, or symptomatically treating cystic fibrosis disclosed herein, the patient possesses a CFTR genetic mutation selected from R117C, D110H, R347H, R352Q, E56K, P67L, L206W, A455E, D579G, S1235R, S945L, R1070W, F1074L, D110E, D1270N and D1152H.

In some embodiments, the patient possesses a CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In some embodiments, the patient possesses a CFTR genetic mutation selected from 1717-1G→A, 1811+1.6kbA→G, 2789+5G→A, 3272-26A→G and 3849+10kbC→T. In some embodiments, the patient possesses a CFTR genetic mutation selected from 2789+5G→A and 3272-26A→G.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and human CFTR mutations selected from F508del, R117H, and G551D.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, 621+3A→G, and a CFTR mutation selected from F508del, R117H, and G551D; and a CFTR mutations selected from F508del, R117H, and G551D.

In some embodiments, the patient possesses a CFTR genetic mutation selected from G178R, G551S, G970R, G1244E, S1255P, G1349D, S549N, S549R, S1251N, E193K, F1052V and G1069R, and a human CFTR mutation selected from F508del, R117H, and G551D. In some embodiments, the patient possesses a CFTR genetic mutation selected from G178R, G551S, G970R, G1244E, S1255P, G1349D, S549N, S549R and S1251N, and a human CFTR mutation selected from F508del, R117H, and G551D.

In some embodiments, the patient possesses a CFTR genetic mutation selected from E193K, F1052V and G1069R, and a human CFTR mutation selected from F508del, R117H, and G551D.

In some embodiments, the patient possesses a CFTR genetic mutation selected from R117C, D110H, R347H, R352Q, E56K, P67L, L206W, A455E, D579G, S1235R, S945L, R1070W, F1074L, D110E, D1270N and D1152H, and a human CFTR mutation selected from F508del, R117H, and G551D.

In some embodiments, the patient possesses a CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D. In some embodiments, the patient possesses a CFTR genetic mutation selected from 1717-1G→A, 1811+1.6kbA→G, 2789+5G→A, 3272-26A→G and 3849+10kbC→T, and a human CFTR mutation selected from F508del, R117H, and G551D. In some embodiments, the patient possesses a CFTR genetic mutation selected from 2789+5G→A and 3272-26A→G, and a human CFTR mutation selected from F508del, R117H.

In some embodiments, the patient is heterozygous having a CF-causing mutation on one allele and a CF-causing mutation on the other allele. In some embodiments, the patient is heterozygous for F508del, and the other CFTR genetic mutation is any CF-causing mutation, including, but not limited to F508del on one CFTR allele and a CFTR mutation on the second CFTR allele that is associated with minimal CFTR function, residual CFTR function, or a defect in CFTR channel gating activity.

In some embodiments, the CF-causing mutation is selected from Table A. In some embodiments, the CF-causing mutation is selected from Table B. In some embodiments, the CF-causing mutation is selected from Table C. In some embodiments, the CF-causing mutation is selected from FIG. 3. In some embodiments, the patient is heterozygous having a CF-causing mutation on one CFTR allele selected from the mutations listed in the table from FIG. 3 and a CF-causing mutation on the other CFTR allele is selected from the CFTR mutations listed in Table B:

TABLE B

CFTR Mutations

| | | |
|---|---|---|
| Q39X | 621+1G→T | A559T |
| W57X | 1248+1G→A | R560T |
| E60X | 1341+1G→A | R560S |
| R75X | 1717-1G→A | A561E |
| E92X | 1811+1.6kbA→G | Y569D |
| Q98X | 1811+1G→C | L1065P |
| Y122X | 1812-1G→A | R1066C |
| L218X | 1898+1G→A | R1066M |
| Q220X | 2622+1G→A | L1077P |
| C276X | 3120+1G→A | H1085R |
| Q290X | 3120G→A | M1101K |
| G330X | 3850-1G→A | N1303K |
| W401X | 4005+1G→A | 3849+10kbC→T |
| Q414X | 4374+1G→T | 3272-26A→G |
| S434X | 663delT | 711+3A→G |
| S466X | 2183AA→G | E56K |
| S489X | CFTRdel2,3 | P67L |
| Q493X | 3659delC | R74W |
| W496X | 394delTT | D110E |
| Q525X | 2184insA | D110H |
| G542X | 3905insT | R117C |
| Q552X | 2184delA | L206W |
| R553X | 1078delT | R347H |
| E585X | 1154insTC | R352Q |
| G673X | 2183delAA→G | A455E |
| R709X | 2143delT | D579G |
| K710X | 1677delTA | E831X |
| L732X | 3876delA | S945L |
| R764X | 2307insA | S977F |
| R785X | 4382delA | F1052V |
| R792X | 4016insT | R1070W |
| E822X | 2347delG | F1074L |
| W846X | 3007delG | D1152H |
| R851X | 574delA | D1270N |
| Q890X | 2711delT | G178R |
| S912X | 3791delC | S549N |
| W1089X | CFTRdele22-23 | S549R |
| Y1092X | 457TAT→G | G551D |
| E1104X | 2043delG | G551S |
| R1158X | 2869insG | G1244E |
| R1162X | 3600+2insT | S1251N |
| S1196X | 3737delA | S1255P |
| W1204X | 4040delA | G1349D |
| S1255X | 541delC | |
| W1282X | A46D | |
| Q1313X | T338I | |
| 621+1G→T | R347P | |
| 711+1G→T | L927P | |
| 711+5G→A | G85E | |
| 712-1G→T | S341P | |
| 405+1G→A | L467P | |
| 405+3A→C | I507del | |
| 406-1G→A | V520F | |

TABLE C

CFTR Mutations

| Criteria | Mutation | | | | |
|---|---|---|---|---|---|
| Truncation mutations % PI > 50% and/or SwCl⁻ > 86 mmol/L No full-length protein | Q2X | L218X | Q525X | R792X | E1104X |
| | S4X | Q220X | G542X | E822X | W1145X |
| | W19X | Y275X | G550X | W882X | R1158X |
| | G27X | C276X | Q552X | W846X | R1162X |
| | Q39X | Q290X | R553X | Y849X | S1196X |
| | W57X | G330X | E585X | R851X | W1204X |
| | E60X | W401X | G673X | Q890X | L1254X |
| | R75X | Q414X | Q685X | S912X | S1255X |
| | L88X | S434X | R709X | Y913X | W1282X |
| | E92X | S466X | K710X | Q1042X | Q1313X |
| | Q98X | S489X | Q715X | W1089X | Q1330X |
| | Y122X | Q493X | L732X | Y1092X | E1371X |
| | E193X | W496X | R764X | W1098X | Q1382X |
| | W216X | C524X | R785X | R1102X | Q1411X |

TABLE C-continued

CFTR Mutations

| Criteria | Mutation | | | | |
|---|---|---|---|---|---|
| Splice mutations | 185+1G→T | 711+5G→A | 1717-8G→A | 2622+1G→A | 3121-1G→A |
| % PI > 50% | 296+1G→A | 712-1G→T | 1717-1G→A | 2790-1G→C | 3500-2A→G |
| and/or | 296+1G→T | 1248+1G→A | 1811+1G→C | 3040G→C | 3600+2insT |
| SwCl⁻ > 86 | 405+1G→A | 1249-1G→A | 1811+1.6kbA→G | (G970R) | 3850-1G→A |
| mmol/L | 405+3A→C | 1341+1G→A | 1811+1643G→T | 3120G→A | 4005+1G→A |
| No or little | 406-1G→A | 1525-2A→G | 1812-1G→A | 3120+1G→A | 4374+1G→T |
| mature mRNA | 621+1G→T | 1525-1G→A | 1898+1G→A | 3121-2A→G | |
| | 711+1G→T | | 1898+1G→C | | |
| Small (≤3 | 182delT | 1078delT | 1677delTA | 2711delT | 3737delA |
| nucleotide) | 306insA | 1119delA | 1782delA | 2732insA | 3791delC |
| insertion/deletion | 306delTAGA | 1138insG | 1824delA | 2869insG | 3821delT |
| (ins/del) frameshift | 365-366insT | 1154insTC | 1833delT | 2896insAG | 3876delA |
| mutations | 394delTT | 1161delC | 2043delG | 2942insT | 3878delG |
| % PI > 50% | 442delA | 1213delT | 2143delT | 2957delT | 3905insT |
| and/or | 444delA | 1259insA | 2183AA→G ᵃ | 3007delG | 4016insT |
| SwCl⁻ > 86 | 457TAT→G | 1288insTA | 2184delA | 3028delA | 4021dupT |
| mmol/L | 541delC | 1343delG | 2184insA | 3171delC | 4022insT |
| Garbled and/or | 574delA | 1471delA | 2307insA | 3171insC | 4040delA |
| truncated | 663delT | 1497delGG | 2347delG | 3271delGG | 4279insA |
| protein | 849delG | 1548delG | 2585delT | 3349insT | 4326delTC |
| | 935delA | 1609del CA | 2594delGT | 3659delC | |
| Non-small (>3 | CFTRdele1 | CFTRdele16-17b | | 1461ins4 | |
| nucleotide) | CFTRdele2 | CFTRdele17a, 17b | | 1924del7 | |
| insertion/deletion | CFTRdele2, 3 | CFTRdele17a-18 | | 2055del9→A | |
| (ins/del) frameshift | CFTRdele2-4 | CFTRdele19 | | 2105-2117del13insAGAAA | |
| mutations | | | | | |
| % PI > 50% and/or | CFTRdele3-10, 14b-16 | CFTRdele19-21 | | 2372del8 | |
| SwCl⁻ > 86 | CFTRdele4-7 | CFTRdele21 | | 2721del11 | |
| mmol/L | CFTRdele4-11 | CFTRdele22-24 | | 2991del32 | |
| Garbled and/or | CFTR50kbdel | CFTRdele22, 23 | | 3121-977_3499+248del2515 | |
| truncated | CFTRdup6b-10 | 124del23bp | | 3667ins4 | |
| protein | CFTRdele11 | 602del14 | | 4010del4 | |
| | CFTRdele13, 14a | 852del22 | | 4209TGTT→AA | |
| | CFTRdele14b-17b | 991del5 | | | |
| Class II, III, IV | A46Dᵇ | V520F | Y569Dᵇ | N1303K | |
| mutations not | G85E | A559Tᵇ | L1065P | | |
| responsive to | R347P | R560T | R1066C | | |
| Compound II, | L467Pᵇ | R560S | L1077Pᵇ | | |
| Compound III, | I507del | A561E | M1101K | | |
| or Compound II/ | | | | | |
| Compound III | | | | | |
| % PI > 50% and/or | | | | | |
| SwCl⁻ > 86 | | | | | |
| mmol/L | | | | | |
| AND | | | | | |
| Not responsive | | | | | |
| in vitro to | | | | | |
| Compound II, | | | | | |
| Compound III, | | | | | |
| or Compound II/ | | | | | |
| Compound III | | | | | |

CFTR: cyctic fibrosis transmembrane conductance regulator; SwCl: sweat chloride
Source: CFTR2.org [Internet]. Baltimore (MD): Clinical and functional translation of CFTR. The Clinical and Functional Translation of CFTR (CFTR2), US Cystic Fibrosis Foundation, Johns Hopkins University, the Hospital for Sick Children. Available at: http://www.cftr2.org/. Accessed 15 Feb. 2016.
Notes:
% PI: percentage of F508del-CFTR heterozygous patients in the CFTR2 patient registry who are pancreatic insufficient; SwCl: mean sweat chloride of F508del-CFTR heterozygous patients in the CFTR2 patient registry.
ᵃ Also known as 2183delAA→G.
ᵇUnpublished data.

In some embodiments, the patient is: with F508del/MF (F/MF) genotypes (heterozygous for F508del and an MF mutation not expected to respond to CFTR modulators, such as Compound III); with F508del/F508del (F/F) genotype (homozygous for F508del); and/or with F508del/gating (F/G) genotypes (heterozygous for F508del and a gating mutation known to be CFTR modulator-responsive (e.g., Compound III-responsive). In some embodiments, the patient with F508del/MF (F/MF) genotypes has a MF mutation that is not expected to respond to Compound II, Compound III, and both of Compound II and Compound III. In some embodiments, the patient with F508del/MF (F/MF) genotypes has any one of the MF mutations in Table C.

In some embodiments, the patient is heterozygous for F508del, and the other CFTR genetic mutation is any CF-causing mutation, including truncation mutations, splice mutations, small (≤3 nucleotide) insertion or deletion (ins/del) frameshift mutations; non-small (>3 nucleotide) insertion or deletion (ins/del) frameshift mutations; and Class II, III, IV mutations not responsive to Compound III alone or in combination with Compound II or Compound IV.

In some embodiments, the patient is heterozygous for F508del, and the other CFTR genetic mutation is a truncation mutation. In some specific embodiments, the truncation mutation is a truncation mutation listed in Table C.

In some embodiments, the patient is heterozygous for F508del, and the other CFTR genetic mutation is a splice mutation. In some specific embodiments, the splice mutation is a splice mutation listed in Table C.

In some embodiments, the patient is heterozygous for F508del, and the other CFTR genetic mutation is a small (≤3 nucleotide) insertion or deletion (ins/del) frameshift mutation. In some specific embodiments, the small (≤3 nucleotide) insertion or deletion (ins/del) frameshift mutation is a small (≤3 nucleotide) insertion or deletion (ins/del) frameshift mutation listed in Table C.

In some embodiments, the patient is heterozygous for F508del, and the other CFTR genetic mutation is any CF-causing mutation expected to be and/or is responsive to, based on in vitro and/or clinical data, any combination of (i) a novel compound chosen from those disclosed herein (e.g., compounds of Formula (I), (II), (III), (IV), or (V), and pharmaceutically acceptable salts thereof, and their deuterated derivatives), and (ii) Compound II, and/or Compound III, and/or Compound IV.

In some embodiments, the patient is heterozygous for F508del, and the other CFTR genetic mutation is any CF-causing mutation expected to be and/or is responsive, based on in vitro and/or clinical data, to the triple combination of a novel compound chosen from those disclosed herein (e.g., compounds of Formula (I), (II), (III), (IV), or (V), and pharmaceutically acceptable salts thereof, and their deuterated derivatives), and Compound II, and Compound III.

In some embodiments, the patient is heterozygous for F508del, and the other CFTR genetic mutation is a non-small (>3 nucleotide) insertion or deletion (ins/del) frameshift mutation. In some specific embodiments, the non-small (>3 nucleotide) insertion or deletion (ins/del) frameshift mutation is a non-small (>3 nucleotide) insertion or deletion (ins/del) frameshift mutation listed in Table 5B.

In some embodiments, the patient is heterozygous for F508del, and the other CFTR genetic mutation is a Class II, III, IV mutations not responsive to Compound III alone or in combination with Compound II or Compound IV. In some specific embodiments, the Class II, III, IV mutations not responsive to Compound III alone or in combination with Compound II or Compound IV is a Class II, III, IV mutations not responsive to Compound III alone or in combination with Compound II or Compound IV listed in Table C.

In some embodiments, the patient is heterozygous for F508del, and the other CFTR genetic mutation is any mutation listed in Table C.

In some embodiments, the patient is heterozygous for F508del, and the other CFTR genetic mutation is any mutation, but other than F508del, listed in Table A, B, C, and FIG. 3.

In some embodiments, the patient is heterozygous for F508del, and the other CFTR genetic mutation is any mutation listed in Table A. In some embodiments, the patient is heterozygous for F508del, and the other CFTR genetic mutation is any mutation listed in Table B. In some embodiments, the patient is heterozygous for F508del, and the other CFTR genetic mutation is any mutation listed in Table C. In some embodiments, the patient is heterozygous for F508del, and the other CFTR genetic mutation is any mutation listed in FIG. 3.

In some embodiments, the patient is homozygous for F508del.

In some embodiments, the patient is heterozygous having one CF-causing mutation on one CFTR allele selected from the mutations listed in the table from FIG. 3 and another CF-causing mutation on the other CFTR allele is selected from the CFTR mutations listed in Table C.

In some embodiments, the composition disclosed herein is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected for patients that are heterozygous or homozygous for a variety of different mutations, including patients heterozygous for the most common mutation, F508del, as well as other mutations such as the G551D mutation, or the R117H mutation. In some embodiments, compositions disclosed herein are useful for treating, lessening the severity of, or symptomatically treating cystic fibrosis in patients who exhibit little to no residual CFTR activity. In some embodiments, compositions disclosed herein are useful for treating, lessening the severity of, or symptomatically treating cystic fibrosis in patients who exhibit little to no residual CFTR activity in the apical membrane of respiratory epithelia.

In some embodiments, the compositions disclosed herein are useful for treating or lessening the severity of cystic fibrosis in patients who exhibit residual CFTR activity using pharmacological methods. Such methods increase the amount of CFTR present at the cell surface, thereby inducing a hitherto absent CFTR activity in a patient or augmenting the existing level of residual CFTR activity in a patient.

In some embodiments, the compositions disclosed herein are useful for treating or lessening the severity of cystic fibrosis in patients with certain genotypes exhibiting residual CFTR activity.

In some embodiments, compositions disclosed herein are useful for treating, lessening the severity of, or symptomatically treating cystic fibrosis in patients within certain clinical phenotypes, e.g., a mild to moderate clinical phenotype that typically correlates with the amount of residual CFTR activity in the apical membrane of epithelia. Such phenotypes include patients exhibiting pancreatic sufficiency.

In some embodiments, the compositions disclosed herein are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In some embodiments, this disclosure relates to a method of augmenting or inducing anion channel activity in vitro or in vivo, comprising contacting the channel with a composition disclosed herein. In some embodiments, the anion channel is a chloride channel or a bicarbonate channel. In some embodiments, the anion channel is a chloride channel.

In some embodiments of the methods of treating cystic fibrosis disclosed herein, the absolute change in patient's percent predicted forced expiratory volume in one second (ppFEV$_1$) after 15 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 3% to 40% relative to the ppFEV1 of the patient prior to said administration.

In some embodiments of the methods of treating cystic fibrosis disclosed herein, the absolute change in patient's percent predicted forced expiratory volume in one second (ppFEV$_1$) after 29 days of administration of at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof ranges from 3% to 40% relative to the ppFEV1 of the patient prior to said administration. In some embodiments, the absolute change ppFEV$_1$ after 29 days ranges from 4% to 40% relative to the ppFEV1 of the patient prior to administration. In some embodiments, the absolute change ppFEV$_1$ after 29 days ranges from 6% to 40% relative to the ppFEV1 of the patient prior to administration. In some embodiments, the absolute change ppFEV$_1$ after 29 days ranges from 7% to 40% relative to the ppFEV1 of the patient prior to administration.

In some embodiments of the methods of treating cystic fibrosis disclosed herein, the absolute change in the patient's sweat chloride after 15 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from −2 to −65 mmol/L from baseline, i.e., relative to the sweat chloride of the patient prior to said administration. In some embodiments, the absolute change in sweat chloride of said patient ranges from −3 to −65 mmol/L. In some embodiments, the absolute change in sweat chloride of said patient ranges from −5 to −65 mmol/L. In some embodiments, the absolute change in sweat chloride of said patient ranges from −10 to −65 mmol/L. In some embodiments, the absolute change in sweat chloride of said patient ranges from −20 to −65 mmol/L. In some embodiments, the absolute change in sweat chloride of said patient ranges from −30 to −65 mmol/L. In some embodiments, the absolute change in sweat chloride of said patient ranges from −38 to −65 mmol/L. In some embodiments of the methods of treating cystic fibrosis disclosed herein, the absolute change in the patient's sweat chloride after 29 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from −2 to −65 mmol/L from baseline, i.e., relative to the sweat chloride of the patient prior to said administration. In some embodiments, the absolute change in sweat chloride of said patient ranges from −3 to −65 mmol/L. In some embodiments, the absolute change in sweat chloride of said patient ranges from −5 to −65 mmol/L. In some embodiments, the absolute change in sweat chloride of said patient ranges from −10 to −65 mmol/L. In some embodiments, the absolute change in sweat chloride of said patient ranges from −20 to −65 mmol/L. In some embodiments, the absolute change in sweat chloride of said patient ranges from −30 to −65 mmol/L. In some embodiments, the absolute change in sweat chloride of said patient ranges from −38 to −65 mmol/L.

In some embodiments of the methods of treating cystic fibrosis disclosed herein, the absolute change in the patient's sweat chloride after 29 days of administration of at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof ranges from −2 to −65 mmol/L from baseline, i.e., relative to the sweat chloride of the patient prior to said administration. In some embodiments, the absolute change in sweat chloride of said patient ranges from −5 to −65 mmol/L. In some embodiments, the absolute change in sweat chloride of said patient ranges from −10 to −65 mmol/L. In some embodiments, the absolute change in sweat chloride of said patient ranges from −2 to −65 mmol/L.

In some embodiments, the triple combinations are administered to a patient who has one F508del mutation and one minimal function mutation, and who has not taken any of said at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof.

In some embodiments, the triple combinations are administered to a patient has two copies of F508del mutation, and wherein patient has taken at least one compound chosen from Compound II and pharmaceutically acceptable salts thereof, and at least one compound chosen from Compound III or III-d and pharmaceutically acceptable salts thereof, but not any of said at least one compound chosen from Compound I and pharmaceutically acceptable salts thereof.

In some embodiments, the absolute change in patient's ppFEV$_1$ after 15 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 3% to 35% relative to the ppFEV1 of the patient prior to said administration.

In some embodiments, the absolute change in patient's ppFEV$_1$ after 29 days of administration of at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof ranges from 3% to 35% relative to the ppFEV1 of the patient prior to said administration.

In some embodiments, the absolute change in a patient's ppFEV$_1$ relative to the ppFEV1 of the patient prior to such administration of the triple combinations can be calculated as (postbaseline value−baseline value). The baseline value is defined as the most recent non-missing measurement collected before the first dose of study drug in the Treatment Period (Day1).

The exact amount of a pharmaceutical composition required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, such as a mammal, and even further such as a human.

In some embodiments, the disclosure also is directed to methods of treatment using isotope-labelled compounds of the afore-mentioned compounds, which, in some embodiments, are referred to as Compound I', Compound II', Compound III', Compound III-d or Compound IV'. In some embodiments, Compound I', Compound II', Compound III', Compound III-d, Compound IV', or pharmaceutically acceptable salts thereof, wherein the formula and variables of such compounds and salts are each and independently as described above or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^2$H, 3H, $^{13}$C, $^{14}$C, $^{15}$N, $^{18}$O, $^{17}$O, $^{31}$P, $^{32}$P, $^{35}$S, $^{18}$F and $^{36}$Cl, respectively.

The isotope-labelled compounds and salts can be used in a number of beneficial ways. They can be suitable for medicaments and/or various types of assays, such as substrate tissue distribution assays. For example, tritium ($^3$H)- and/or carbon-14 ($^{14}$C)-labelled compounds are particularly useful for various types of assays, such as substrate tissue distribution assays, due to relatively simple preparation and excellent detectability. For example, deuterium ($^2$H)-labelled ones are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2$H)-labelled ones. In some specific embodiments, the isotope-labelled compounds and salts are deuterium ($^2$H)-labelled, wherein one or more hydrogen atoms therein have been replaced by deuterium. In chemical structures, deuterium is represented as "D."

The deuterium ($^2$H)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

In some embodiments, Compound III' as used herein includes the deuterated compound disclosed in U.S. Pat. No. 8,865,902 (which is incorporated herein by reference), and CTP-656.

In some embodiments, Compound III' is:

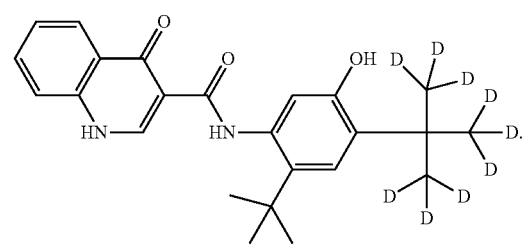

Exemplary embodiments of the disclosure include:

1. A method of treating cystic fibrosis comprising administering to a patient in need thereof:

(A) 10 mg to 900 mg of at least one compound chosen from Compound I

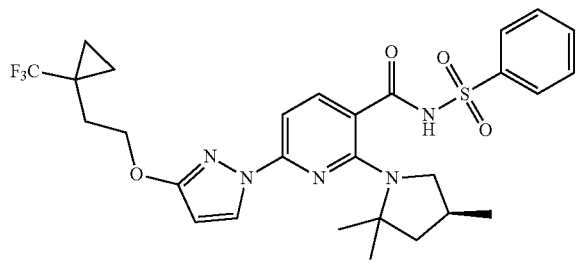 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

and pharmaceutically acceptable salts thereof daily; and
(B) at least one compound chosen from: (i) Compound II:

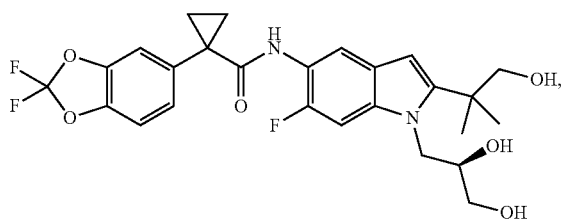 [SMILES: CC(C)(CO)c1cc2cc(NC(=O)C3(c4ccc5c(c4)OC(F)(F)O5)CC3)c(F)cc2n1C[C@@H](O)CO]

and
(ii) Compound III or Compound III-d:

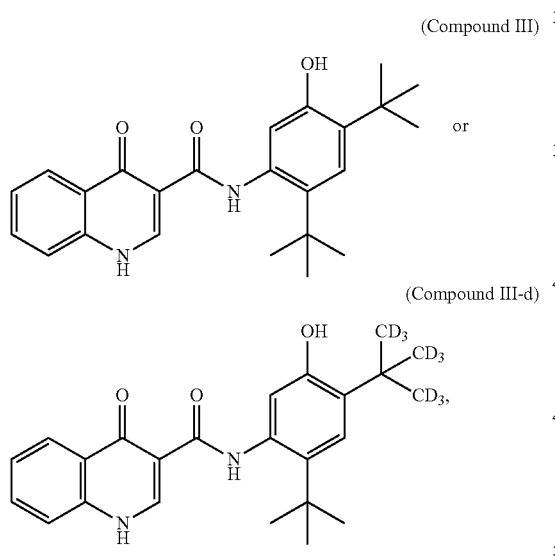

and
(iii) Compound IV:

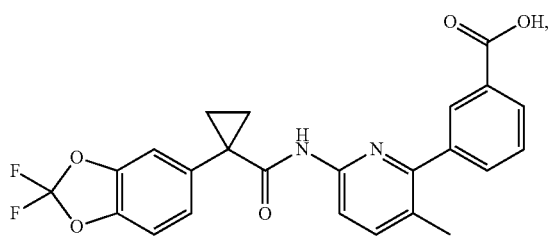 [SMILES: Cc1ccc(NC(=O)C2(c3ccc4c(c3)OC(F)(F)O4)CC2)nc1-c1cccc(C(=O)O)c1]

and
pharmaceutically acceptable salts of any of the foregoing.

2. The method according to embodiment 1, comprising administering to said patient: at least one compound chosen from Compound I and pharmaceutically acceptable salts thereof; at least one compound chosen from Compound II and pharmaceutically acceptable salts thereof; and at least one compound chosen from (i) Compound III and pharmaceutically acceptable salts thereof, or (ii) Compound III-d and pharmaceutically acceptable salts thereof.

3. The method according to embodiment 1, comprising administering to said patient: at least one compound chosen from Compound I and pharmaceutically acceptable salts thereof; at least one compound chosen from Compound II and pharmaceutically acceptable salts thereof; and at least one compound chosen from Compound IV and pharmaceutically acceptable salts thereof.

4. The method according to embodiment 1, comprising administering to said patient: at least one compound chosen from Compound I and pharmaceutically acceptable salts thereof; at least one compound chosen from (i) Compound III and pharmaceutically acceptable salts thereof, or (ii) Compound III-d and pharmaceutically acceptable salts thereof; and at least one compound chosen from Compound IV and pharmaceutically acceptable salts thereof.

5. The method of according to embodiment 1, comprising administering to said patient: (i) at least one compound chosen from Compound I and pharmaceutically acceptable salts thereof; and at least one compound chosen from Compound II and pharmaceutically acceptable salts thereof; (ii) at least one compound chosen from Compound I and pharmaceutically acceptable salts thereof; and at least one compound chosen from (a) Compound III and pharmaceutically acceptable salts thereof, or (b) Compound III-d and pharmaceutically acceptable salts thereof; or (iii) at least one compound chosen from Compound I and pharmaceutically acceptable salts thereof; and at least one compound chosen from Compound IV and pharmaceutically acceptable salts thereof.

6. The method according to any one of embodiments 1-5, wherein 20 mg to 800 mg of at least one compound chosen from Compound I and pharmaceutically acceptable salts thereof is administered daily.

7. The method according to any one of embodiments 1-5, wherein 30 mg to 720 mg of at least one compound chosen from Compound I and pharmaceutically acceptable salts thereof is administered daily.

8. The method according to any one of embodiments 1-5, wherein 40 mg to 600 mg of at least one compound chosen from Compound I and pharmaceutically acceptable salts thereof is administered daily.

9. The method according to any one of embodiments 1-5, wherein 60 mg to 100 mg or 60 mg to 400 mg of at least one compound chosen from Compound I and pharmaceutically acceptable salts thereof is administered daily.

10. The method according to any one of embodiments 1-5, wherein 60 mg to 500 mg of at least one compound chosen from Compound I and pharmaceutically acceptable salts thereof is administered daily.

11. The method according to any one of embodiments 1-5, wherein 80 mg to 400 mg of at least one compound chosen from Compound I and pharmaceutically acceptable salts thereof is administered daily.

12. The method according to any one of embodiments 1-5, wherein 120 mg to 200 or 120 mg to 450 mg of at least one compound chosen from Compound I and pharmaceutically acceptable salts thereof is administered daily.

13. The method according to any one of embodiments 1-5, wherein 120 mg to 360 or 120 mg to 500 mg of at least one compound chosen from Compound I and pharmaceutically acceptable salts thereof is administered daily.
14. The method according to any one of embodiments 1-5, wherein 160 mg to 320 or 160 mg to 450 mg of at least one compound chosen from Compound I and pharmaceutically acceptable salts thereof is administered daily.
15. The method according to any one of embodiments 1-5, wherein 240 mg to 400 mg of at least one compound chosen from Compound I and pharmaceutically acceptable salts thereof is administered daily.
16. The method according to any one of embodiments 1-5, wherein 320 mg to 480 mg of at least one compound chosen from Compound I and pharmaceutically acceptable salts thereof is administered daily.
17. The method according to any one of embodiments 1-5, wherein 360 mg to 640 mg of at least one compound chosen from Compound I and pharmaceutically acceptable salts thereof is administered daily.
18. The method according to any one of embodiments 1-5, wherein 380 mg to 420 mg of at least one compound chosen from Compound I and pharmaceutically acceptable salts thereof is administered daily.
19. The method according to any one of embodiments 1-5, wherein 160 mg to 420 mg of at least one compound chosen from Compound I and pharmaceutically acceptable salts thereof is administered daily.
20. The method according to any one of embodiments 1-5, wherein 320 mg to 420 mg of at least one compound chosen from Compound I and pharmaceutically acceptable salts thereof is administered daily.
21. The method according to any one of embodiments 1-5, wherein 400 mg of at least one compound chosen from Compound I and pharmaceutically acceptable salts thereof is administered daily.
22. The method according to any one of embodiments 1-5, wherein 400 mg or 720 mg of at least one compound chosen from Compound I and pharmaceutically acceptable salts thereof is administered daily.
23. The method according to any one of embodiments 1-22, wherein at least one compound chosen from Compound I and pharmaceutically acceptable salts thereof is administered as a single dose, once daily.
24. The method according to any one of embodiments 1-22, wherein at least one compound chosen from Compound I and pharmaceutically acceptable salts thereof is administered in two doses daily.
25. The method according to any one of embodiments 1-3, and 5, wherein 25 mg to 200 mg of at least one compound chosen from Compound II and pharmaceutically acceptable salts thereof is administered daily.
26. The method according to any one of embodiments 1-3, and 5, wherein 50 mg to 150 mg of at least one compound chosen from Compound II and pharmaceutically acceptable salts thereof is administered daily.
27. The method according to any one of embodiments 1-3, and 5, wherein 75 mg to 200 mg of at least one compound chosen from Compound II and pharmaceutically acceptable salts thereof is administered daily.
28. The method according to any one of embodiments 1-3, and 5, wherein 50 mg of at least one compound chosen from Compound II and pharmaceutically acceptable salts thereof is administered daily.
29. The method according to any one of embodiments 1-3, and 5, wherein 100 mg of at least one compound chosen from Compound II and pharmaceutically acceptable salts thereof is administered daily.
30. The method according to any one of embodiments 1-3, 5, and 25-29, wherein at least one compound chosen from Compound II and pharmaceutically acceptable salts thereof is administered as a single dose, once daily.
31. The method according to any one of embodiments 1-3, 5, and 25-29, wherein at least one compound chosen from Compound II and pharmaceutically acceptable salts thereof is administered in two doses daily.
32. The method according to any one of embodiments 1, 2, 4, and 5, wherein: (i) 50 mg to 600 mg of at least one compound chosen from Compound III and pharmaceutically acceptable salts thereof is administered daily; or (ii) 50 mg to 600 mg of at least one compound chosen from Compound III-d and pharmaceutically acceptable salts thereof is administered daily.
33. The method according to any one of embodiments 1, 2, 4, and 5, wherein: (i) 50 mg to 450 mg of at least one compound chosen from Compound III and pharmaceutically acceptable salts thereof is administered daily; or (ii) 50 mg to 450 mg of at least one compound chosen from Compound III-d and pharmaceutically acceptable salts thereof is administered daily.
34. The method according to any one of embodiments 1, 2, 4, and 5, wherein: (i) 100 mg to 400 mg of at least one compound chosen from Compound III and pharmaceutically acceptable salts thereof is administered daily; or (ii) 100 mg to 400 mg of at least one compound chosen from Compound III-d and pharmaceutically acceptable salts thereof is administered daily.
35. The method according to any one of embodiments 1, 2, 4, and 5, wherein: (i) 125 mg to 300 mg at least one compound chosen from Compound III and pharmaceutically acceptable salts thereof is administered daily; or (ii) 125 mg to 300 mg at least one compound chosen from Compound III-d and pharmaceutically acceptable salts thereof is administered daily.
36. The method according to any one of embodiments 1, 2, 4, and 5, wherein: (i) 150 mg to 300 mg of at least one compound chosen from Compound III and pharmaceutically acceptable salts thereof is administered daily; or (ii) 150 mg to 300 mg of at least one compound chosen from Compound III-d and pharmaceutically acceptable salts thereof is administered daily.
37. The method according to any one of embodiments 1, 2, 4, and 5, wherein: (i) 200 mg to 600 mg of at least one compound chosen from Compound III and pharmaceutically acceptable salts thereof is administered daily; or (ii) 100 mg to 300 mg of at least one compound chosen from Compound III-d and pharmaceutically acceptable salts thereof is administered daily.
38. The method according to any one of embodiments 1, 2, 4, and 5, wherein: (i) 300 mg or 600 mg of at least one compound chosen from Compound III and pharmaceutically acceptable salts thereof is administered daily; or (ii) 150 mg, 200 mg, or 300 mg of at least one compound chosen from Compound III-d and pharmaceutically acceptable salts thereof is administered daily.
39. The method according to any one of embodiments 1, 2, 4, and 5, wherein: (i) 150 mg of at least one compound chosen from Compound III and pharmaceutically acceptable salts thereof is administered twice daily; or (ii) 150 mg, 200 mg, or 300 mg of at least one compound chosen from Compound III-d and pharmaceutically acceptable salts thereof is administered once daily.

40. The method according to any one of embodiments 1, 2, 4, 5, and 32-38, wherein at least one compound chosen from Compound III or Compound III-d and pharmaceutically acceptable salts thereof is administered as a single dose, once daily.
41. The method according to any one of embodiments 1, 2, 4, 5, and 32-38, wherein the dose of at least one compound chosen from Compound III or Compound III-d and pharmaceutically acceptable salts thereof is administered in two doses daily.
42. The method according to any one of embodiments 1, 3, 4, and 5, wherein 100 mg to 1,000 mg of at least one compound chosen from Compound IV and pharmaceutically acceptable salts thereof is administered daily.
43. The method according to any one of embodiments 1, 3, 4, and 5, wherein 400 mg to 1,000 mg of at least one compound chosen from Compound IV and pharmaceutically acceptable salts thereof is administered daily.
44. The method according to any one of embodiments 1, 3, 4, and 5, wherein 800 mg of at least one compound chosen from Compound IV and pharmaceutically acceptable salts thereof is administered daily.
45. The method according to any one of embodiments 1, 3, 4, 5, and 41-44, wherein 400 mg of at least one compound chosen from Compound IV and pharmaceutically acceptable salts thereof is administered twice daily.
46. The method according to any one of embodiments 1, 3, 4, 5, and 41-44, wherein the dose of at least one compound chosen from Compound IV and pharmaceutically acceptable salts thereof is administered as a single dose daily or as two doses daily.
47. The method according to embodiment 1, wherein said patient has cystic fibrosis is chosen from patients with F508del/minimal function genotypes, patients with F508del/F508del genotypes, patients with F508del/gating genotypes, patients with F508del/residual function genotypes, and patients with F508del/another CFTR genetic mutation that is expected to be and/or is responsive to the triple combination of Compound I, Compound II, and Compound III genotypes based on in vitro and/or clinical data.
48. The method according to embodiment 1, wherein 80 mg to 600 mg of at least one compound chosen from Compound I and pharmaceutically acceptable salts thereof is administered daily.
49. The method according to embodiment 1, wherein: (i) 50 mg to 200 mg of at least one compound chosen from Compound II and pharmaceutically acceptable salts thereof is administered daily; and/or 150 mg to 600 mg of at least one compound chosen from Compound III and pharmaceutically acceptable salts thereof is administered daily; or (ii) 50 mg to 200 mg of at least one compound chosen from Compound II and pharmaceutically acceptable salts thereof is administered daily; and/or 100 mg to 400 mg of at least one compound chosen from Compound III-d and pharmaceutically acceptable salts thereof is administered daily.
50. The method according to any one of embodiments 1, 48, and 49, wherein: (i) wherein 150 mg to 600 mg of at least one compound chosen from Compound III and pharmaceutically acceptable salts thereof; and/or 400 mg to 1,000 mg of at least one compound chosen from Compound IV and pharmaceutically acceptable salts thereof is administered daily; or (ii) 100 mg to 300 mg of at least one compound chosen from Compound III-d and pharmaceutically acceptable salts thereof; and/or 400 mg to 1,000 mg of at least one compound chosen from Compound IV and pharmaceutically acceptable salts thereof is administered daily.

51. A method of treating cystic fibrosis comprising administering daily to a patient in need thereof a pharmaceutical composition comprising:

(A) 10 mg to 900 mg at least one compound chosen from Compound I

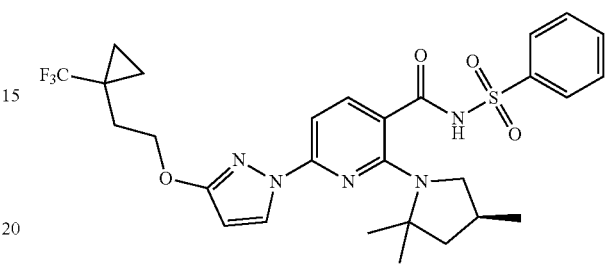

and pharmaceutically acceptable salts thereof;

(B) at least one compound chosen from: (i) Compound II:

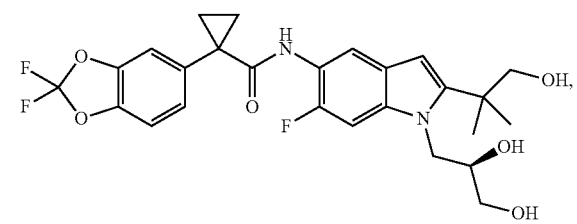 [SMILES: CC(C)(CO)c1cc2cc(NC(=O)C3(c4ccc5c(c4)OC(F)(F)O5)CC3)c(F)cc2n1C[C@@H](O)CO]

(ii) Compound III or Compound III-d:

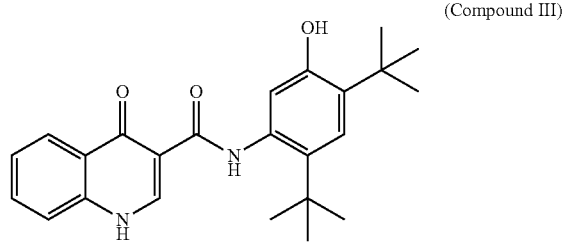

(Compound III)

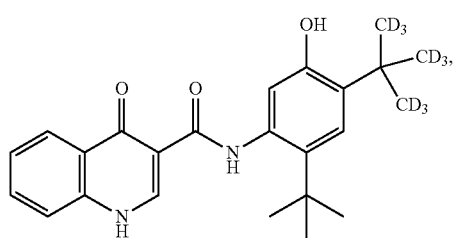

(Compound III-d)

and
(iii) Compound IV:

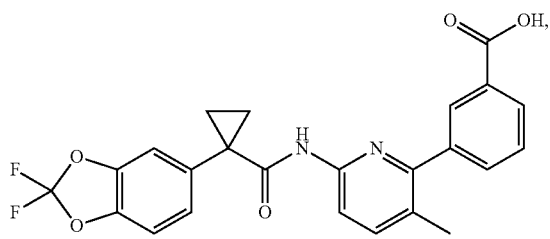 [SMILES: Cc1ccc(NC(=O)C2(c3ccc4c(c3)OC(F)(F)O4)CC2)nc1-c1cccc(C(=O)O)c1]

and pharmaceutically acceptable salts any of the foregoing; and (C) a pharmaceutically acceptable carrier.

52. The method according to embodiment 51, wherein: (i) the pharmaceutical composition comprises: at least one compound chosen from Compound I and pharmaceutically acceptable salts thereof; at least one compound chosen from Compound II and pharmaceutically acceptable salts thereof; and at least one compound chosen from Compound III and pharmaceutically acceptable salts thereo; or (ii) the pharmaceutical composition comprises: at least one compound chosen from Compound I and pharmaceutically acceptable salts thereof; at least one compound chosen from Compound II and pharmaceutically acceptable salts thereof; and at least one compound chosen from Compound III-d and pharmaceutically acceptable salts thereof.

53. The method according to embodiment 51, wherein the pharmaceutical composition comprises: at least one compound chosen from Compound I and pharmaceutically acceptable salts thereof; at least one compound chosen from Compound II and pharmaceutically acceptable salts thereof; and at least one compound chosen from Compound IV and pharmaceutically acceptable salts thereof.

54. The method according to embodiment 51, wherein: (i) the pharmaceutical composition comprises: at least one compound chosen from Compound I and pharmaceutically acceptable salts thereof; at least one compound chosen from Compound III and pharmaceutically acceptable salts thereof; and at least one compound chosen from Compound IV and pharmaceutically acceptable salts thereof; or (ii) the pharmaceutical composition comprises: at least one compound chosen from Compound I and pharmaceutically acceptable salts thereof; at least one compound chosen from Compound III-d and pharmaceutically acceptable salts thereof; and at least one compound chosen from Compound IV and pharmaceutically acceptable salts thereof.

55. The method of according to embodiment 51, wherein the pharmaceutical composition comprises: (A) (i) at least one compound chosen from Compound I and pharmaceutically acceptable salts thereof; and at least one compound chosen from Compound II and pharmaceutically acceptable salts thereof; (ii) at least one compound chosen from Compound I and pharmaceutically acceptable salts thereof; and at least one compound chosen from Compound III and pharmaceutically acceptable salts thereof; or (iii) at least one compound chosen from Compound I and pharmaceutically acceptable salts thereof; and at least one compound chosen from Compound IV and pharmaceutically acceptable salts thereof; or (B) (i) at least one compound chosen from Compound I and pharmaceutically acceptable salts thereof; and at least one compound chosen from Compound II and pharmaceutically acceptable salts thereof; (ii) at least one compound chosen from Compound I and pharmaceutically acceptable salts thereof; and at least one compound chosen from Compound III-d and pharmaceutically acceptable salts thereof; or (iii) at least one compound chosen from Compound I and pharmaceutically acceptable salts thereof; and at least one compound chosen from Compound IV and pharmaceutically acceptable salts thereof.

56. The method according to any one of embodiments 51-55, wherein 20 mg to 800 mg of at least one compound chosen from Compound I and pharmaceutically acceptable salts thereof is administered daily.

57. The method according to any one of embodiments 51-55, wherein 30 mg to 720 mg of at least one compound chosen from Compound I and pharmaceutically acceptable salts thereof is administered daily.

58. The method according to any one of embodiments 51-55, wherein 40 mg to 600 mg of at least one compound chosen from Compound I and pharmaceutically acceptable salts thereof is administered daily.

59. The method according to any one of embodiments 51-55, wherein 60 mg to 400 mg of at least one compound chosen from Compound I and pharmaceutically acceptable salts thereof is administered daily.

60. The method according to any one of embodiments 51-55, wherein 60 mg to 500 mg of at least one compound chosen from Compound I and pharmaceutically acceptable salts thereof is administered daily.

61. The method according to any one of embodiments 51-55, wherein 80 mg to 400 mg of at least one compound chosen from Compound I and pharmaceutically acceptable salts thereof is administered daily.

62. The method according to any one of embodiments 51-55, wherein 120 mg to 450 mg of at least one compound chosen from Compound I and pharmaceutically acceptable salts thereof is administered daily.

63. The method according to any one of embodiments 51-55, wherein 120 mg to 500 mg of at least one compound chosen from Compound I and pharmaceutically acceptable salts thereof is administered daily.

64. The method according to any one of embodiments 51-55, wherein 160 mg to 450 mg of at least one compound chosen from Compound I and pharmaceutically acceptable salts thereof is administered daily.

65. The method according to any one of embodiments 51-55, wherein 240 mg to 400 mg of at least one compound chosen from Compound I and pharmaceutically acceptable salts thereof is administered daily.

66. The method according to any one of embodiments 51-55, wherein 320 mg to 480 mg of at least one compound chosen from Compound I and pharmaceutically acceptable salts thereof is administered daily.

67. The method according to any one of embodiments 51-55, wherein 360 mg to 640 mg of at least one compound chosen from Compound I and pharmaceutically acceptable salts thereof is administered daily.

68. The method according to any one of embodiments 51-55, wherein 380 mg to 420 mg of at least one compound chosen from Compound I and pharmaceutically acceptable salts thereof is administered daily.

69. The method according to any one of embodiments 51-55, wherein 160 mg to 420 mg of at least one compound chosen from Compound I and pharmaceutically acceptable salts thereof is administered daily.

70. The method according to any one of embodiments 51-55, wherein 320 mg to 420 mg of at least one compound chosen from Compound I and pharmaceutically acceptable salts thereof is administered daily.

71. The method according to any one of embodiments 51-55, wherein 400 mg of at least one compound chosen from Compound I and pharmaceutically acceptable salts thereof is administered daily.

72. The method according to any one of embodiments 51-55, wherein 480 mg or 720 mg of at least one compound chosen from Compound I and pharmaceutically acceptable salts thereof is administered daily.

73. The method according to any one of embodiments 51, 53, and 55, wherein 25 mg to 200 mg of at least one compound chosen from Compound II and pharmaceutically acceptable salts thereof is administered daily.

74. The method according to any one of embodiments 51, 53, and 55, wherein 50 mg to 150 mg of at least one compound chosen from Compound II and pharmaceutically acceptable salts thereof is administered daily.

75. The method according to any one of embodiments 51, 53, and 55, wherein 75 mg to 200 mg of at least one compound chosen from Compound II and pharmaceutically acceptable salts thereof is administered daily.

76. The method according to any one of embodiments 51, 53, and 55, wherein 50 mg of at least one compound chosen from Compound II and pharmaceutically acceptable salts thereof is administered daily.

77. The method according to any one of embodiments 51, 53, and 55, wherein 100 mg of at least one compound chosen from Compound II and pharmaceutically acceptable salts thereof is administered daily.

78. The method according to any one of embodiments 51, 52, 54, and 55, wherein: (i) 50 mg to 600 mg of at least one compound chosen from Compound III and pharmaceutically acceptable salts thereof is administered daily; or (ii) 50 mg to 600 mg of at least one compound chosen from Compound III-d and pharmaceutically acceptable salts thereof is administered daily.

79. The method according to any one of embodiments 51, 52, 54, and 55, wherein: (i) 50 mg to 450 mg of at least one compound chosen from Compound III and pharmaceutically acceptable salts thereof is administered daily; or (ii) 50 mg to 450 mg of at least one compound chosen from Compound III-d and pharmaceutically acceptable salts thereof is administered daily.

80. The method according to any one of embodiments 51, 52, 54, and 55, wherein: (i) 100 mg to 400 mg of at least one compound chosen from Compound III and pharmaceutically acceptable salts thereof is administered daily; or (ii) 100 mg to 400 mg of at least one compound chosen from Compound III-d and pharmaceutically acceptable salts thereof is administered daily.

81. The method according to any one of embodiments 51, 52, 54, and 55, wherein: (i) 125 mg to 300 mg of at least one compound chosen from Compound III and pharmaceutically acceptable salts thereof is administered daily; or (ii) 125 mg to 300 mg of at least one compound chosen from Compound III-d and pharmaceutically acceptable salts thereof is administered daily.

82. The method according to any one of embodiments 51, 52, 54, and 55, wherein: (i) 150 mg to 300 mg of at least one compound chosen from Compound III and pharmaceutically acceptable salts thereof is administered daily; or (ii) 150 mg to 300 mg of at least one compound chosen from Compound III-d and pharmaceutically acceptable salts thereof is administered daily.

83. The method according to any one of embodiments 51, 52, 54, and 55, wherein: (i) 200 mg to 600 mg of at least one compound chosen from Compound III and pharmaceutically acceptable salts thereof is administered daily; or (ii) 100 mg to 300 mg of at least one compound chosen from Compound III-d and pharmaceutically acceptable salts thereof is administered daily.

84. The method according to any one of embodiments 51, 52, 54, and 55, wherein: (i) 300 mg or 600 mg of at least one compound chosen from Compound III and pharmaceutically acceptable salts thereof is administered daily; or (ii) 150 mg, 200 mg, or 300 mg of at least one compound chosen from Compound III-d and pharmaceutically acceptable salts thereof is administered daily.

85. The method according to any one of embodiments 51, 52, 54, and 55, wherein: (i) 150 mg of at least one compound chosen from Compound III and pharmaceutically acceptable salts thereof is administered twice daily; or (ii) 150 mg, 200 mg, or 300 mg of at least one compound chosen from Compound III-d and pharmaceutically acceptable salts thereof is administered once daily.

86. The method according to any one of embodiments 51, 53, 54, and 55, wherein 100 mg to 1,000 mg of at least one compound chosen from Compound IV and pharmaceutically acceptable salts thereof is administered daily.

87. The method according to any one of embodiments 51, 53, 54, and 55, wherein 400 mg to 1,000 mg of at least one compound chosen from Compound IV and pharmaceutically acceptable salts thereof is administered daily.

88. The method according to any one of embodiments 51, 53, 54, and 55, wherein 800 mg of at least one compound chosen from Compound IV and pharmaceutically acceptable salts thereof is administered daily, or 400 mg of at least one compound chosen from Compound IV and pharmaceutically acceptable salts thereof is administered twice daily.

89. The method according to embodiment 51, wherein said patient has cystic fibrosis is chosen from patients with F508del/minimal function genotypes, patients with F508del/F508del genotypes, patients with F508del/gating genotypes, and patients with F508del/residual function genotypes.

90. The method according to embodiment 51, wherein said pharmaceutical composition comprises 80 mg to 600 mg of at least one compound chosen from Compound I and pharmaceutically acceptable salts thereof and is administered daily.

91. The method according to embodiment 90, further wherein: (i) 50 mg to 200 mg of at least one compound chosen from Compound II and pharmaceutically acceptable salts thereof is administered daily; and/or 150 mg to 600 mg of at least one compound chosen from Compound III and pharmaceutically acceptable salts thereof are administered daily; or (ii) 50 mg to 200 mg of at least one compound chosen from Compound II and pharmaceutically acceptable salts thereof is administered daily; and/or 100 mg to 400 mg of at least one compound chosen from Compound III-d and pharmaceutically acceptable salts thereof are administered daily.

92. The method according to any one of embodiments 51, 90, and 91, wherein: (i) 150 mg to 600 mg of at least one compound chosen from Compound III and pharmaceutically acceptable salts thereof; and/or 400 mg to 1,000 mg of at least one compound chosen from Compound IV and pharmaceutically acceptable salts thereof are administered daily; or (ii) 100 mg to 300 mg of at least one compound chosen from Compound III-d and pharmaceutically acceptable salts thereof; and/or 400 mg to 1,000 mg of at least one compound chosen from Compound IV and pharmaceutically acceptable salts thereof are administered daily.

93. A method of treating cystic fibrosis comprising administering to a patient in need thereof:

(A) a first pharmaceutical composition comprising 10 mg to 900 mg of at least one compound chosen from Compound I

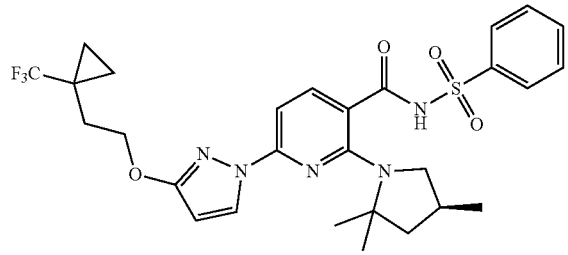 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

and pharmaceutically acceptable salts thereof and a pharmaceutically acceptable carrier, wherein said first pharmaceutical composition is administered daily; and (B) a second pharmaceutical composition comprising at least one compound chosen from (i) Compound II:

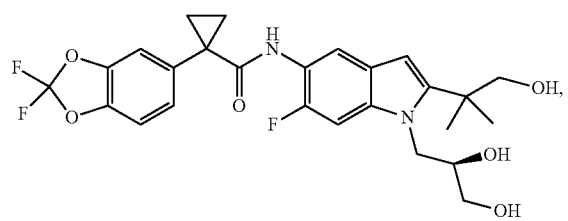 [SMILES: CC(C)(CO)c1cc2cc(NC(=O)C3(c4ccc5c(c4)OC(F)(F)O5)CC3)c(F)cc2n1C[C@@H](O)CO]

and (ii) Compound III or Compound III-d:

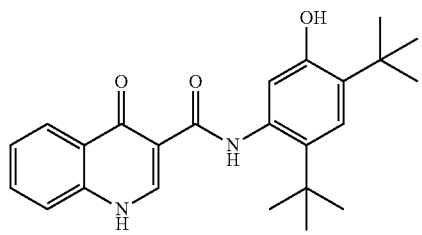
(Compound III)

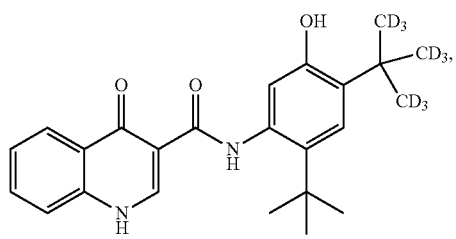
(Compound III-d)

and (iii) Compound IV:

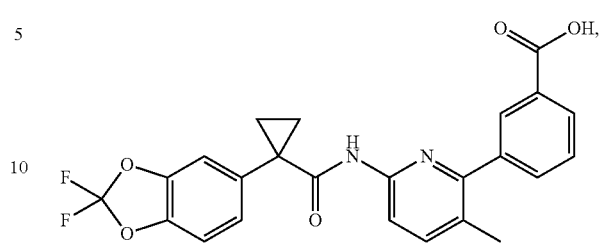

and pharmaceutically acceptable salts of any of the foregoing, and a pharmaceutically acceptable carrier.

94. The method according to embodiment 93, wherein the first pharmaceutical composition comprises: (i) at least one compound chosen from Compound I and pharmaceutically acceptable salts thereof; and the second pharmaceutical composition comprises at least one compound chosen from Compound II and pharmaceutically acceptable salts thereof; and at least one compound chosen from Compound III and pharmaceutically acceptable salts thereof; or (ii) at least one compound chosen from Compound I and pharmaceutically acceptable salts thereof; and the second pharmaceutical composition comprises at least one compound chosen from Compound II and pharmaceutically acceptable salts thereof; and at least one compound chosen from Compound III-d and pharmaceutically acceptable salts thereof.

95. The method according to embodiment 93, wherein the first pharmaceutical composition comprises: at least one compound chosen from Compound I and pharmaceutically acceptable salts thereof; and the second pharmaceutical composition comprises at least one compound chosen from Compound II and pharmaceutically acceptable salts thereof; and at least one compound chosen from Compound IV and pharmaceutically acceptable salts thereof.

96. The method according to embodiment 93, wherein the first pharmaceutical composition comprises: (i) at least one compound chosen from Compound I and pharmaceutically acceptable salts thereof; and the second pharmaceutical composition comprises: at least one compound chosen from Compound III and pharmaceutically acceptable salts thereof; and at least one compound chosen from Compound IV and pharmaceutically acceptable salts thereof; or (ii) at least one compound chosen from Compound I and pharmaceutically acceptable salts thereof; and the second pharmaceutical composition comprises: at least one compound chosen from Compound III-d and pharmaceutically acceptable salts thereof; and at least one compound chosen from Compound IV and pharmaceutically acceptable salts thereof.

97. The method of according to embodiment 93, wherein the first pharmaceutical composition comprises: (a) at least one compound chosen from Compound I and pharmaceutically acceptable salts thereof; and the second pharmaceutical composition comprises: (i) at least one compound chosen from Compound II and pharmaceutically acceptable salts thereof; and at least one compound chosen from Compound III and pharmaceutically acceptable salts thereof; or (ii) at least one compound chosen from Compound II and pharmaceutically acceptable salts thereof; and at least one compound chosen from Compound IV and pharmaceutically acceptable salts thereof; or (b) at least one compound chosen from Compound I and pharmaceutically acceptable salts thereof; and the second pharmaceutical composition comprises: (i) at least one compound chosen from Compound II and pharmaceutically acceptable salts thereof; and at least one compound chosen from Compound III-d and pharmaceutically acceptable salts thereof; or (ii) at least one compound chosen from Compound II and pharmaceutically acceptable salts thereof; and at least one compound chosen from Compound IV and pharmaceutically acceptable salts thereof.

98. The method according to any one of embodiments 93-97, wherein 20 mg to 800 mg of at least one compound chosen from Compound I and pharmaceutically acceptable salts thereof is administered daily.

99. The method according to any one of embodiments 93-97, wherein 30 mg to 720 mg of at least one compound chosen from Compound I and pharmaceutically acceptable salts thereof is administered daily.

100. The method according to any one of embodiments 93-97, wherein 40 mg to 600 mg of at least one compound chosen from Compound I and pharmaceutically acceptable salts thereof is administered daily.

101. The method according to any one of embodiments 93-97, wherein 60 mg to 400 mg of at least one compound chosen from Compound I and pharmaceutically acceptable salts thereof is administered daily.

102. The method according to any one of embodiments 93-97, wherein 60 mg to 500 mg of at least one compound chosen from Compound I and pharmaceutically acceptable salts thereof is administered daily.

103. The method according to any one of embodiments 93-97, wherein 80 mg to 400 mg of at least one compound chosen from Compound I and pharmaceutically acceptable salts thereof is administered daily.

104. The method according to any one of embodiments 93-97, wherein 120 mg to 450 mg of at least one compound chosen from Compound I and pharmaceutically acceptable salts thereof is administered daily.

105. The method according to any one of embodiments 93-97, wherein 120 mg to 500 mg of at least one compound chosen from Compound I and pharmaceutically acceptable salts thereof is administered daily.

106. The method according to any one of embodiments 93-97, wherein 160 mg to 450 mg of at least one compound chosen from Compound I and pharmaceutically acceptable salts thereof is administered daily.

107. The method according to any one of embodiments 93-97, wherein 240 mg to 400 mg of at least one compound chosen from Compound I and pharmaceutically acceptable salts thereof is administered daily.

108. The method according to any one of embodiments 93-97, wherein 320 mg to 480 mg of at least one compound chosen from Compound I and pharmaceutically acceptable salts thereof is administered daily.

109. The method according to any one of embodiments 93-97, wherein 360 mg to 640 mg of at least one compound chosen from Compound I and pharmaceutically acceptable salts thereof is administered daily.

110. The method according to any one of embodiments 93-97, wherein 380 mg to 420 mg of at least one compound chosen from Compound I and pharmaceutically acceptable salts thereof is administered daily.

111. The method according to any one of embodiments 93-97, wherein 160 mg to 420 mg of at least one compound chosen from Compound I and pharmaceutically acceptable salts thereof is administered daily.

112. The method according to any one of embodiments 93-97, wherein 320 mg to 420 mg of at least one compound chosen from Compound I and pharmaceutically acceptable salts thereof is administered daily.

113. The method according to any one of embodiments 93-97, wherein 400 mg of at least one compound chosen from Compound I and pharmaceutically acceptable salts thereof is administered daily.

114. The method according to any one of embodiments 93-97, wherein 400 mg or 720 mg of at least one compound chosen from Compound I and pharmaceutically acceptable salts thereof is administered daily.

115. The method according to any one of embodiments 93-114, wherein at least one compound chosen from Compound I and pharmaceutically acceptable salts thereof is administered as a single dose, once daily.

116. The method according to any one of embodiments 93-114, wherein at least one compound chosen from Compound I and pharmaceutically acceptable salts thereof is administered in two doses daily.

117. The method according to any one of embodiments 93-95 and 97, wherein 25 mg to 200 mg of at least one compound chosen from Compound II and pharmaceutically acceptable salts thereof is administered daily.

118. The method according to any one of embodiments 93-95 and 97, wherein 50 mg to 150 mg of at least one compound chosen from Compound II and pharmaceutically acceptable salts thereof is administered daily.

119. The method according to any one of embodiments 93-95 and 97, wherein 75 mg to 200 mg of at least one compound chosen from Compound II and pharmaceutically acceptable salts thereof is administered daily.

120. The method according to any one of embodiments 93-95 and 97, wherein 50 mg of at least one compound chosen from Compound II and pharmaceutically acceptable salts thereof is administered daily.

121. The method according to any one of embodiments 93-95 and 97, wherein 100 mg of at least one compound chosen from Compound II and pharmaceutically acceptable salts thereof is administered daily.

122. The method according to any one of embodiments 93-95, 97, and 117-121, wherein at least one compound chosen from Compound II and pharmaceutically acceptable salts thereof is administered as a single dose, once daily.

123. The method according to any one of embodiments 93-95, 97, and 117-121, wherein at least one compound chosen from Compound II and pharmaceutically acceptable salts thereof is administered in two doses daily.

124. The method according to any one of embodiments 93, 94, 96, and 97, wherein: (i) 50 mg to 600 mg of at least one compound chosen from Compound III and pharmaceutically acceptable salts thereof is administered daily; or (ii) 50 mg to 600 mg of at least one compound chosen from Compound III-d and pharmaceutically acceptable salts thereof is administered daily.

125. The method according to any one of embodiments 93, 94, 96, and 97, wherein: (i) 50 mg to 450 mg of at least one compound chosen from Compound III and pharmaceutically acceptable salts thereof is administered daily; or (ii) 50 mg to 450 mg of at least one compound chosen from Compound III-d and pharmaceutically acceptable salts thereof is administered daily.

126. The method according to any one of embodiments 93, 94, 96, and 97, wherein: (i) 100 mg to 400 mg of at least one compound chosen from Compound III and pharmaceutically acceptable salts thereof is administered daily;

or (ii) 100 mg to 400 mg of at least one compound chosen from Compound III-d and pharmaceutically acceptable salts thereof is administered daily.

127. The method according to any one of embodiments 93, 94, 96, and 97, wherein: (i) 125 mg to 300 mg at least one compound chosen from Compound III and pharmaceutically acceptable salts thereof is administered daily; or (ii) 125 mg to 300 mg at least one compound chosen from Compound III-d and pharmaceutically acceptable salts thereof is administered daily.

128. The method according to any one of embodiments 93, 94, 96, and 97, wherein: (i) 150 mg to 300 mg of at least one compound chosen from Compound III and pharmaceutically acceptable salts thereof is administered daily; or (ii) 150 mg to 300 mg of at least one compound chosen from Compound III-d and pharmaceutically acceptable salts thereof is administered daily.

129. The method according to any one of embodiments 93, 94, 96, and 97, wherein: (i) 200 mg to 600 mg of at least one compound chosen from Compound III and pharmaceutically acceptable salts thereof is administered daily; or (ii) 100 mg to 300 mg of at least one compound chosen from Compound III-d and pharmaceutically acceptable salts thereof is administered daily.

130. The method according to any one of embodiments 93, 94, 96, and 97, wherein: (i) 300 mg or 600 mg of at least one compound chosen from Compound III and pharmaceutically acceptable salts thereof is administered daily; or (ii) 150 mg, 200 mg, or 300 mg of at least one compound chosen from Compound III-d and pharmaceutically acceptable salts thereof is administered daily.

131. The method according to any one of embodiments 93, 94, 96, and 97, wherein: (i) 150 mg of at least one compound chosen from Compound III and pharmaceutically acceptable salts thereof is administered twice daily; or (ii) 150 mg, 200 mg, or 300 mg of at least one compound chosen from Compound III-d and pharmaceutically acceptable salts thereof is administered once daily.

132. The method according to any one of embodiments 93, 94, 96, 97, and 124-130, wherein at least one compound chosen from Compound III or III-d and pharmaceutically acceptable salts thereof is administered once daily.

133. The method according to any one of embodiments 93, 94, 96, 97, and 124-130, wherein the dose of at least one compound chosen from Compound III or III-d, and pharmaceutically acceptable salts thereof is administered twice daily.

134. The method according to any one of embodiments 93 and 95-97, wherein 100 mg to 1,000 mg of at least one compound chosen from Compound IV and pharmaceutically acceptable salts thereof is administered daily.

135. The method according to any one of embodiments 93 and 95-97, wherein 400 mg to 1,000 mg of at least one compound chosen from Compound IV and pharmaceutically acceptable salts thereof is administered daily.

137. The method according to any one of embodiments 93 and 95-97, wherein 400 mg to 1,000 mg of at least one compound chosen from Compound IV and pharmaceutically acceptable salts thereof is administered daily.

137. The method according to any one of embodiments 93, 95-97, and 133-136 wherein 800 mg of at least one compound chosen from Compound IV and pharmaceutically acceptable salts thereof is administered once daily.

138. The method according to any one of embodiments 93, 95-97, and 133-136, wherein 400 mg of at least one compound chosen from Compound IV and pharmaceutically acceptable salts thereof is administered twice daily.

139. The method according to embodiment 93, wherein said patient has cystic fibrosis is chosen from patients with F508del/minimal function genotypes, patients with F508del/F508del genotypes, patients with F508del/gating genotypes, and patients with F508del/residual function genotypes.

140. The method according to embodiment 93, wherein said first pharmaceutical composition comprises 80 mg to 600 mg of at least one compound chosen from Compound I and pharmaceutically acceptable salts thereof is administered daily.

141. The method according to embodiment 93, wherein: (i) 50 mg to 200 mg of at least one compound chosen from Compound II and pharmaceutically acceptable salts thereof is administered daily and/or 150 mg to 600 mg of at least one compound chosen from Compound III and pharmaceutically acceptable salts thereof is administered daily; or (ii) 50 mg to 200 mg of at least one compound chosen from Compound II and pharmaceutically acceptable salts thereof is administered daily and/or 100 mg to 400 mg of at least one compound chosen from Compound III-d and pharmaceutically acceptable salts thereof is administered daily.

142. The method according to any one of embodiments 93, 140, and 141, wherein: (i) 150 mg to 600 mg of at least one compound chosen from Compound III and pharmaceutically acceptable salts thereof and/or 400 mg to 1,000 mg of at least one compound chosen from Compound IV and pharmaceutically acceptable salts thereof is administered daily; or (ii) 100 mg to 300 mg of at least one compound chosen from Compound III-d and pharmaceutically acceptable salts thereof and/or 400 mg to 1,000 mg of at least one compound chosen from Compound IV and pharmaceutically acceptable salts thereof is administered daily.

143. The method according to any one of embodiments 93-142, wherein said second pharmaceutical composition is administered prior to, subsequent to, or concurrently with said first pharmaceutical composition.

144. The method according to any one of embodiments 93-143, further comprising administering to said patient a third pharmaceutical composition, said composition comprising: (i) at least one compound chosen from Compound II, Compound III, Compound IV, and pharmaceutically acceptable salts thereof; or (ii) at least one compound chosen from Compound II, Compound III-d, Compound IV, and pharmaceutically acceptable salts thereof.

145. The method according to embodiment 144, wherein said third pharmaceutical composition is administered once daily.

146. The method according to any one of embodiments 1, 51, and 93, comprising administering to said patient Compound I.

147. The method according to any one of embodiments 1, 51, and 93, comprising administering to said patient a pharmaceutically acceptable salt of Compound I.

148. The method according to any one of embodiments 1, 51, and 93, comprising administering to said patient Compound II.

149. The method according to any one of embodiments 1, 51, and 93, comprising administering to said patient a pharmaceutically acceptable salt of Compound II.

150. The method according to any one of embodiments 1, 51, and 93, comprising administering to said patient Compound III or Compound III-d.

151. The method according to any one of embodiments 1, 51, and 93, comprising administering to said patient a pharmaceutically acceptable salt of Compound III or a pharmaceutically acceptable salt of Compound III-d.

152. The method according to any one of embodiments 1, 51, and 93, comprising administering to said patient Compound IV.
153. The method according to any one of embodiments 1, 51, and 93, comprising administering to said patient a pharmaceutically acceptable salt of Compound IV.
154. The method according to any one of embodiments 1, 51, and 93, comprising administering to said patient: (i) a pharmaceutically acceptable salt of Compound I; Compound II; and Compound III-d; or (ii) a pharmaceutically acceptable salt of Compound I; Compound II; and Compound III.
155. The method according to any one of embodiments 1, 51, and 93, comprising administering to said patient: (i) Compound I; Compound II; and Compound III; or (ii) Compound I; Compound II; and Compound III-d.
156. The method according to any one of embodiments 1, 51, and 93, comprising administering to said patient: (i) Compound I; and Compound III; or (ii) Compound I; and Compound III-d.
157. The method according to any one of embodiments 1, 51, and 93, comprising administering to said patient: (i) a pharmaceutically acceptable salt of Compound I and Compound III; or (ii) a pharmaceutically acceptable salt of Compound I and Compound III-d.
158. The method of any one of embodiments 47, 89, or 139, wherein the patient with a F508del/minimal function genotype has a minimal function mutation selected from:
159. The method of any one of embodiments 47, 89, or 139, wherein the patient with a F508del/gating genotype has a gating mutation selected from G178R, S549N, S549R, G551D, G551S, G1244E, S1251N, S1255P, and G1349D.
160. The method of any one of embodiments 47, 89, or 139, wherein the patient with a F508del/residual function genotype has a residual function mutation selected from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, K1060T, R117H, S1235R, I1027T, R668C, G576A, M470V, L997F, R75Q, R1070Q, R31C, D614G, G1069R, R1162L, E56K, A1067T, E193K, and K1060T.
161. The method of embodiment 51 or 93, wherein the pharmaceutically acceptable carrier is HPMCAS-HG.
162. The method according to any one of embodiments 1-161, wherein: (i) 100 mg to 600 mg of at least one compound chosen from Compound I and pharmaceutically acceptable salts thereof is administered once daily; 50 to 200 mg of at least one compound chosen from Compound II and pharmaceutically acceptable salts thereof is administered once daily; and 150 mg to 600 mg of Compound III is administered twice daily; or (ii) 100 mg to 600 mg of at least one compound chosen from Compound I and pharmaceutically acceptable salts thereof is administered once daily; 50 to 200 mg of at least one compound chosen from Compound II and pharma-

| Mutation | | | | |
|---|---|---|---|---|
| S4X | C276X | G542X | R792X | E1104X |
| G27X | Q290X | G550X | E822X | R1158X |
| Q39X | G330X | Q552X | W846X | R1162X |
| W57X | W401X | R553X | Y849X | S1196X |
| E60X | Q414X | E585X | R851X | W1204X |
| R75X | S434X | G673X | Q890X | L1254X |
| E92X | S466X | Q685X | S912X | S1255X |
| Q98X | S489X | R709X | Y913X | W1282X |
| Y122X | Q493X | K710X | W1089X | Q1313X |
| E193X | W496X | L732X | Y1092X | E1371X |
| L218X | C524X | R764X | W1098X | Q1382X |
| Q220X | Q525X | R785X | R1102X | Q1411X |
| 185+1G→T | 711+5G→A | 1717-8G→A | 2622+1G→A | 3121-1G→A |
| 296+1G→A | 712-1G→T | 1717-1G→A | 2790-1G→C | 3500-2A→G |
| 405+1G→A | 1248+1G→A | 1811+1G→C | 3040G→C | 3600+2insT |
| 405+3A→C | 1249-1G→A | 1811+1.6kbA→G | (G970R) | 3850-1G→A |
| 406-1G→A | 1341+1G→A | 1812-1G→A | 3120G→A | 4005+1G→A |
| 621+1G→T | 1525-2A→G | 1898+1G→A | 3120+1G→A | 4374+1G→T |
| 711+1G→T | 1525-1G→A | 1898+1G→C | 3121-2A→G | |
| 182delT | 1119delA | 1782delA | 2732insA | 3876delA |
| 306insA | 1138insG | 1824delA | 2869insG | 3878delG |
| 365-366insT | 1154insTC | 2043delG | 2896insAG | 3905insT |
| 394delTT | 1161delC | 2143delT | 2942insT | 4016insT |
| 442delA | 1213delT | 2183AA→G[a] | 2957delT | 4021dupT |
| 444delA | 1259insA | 2184delA | 3007delG | 4040delA |
| 457TAT→G | 1288insTA | 2184insA | 3028delA | 4279insA |
| 541delC | 1471delA | 2307insA | 3171delC | 4326delTC |
| 574delA | 1497delGG | 2347delG | 3659delC | |
| 663delT | 1548delG | 2585delT | 3737delA | |
| 935delA | 1609del CA | 2594delGT | 3791delC | |
| 1078delT | 1677delTA | 2711delT | 3821delT | |
| CFTRdele2, 3 | 1461ins4 | | 2991del32 | |
| CFTRdele22, 23 | 1924del7 | | 3199del6[a] | |
| 124del23bp | 2055del9→A | | 3667ins4 | |
| 852del22 | 2105- 2117del13insAGAAA | | 4010del4 | |
| 991del5 | 2721del11 | | 4209TGTT→AA | |
| A46D[b] | V520F | Y569D[b] | N1303K | |
| G85E | A559T[b] | L1065P | | |
| R347P | R560T | R1066C | | |
| L467P[b] | R560S | L1077P[b] | | |
| I507del | A561E | M1101K | | | ceutically acceptable salts thereof is administered once daily; and 150 mg to 600 mg of Compound III-d is administered twice daily.

163. The method according to any one of embodiments 1-161, wherein: (i) 400 mg of at least one compound chosen from Compound I and pharmaceutically acceptable salts thereof is administered once daily; 100 mg of at least one compound chosen from Compound II and pharmaceutically acceptable salts thereof is administered once daily; and 150 mg or 300 mg of at least one compound chosen from Compound III and pharmaceutically acceptable salts thereof is administered twice daily; or (ii) 400 mg of at least one compound chosen from Compound I and pharmaceutically acceptable salts thereof is administered once daily; 100 mg of at least one compound chosen from Compound II and pharmaceutically acceptable salts thereof is administered once daily; and 150 mg, 200 mg, or 300 mg of at least one compound chosen from Compound III-d and pharmaceutically acceptable salts thereof is administered once daily.

164. The method according to any one of embodiments 1-161, wherein: (i) 50 mg to 300 mg of at least one compound chosen from Compound I and pharmaceutically acceptable salts thereof is administered twice daily; 50 mg of at least one compound chosen from Compound II and pharmaceutically acceptable salts thereof is administered twice daily; and 150 mg or 300 mg of at least one compound chosen from Compound III and pharmaceutically acceptable salts thereof is administered twice daily; or (ii) 50 mg to 300 mg of at least one compound chosen from Compound I and pharmaceutically acceptable salts thereof is administered twice daily; 50 mg of at least one compound chosen from Compound II and pharmaceutically acceptable salts thereof is administered twice daily; and 150 mg, 200 mg, or 300 mg of at least one compound chosen from Compound III-d and pharmaceutically acceptable salts thereof is administered once daily.

165. The method according to any one of embodiments 1-161, wherein: (i) 100 mg to 600 mg of at least one compound chosen from Compound I and pharmaceutically acceptable salts thereof is administered once daily; and 150 mg to 600 mg of at least one compound chosen from Compound III and pharmaceutically acceptable salts thereof is administered twice daily; or (ii) 100 mg to 600 mg of at least one compound chosen from Compound I and pharmaceutically acceptable salts thereof is administered once daily; and 150 mg to 600 mg of at least one compound chosen from Compound III-d and pharmaceutically acceptable salts thereof is administered once daily.

166. The method according to any one of embodiments 1-161, wherein: (i) wherein 50 mg to 300 mg of at least one compound chosen from Compound I and pharmaceutically acceptable salts thereof is administered twice daily; and 150 mg or 300 mg of at least one compound chosen from Compound III and pharmaceutically acceptable salts thereof is administered twice daily; or (ii) 50 mg to 300 mg of at least one compound chosen from Compound I and pharmaceutically acceptable salts thereof is administered twice daily; and 150 mg, 200 mg, or 300 mg of at least one compound chosen from Compound III-d and pharmaceutically acceptable salts thereof is administered once daily.

167. The method according to any one of embodiments 162-166, wherein 80 mg, 160 mg, 240 mg, 320 mg, or 400 mg of at least one compound chosen from Compound I and pharmaceutically acceptable salts thereof is administered once daily.

168. The method according to any one of embodiments 162-166, wherein 160 mg or 240 mg of at least one compound chosen from Compound I and pharmaceutically acceptable salts thereof is administered twice daily.

169. The method according to any one of embodiments 1-161, wherein: (i) 80 mg, 160 mg, 240 mg, 320 mg, or 400 mg of at least one compound chosen from Compound I and pharmaceutically acceptable salts thereof is administered once daily; and 100 mg of at least one compound chosen from Compound II and pharmaceutically acceptable salts thereof is administered once daily; and 150 mg or 300 mg of at least one compound chosen from Compound III and pharmaceutically acceptable salts thereof is administered twice daily; or (ii) 80 mg, 160 mg, 240 mg, 320 mg, or 400 mg of at least one compound chosen from Compound I and pharmaceutically acceptable salts thereof is administered once daily; and 100 mg of at least one compound chosen from Compound II and pharmaceutically acceptable salts thereof is administered once daily; and 150 mg or 200 mg, or 300 mg of at least one compound chosen from Compound III-d and pharmaceutically acceptable salts thereof is administered once daily.

170. The method according to any one of embodiments 1-161, wherein: (i) 80 mg, 160 mg, 240 mg, 320 mg, or 400 mg of at least one compound chosen from Compound I and pharmaceutically acceptable salts thereof is once daily; and 100 mg of Compound II is administered once daily; and 150 mg or 300 mg of Compound III is administered twice daily; or (ii) 80 mg, 160 mg, 240 mg, 320 mg, or 400 mg of at least one compound chosen from Compound I and pharmaceutically acceptable salts thereof is once daily; and 100 mg of Compound II is administered once daily; and 150 mg, 200 mg, or 300 mg mg of Compound III-d is administered once daily.

171. The method according to any one of embodiments 1-161, wherein: (i) 160 mg or 240 mg of at least one compound chosen from Compound I and pharmaceutically acceptable salts thereof is administered twice daily; 100 mg of Compound II is administered once daily; and 150 mg or 300 mg of Compound III is administered twice daily; or (ii) 160 mg or 240 mg of at least one compound chosen from Compound I and pharmaceutically acceptable salts thereof is administered twice daily; 100 mg of Compound II is administered once daily; and 150 mg, 200 mg, or 300 mg of Compound III-d is administered once daily.

172. The method according to any one of embodiments 1-161, wherein: (i) 80 mg, 160 mg, 240 mg, 320 mg, or 400 mg of at least one compound chosen from Compound I and pharmaceutically acceptable salts thereof is administered once daily; and 150 mg or 300 mg of at least one compound chosen from Compound III and pharmaceutically acceptable salts thereof is administered twice daily; or (ii) 80 mg, 160 mg, 240 mg, 320 mg, or 400 mg of at least one compound chosen from Compound I and pharmaceutically acceptable salts thereof is administered once daily; and 150 mg, 200 mg, or 300 mg of at least one compound chosen from Compound III-d and pharmaceutically acceptable salts thereof is administered once daily.

173. The method according to any one of embodiments 1-161, wherein: (i) 80 mg, 160 mg, 240 mg, 320 mg, or 400 mg of at least one compound chosen from Compound I and pharmaceutically acceptable salts thereof is administered once daily; and 200 mg or 300 mg of Compound III-d is administered once daily; or (ii) 80 mg, 160 mg, 240 mg, 320 mg, or 400 mg of at least one compound chosen from Compound I and pharmaceutically acceptable salts thereof is administered once daily; and 150 mg, 200 mg, or 300 mg of Compound III-d is administered once daily.

174. The method according to any one of embodiments 1-161, wherein: (i) 160 mg or 240 mg of at least one compound chosen from Compound I and pharmaceutically acceptable salts thereof is administered twice daily; and 150 mg or 300 mg of Compound III is administered twice daily; or (ii) 160 mg or 240 mg of at least one compound chosen from Compound I and pharmaceutically acceptable salts thereof is administered twice daily; and 150 mg, 200 mg, or 300 mg of Compound III-d is administered once daily.

175. The method according to any one of embodiments 1-161, wherein: (i) 160 mg or 240 mg of at least one compound chosen from Compound I and pharmaceutically acceptable salts thereof is administered twice daily; and 150 mg or 300 mg of Compound III is administered twice daily; or (ii) 160 mg or 240 mg of at least one compound chosen from Compound I and pharmaceutically acceptable salts thereof is administered twice daily; and 150 mg, 200 mg, or 300 mg of Compound III-d is administered once daily.

176. The method according to any one of embodiments 1-161, wherein 80 mg to 800 mg of at least one compound chosen from Compound I and pharmaceutically acceptable salts thereof is administered daily.

177. The method according to any one of embodiments 1-161, wherein 80 mg, 160 mg, 240 mg, 320 mg, 400 mg, 480 mg, 560 mg, 640 mg, or 720 mg of at least one compound chosen from Compound I and pharmaceutically acceptable salts thereof is administered daily.

178. The method according to any one of embodiments 1-161, wherein: (i) 80 mg, 160 mg, 240 mg, 320 mg, 400 mg, 480 mg, 560 mg, 640 mg, or 720 mg of at least one compound chosen from Compound I and pharmaceutically acceptable salts thereof is administered daily; 50 mg to 200 mg of at least one compound chosen from Compound II and pharmaceutically acceptable salts thereof is administered once daily; and 150 mg to 600 mg of Compound III is administered twice daily; or (ii) 80 mg, 160 mg, 240 mg, 320 mg, 400 mg, 480 mg, 560 mg, 640 mg, or 720 mg of at least one compound chosen from Compound I and pharmaceutically acceptable salts thereof is administered daily; 50 mg to 200 mg of at least one compound chosen from Compound II and pharmaceutically acceptable salts thereof is administered once daily; and 150 mg to 600 mg of Compound III-d is administered once daily.

179. The method according to any one of embodiments 1-161, wherein: (i) 80 mg, 160 mg, 240 mg, 320 mg, 400 mg, 480 mg, 560 mg, 640 mg, or 720 mg of at least one compound chosen from Compound I and pharmaceutically acceptable salts thereof is administered daily; 100 mg of Compound II is administered once daily; and 150 mg or 300 mg of at least one compound chosen from Compound III and pharmaceutically acceptable salts thereof is administered twice daily; or (ii) 80 mg, 160 mg, 240 mg, 320 mg, 400 mg, 480 mg, 560 mg, 640 mg, or 720 mg of at least one compound chosen from Compound I and pharmaceutically acceptable salts thereof is administered daily; 100 mg of Compound II is administered once daily; and 150 mg, 200 mg, or 300 mg of at least one compound chosen from Compound III-d and pharmaceutically acceptable salts thereof is administered once daily.

180. The method according to any one of embodiments 1-161, wherein: (i) 80 mg, 160 mg, 240 mg, 320 mg, 400 mg, 480 mg, 560 mg, 640 mg, or 720 mg of at least one compound chosen from Compound I and pharmaceutically acceptable salts thereof is administered daily; 50 mg of Compound II is administered twice daily and 150 mg or 300 mg of at least one compound chosen from Compound III and pharmaceutically acceptable salts thereof is administered twice daily; or (ii) 80 mg, 160 mg, 240 mg, 320 mg, 400 mg, 480 mg, 560 mg, 640 mg, or 720 mg of at least one compound chosen from Compound I and pharmaceutically acceptable salts thereof is administered daily; 50 mg of Compound II is administered twice daily and 150 mg, 200 mg, or 300 mg of at least one compound chosen from Compound III-d and pharmaceutically acceptable salts thereof is administered once daily.

181. A method of treating cystic fibrosis comprising administering to a patient in need thereof:

(A) 120 mg of at least one compound chosen from Compound I and pharmaceutically acceptable salts thereof twice daily:

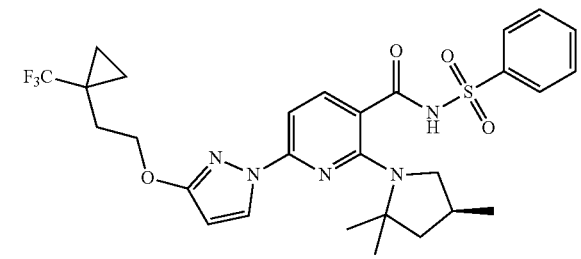 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of at least one compound chosen from Compound II and pharmaceutically acceptable salts thereof once daily or 50 mg of at least one compound chosen from Compound II and pharmaceutically acceptable salts thereof twice daily:

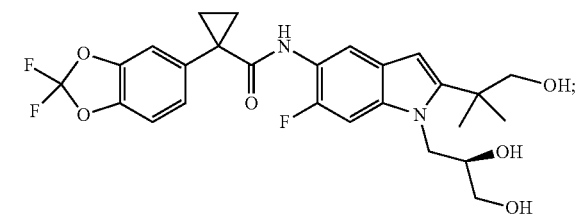 [SMILES: CC(C)(CO)c1cc2cc(NC(=O)C3(c4ccc5c(c4)OC(F)(F)O5)CC3)c(F)cc2n1C[C@@H](O)CO]

and (C) 150 mg of at least one compound chosen from Compound III and pharmaceutically acceptable salts thereof twice daily:

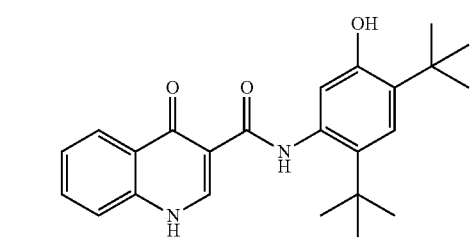

182. A method of treating cystic fibrosis comprising administering to a patient in need thereof:

(A) 240 mg of at least one compound chosen from Compound I and pharmaceutically acceptable salts thereof once daily:

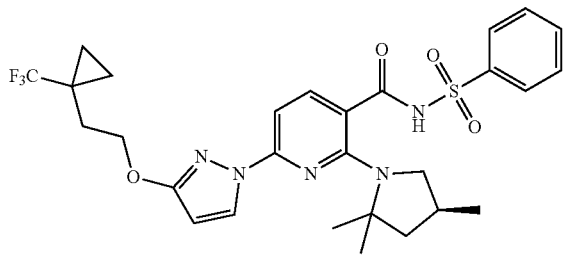 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of at least one compound chosen from Compound II and pharmaceutically acceptable salts thereof once daily or 50 mg of at least one compound chosen from Compound II and pharmaceutically acceptable salts thereof twice daily:

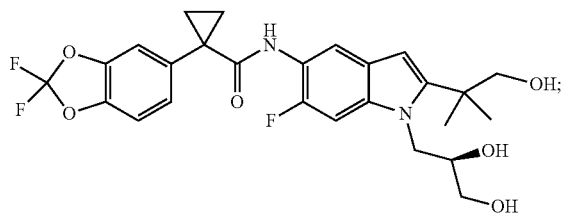 [SMILES: CC(C)(CO)c1cc2cc(NC(=O)C3(c4ccc5c(c4)OC(F)(F)O5)CC3)c(F)cc2n1C[C@@H](O)CO]

and
(C) 150 mg of at least one compound chosen from Compound III and pharmaceutically acceptable salts thereof twice daily:

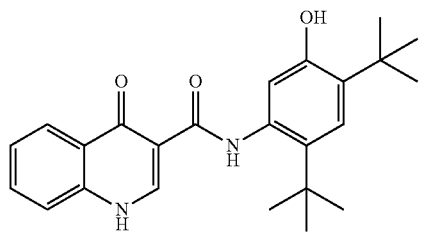

183. A method of treating cystic fibrosis comprising administering to a patient in need thereof:
(A) 400 mg of at least one compound chosen from Compound I and pharmaceutically acceptable salts thereof once daily:

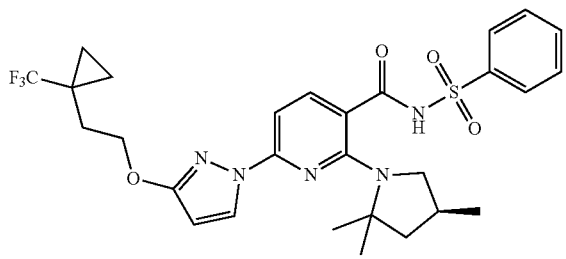 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of at least one compound chosen from Compound II and pharmaceutically acceptable salts thereofonce daily or 50 mg of at least one compound chosen from Compound II and pharmaceutically acceptable salts thereof twice daily:

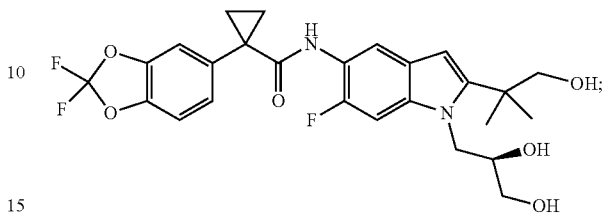

and
(C) 150 mg of at least one compound chosen from Compound III and pharmaceutically acceptable salts thereof twice daily:

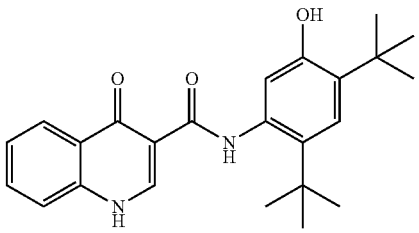

184. A method of treating cystic fibrosis comprising administering to a patient in need thereof:
(A) 120 mg of at least one compound chosen from Compound I and pharmaceutically acceptable salts thereof twice daily:

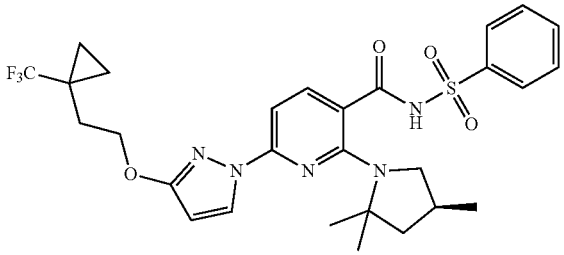 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of at least one compound chosen from Compound II and pharmaceutically acceptable salts thereofonce daily or 50 mg of at least one compound chosen from Compound II and pharmaceutically acceptable salts thereof twice daily:

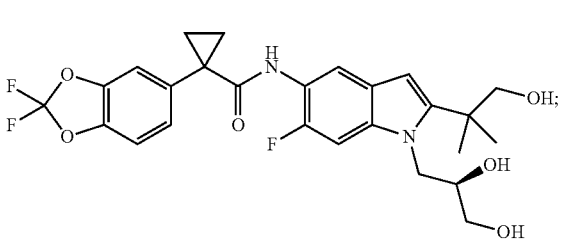 [SMILES: CC(C)(CO)c1cc2cc(NC(=O)C3(c4ccc5c(c4)OC(F)(F)O5)CC3)c(F)cc2n1C[C@@H](O)CO]

and
(C) 300 mg of at least one compound chosen from Compound III and pharmaceutically acceptable salts thereof twice daily:

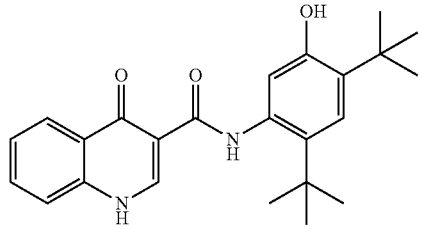

185. A method of treating cystic fibrosis comprising administering to a patient in need thereof:
(A) 240 mg of at least one compound chosen from Compound I and pharmaceutically acceptable salts thereof once daily:

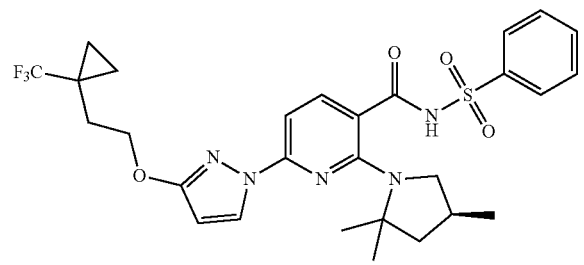 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of at least one compound chosen from Compound II and pharmaceutically acceptable salts thereof once daily or 50 mg of and pharmaceutically acceptable salts thereof Compound II and pharmaceutically acceptable salts thereof twice daily:

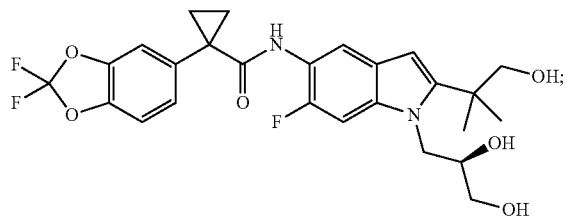 [SMILES: CC(C)(CO)c1cc2cc(NC(=O)C3(c4ccc5c(c4)OC(F)(F)O5)CC3)c(F)cc2n1C[C@@H](O)CO]

and
(C) 300 mg of at least one compound chosen from Compound III and pharmaceutically acceptable salts thereof twice daily:

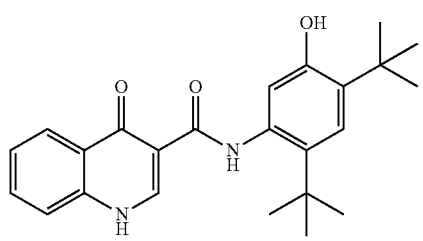

186. A method of treating cystic fibrosis comprising administering to a patient in need thereof:
(A) 400 mg of at least one compound chosen from Compound I and pharmaceutically acceptable salts thereof twice daily:

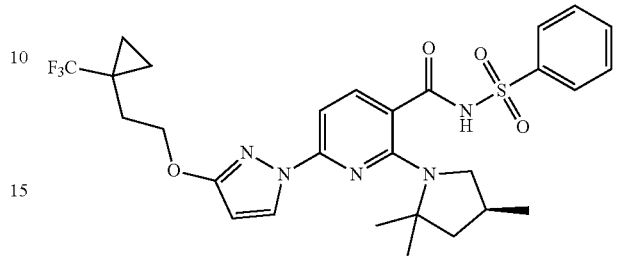

(B) 100 mg of at least one compound chosen from Compound II and pharmaceutically acceptable salts thereof once daily or 50 mg of at least one compound chosen from Compound II and pharmaceutically acceptable salts thereof twice daily:

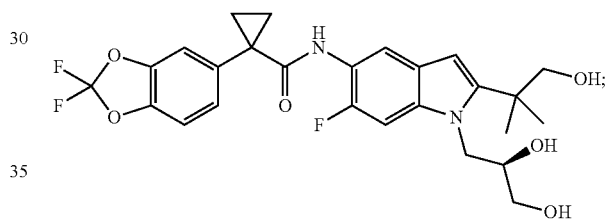

and
(C) 300 mg of at least one compound chosen from Compound III and pharmaceutically acceptable salts thereof twice daily:

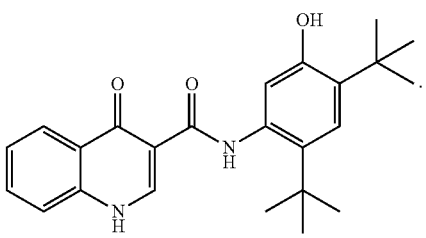 [SMILES: CC(C)(C)c1cc(C(C)(C)C)c(NC(=O)c2c[nH]c3ccccc3c2=O)cc1O]

187. The method according to any one of embodiments 181-186, wherein said patient has cystic fibrosis is chosen from patients with F508del/minimal function genotypes, patients with F508del/F508del genotypes, patients with F508del/gating genotypes, and patients with F508del/residual function genotypes.

188. The method according to embodiment 187, wherein the patient with a F508del/minimal function genotype has a minimal function mutation selected from:

| Mutation | | | | |
|---|---|---|---|---|
| S4X | C276X | G542X | R792X | E1104X |
| G27X | Q290X | G550X | E822X | R1158X |
| Q39X | G330X | Q552X | W846X | R1162X |
| W57X | W401X | R553X | Y849X | S1196X |
| E60X | Q414X | E585X | R851X | W1204X |
| R75X | S434X | G673X | Q890X | L1254X |
| E92X | S466X | Q685X | S912X | S1255X |
| Q98X | S489X | R709X | Y913X | W1282X |
| Y122X | Q493X | K710X | W1089X | Q1313X |
| E193X | W496X | L732X | Y1092X | E1371X |
| L218X | C524X | R764X | W1098X | Q1382X |
| Q220X | Q525X | R785X | R1102X | Q1411X |
| 185+1G→T | 711+5G→A | 1717-8G→A | 2622+1G→A | 3121-1G→A |
| 296+1G→A | 712-1G→T | 1717-1G→A | 2790-1G→C | 3500-2A→G |
| 405+1G→A | 1248+1G→A | 1811+1G→C | 3040G→C | 3600+2insT |
| 405+3A→C | 1249-1G→A | 1811+1.6kbA→G | (G970R) | 3850-1G→A |
| 406-1G→A | 1341+1G→A | 1812-1G→A | 3120G→A | 4005+1G→A |
| 621+1G→T | 1525-2A→G | 1898+1G→A | 3120+1G→A | 4374+1G→T |
| 711+1G→T | 1525-1G→A | 1898+1G→C | 3121-2A→G | |
| 182delT | 1119delA | 1782delA | 2732insA | 3876delA |
| 306insA | 1138insG | 1824delA | 2869insG | 3878delG |
| 365-366insT | 1154insTC | 2043delG | 2896insAG | 3905insT |
| 394delTT | 1161delC | 2143delT | 2942insT | 4016insT |
| 442delA | 1213delT | 2183AA→G $^a$ | 2957delT | 4021dupT |
| 444delA | 1259insA | 2184delA | 3007delG | 4040delA |
| 457TAT→G | 1288insTA | 2184insA | 3028delA | 4279insA |
| 541delC | 1471delA | 2307insA | 3171delC | 4326delTC |
| 574delA | 1497delGG | 2347delG | 3659delC | |
| 663delT | 1548delG | 2585delT | 3737delA | |
| 935delA | 1609delCA | 2594delGT | 3791delC | |
| 1078delT | 1677delTA | 2711delT | 3821delT | |
| CFTRdele2, 3 | 1461ins4 | | 2991del32 | |
| CFTRdele22, 23 | 1924del7 | | 3667ins4 | |
| 124del23bp | 2055del9→A | | 4010del4 | |
| 852del22 | 2105-2117del13insAGAAA | | 4209TGTT→AA | |
| 991del5 | 2721del11 | | | |
| A46D$^b$ | V520F | Y569D$^b$ | N1303K | |
| G85E | A559T$^b$ | L1065P | | |
| R347P | R560T | R1066C | | |
| L467P$^b$ | R560S | L1077P$^b$ | | |
| I507del | A561E | M1101K | | |

189. The method according to embodiment 187, wherein the patient with a F508del/gating genotype has a gating mutation selected from G178R, S549N, S549R, G551D, G551S, G1244E, S1251N, S1255P, and G1349D.

190. The method according to embodiment 187, wherein the patient with a F508del/residual function genotype has a residual function mutation selected from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, K1060T, R117H, S1235R, I1027T, R668C, G576A, M470V, L997F, R75Q, R1070Q, R31C, D614G, G1069R, R1162L, E56K, A1067T, E193K, and K1060T.

191. The method according to any one of embodiments 181-190, wherein the absolute change in said patient's percent predicted forced expiratory volume in one second (ppFEV$_1$) after 15 days of administration of said at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 3% to 40% relative to the ppFEV1 of the patient prior to said administration.

192. The method according to embodiment 191, wherein said patient has one F508del mutation and one minimal function mutation, and wherein patient has not taken any of said at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof.

193. The method according to embodiment 191, wherein said patient has two copies of F508del mutation, and wherein patient has taken at least one compound chosen from Compound II and pharmaceutically acceptable salts thereof, and at least one compound chosen from Compound III or III-d and pharmaceutically acceptable salts thereof, but not any of said at least one compound chosen from Compound I and pharmaceutically acceptable salts thereof.

194. The method according to any one of embodiments 181-193, wherein said absolute change in said patient's ppFEV$_1$ ranges from 3% to 35%.

195. The method according to any one of embodiments 181-194, wherein said at least one compound chosen from Compound I and pharmaceutically acceptable salts thereof is comprised in a first pharmaceutical composition; said at least one compound chosen from Compound II and pharmaceutically acceptable salts thereof is comprised in a second pharmaceutical composition; and said at least one compound chosen from Compound III or III-d and pharmaceutically acceptable salts thereof is comprised in a third pharmaceutical composition.

196. The method according to any one of embodiments 181-194, wherein said at least one compound chosen from Compound I and pharmaceutically acceptable salts thereof is comprised in a first pharmaceutical composition; and said at least one compound chosen from Compound II and pharmaceutically acceptable salts thereof and said at least one compound chosen from Compound III or III-d and pharmaceutically acceptable salts thereof are comprised in a second pharmaceutical composition.

197. The method of embodiment 196, wherein said second pharmaceutical composition comprises a half of the daily dose of said at least one compound chosen from Compound III and pharmaceutically acceptable salts thereof, and the other half of the daily dose of said at least one compound chosen from Compound III and pharmaceutically acceptable salts thereof is administered to said patient in a third pharmaceutical composition.

198. The method according to any one of embodiments 181-194, wherein said at least one compound chosen from Compound I and pharmaceutically acceptable salts thereof is comprised in a first pharmaceutical composition; said at least one compound chosen from Compound II and pharmaceutically acceptable salts thereof is comprised in a second pharmaceutical composition; and said at least one compound chosen from (i) Compound III and pharmaceutically acceptable salts thereof, or (ii) Compound III-d and pharmaceutically acceptable salts thereof is comprised in the first pharmaceutical composition.

199. The method according to any one of embodiments 181-194, wherein said at least one compound chosen from Compound I and pharmaceutically acceptable salts thereof, said at least one compound chosen from Compound II and pharmaceutically acceptable salts thereof, and said at least one compound chosen from i) Compound III and pharmaceutically acceptable salts thereof, or (ii) Compound III-d and pharmaceutically acceptable salts thereof are comprised in a first pharmaceutical composition.

200. The method according to embodiment 199, wherein the first pharmaceutical composition is administered to the patient twice daily.

201. A method of treating cystic fibrosis comprising administering to a patient in need thereof:

(A) 120 mg of at least one compound chosen from Compound I and pharmaceutically acceptable salts thereof twice daily:

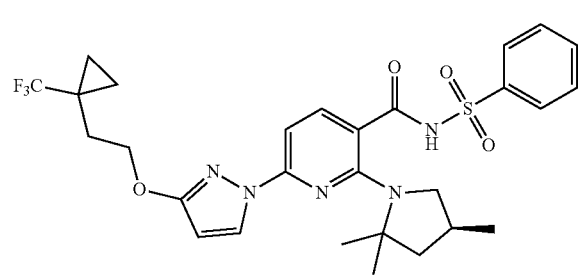 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of Compound II once daily or 50 mg of Compound II twice daily:

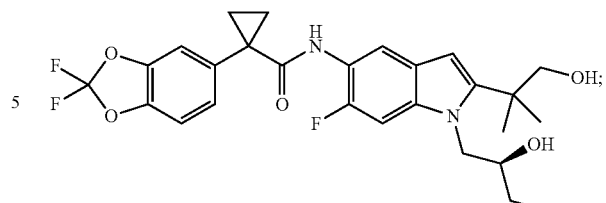

and
(C) 150 mg of Compound III twice daily:

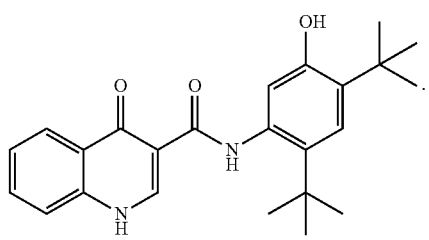 [SMILES: CC(C)(C)c1cc(C(C)(C)C)c(NC(=O)c2c[nH]c3ccccc3c2=O)cc1O]

202. A method of treating cystic fibrosis comprising administering to a patient in need thereof:
(A) 240 mg of at least one compound chosen from Compound I and pharmaceutically acceptable salts thereof once daily:

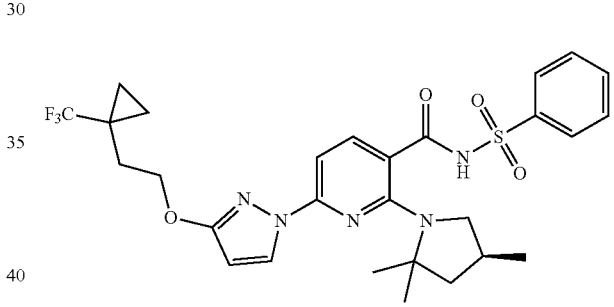

(B) 100 mg of Compound II once daily or 50 mg of Compound II twice daily:

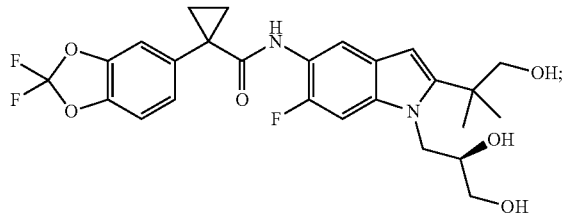 [SMILES: CC(C)(CO)c1cc2cc(NC(=O)C3(c4ccc5c(c4)OC(F)(F)O5)CC3)c(F)cc2n1C[C@@H](O)CO]

and
(C) 150 mg of Compound III twice daily:

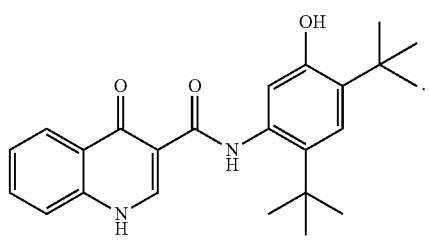 [SMILES: CC(C)(C)c1cc(C(C)(C)C)c(NC(=O)c2c[nH]c3ccccc3c2=O)cc1O]

203. A method of treating cystic fibrosis comprising administering to a patient in need thereof:

(A) 400 mg of at least one compound chosen from Compound I and pharmaceutically acceptable salts thereof once daily:

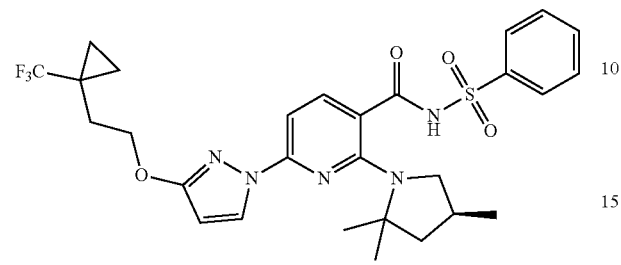

(B) 100 mg of Compound II once daily or 50 mg Compound II twice daily:

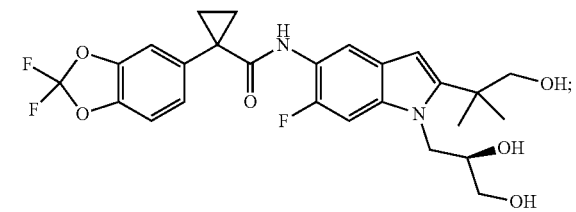 [SMILES: CC(C)(CO)c1cc2cc(NC(=O)C3(c4ccc5c(c4)OC(F)(F)O5)CC3)c(F)cc2n1C[C@@H](O)CO]

and
(C) 150 mg of Compound III twice daily:

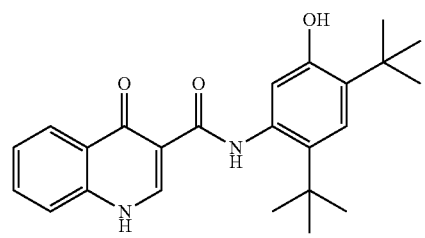

204. A method of treating cystic fibrosis comprising administering to a patient in need thereof:

(A) 120 mg of at least one compound chosen from Compound I and pharmaceutically acceptable salts thereof twice daily:

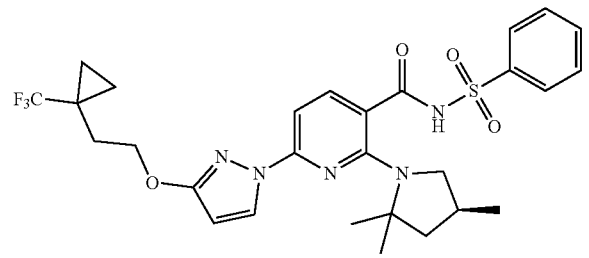 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of Compound II once daily or 50 mg of Compound II twice daily:

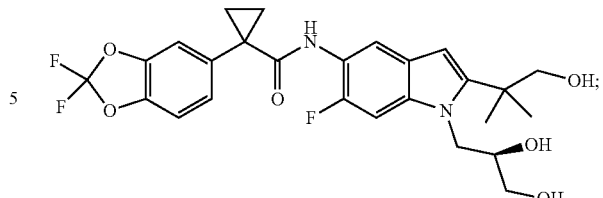

and
(C) 300 mg of Compound III twice daily:

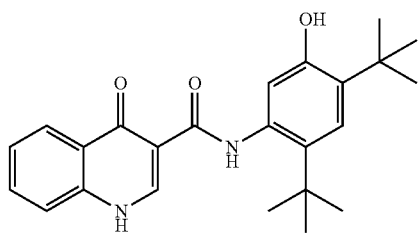

205. A method of treating cystic fibrosis comprising administering to a patient in need thereof:

(A) 240 mg of at least one compound chosen from Compound I and pharmaceutically acceptable salts thereof once daily:

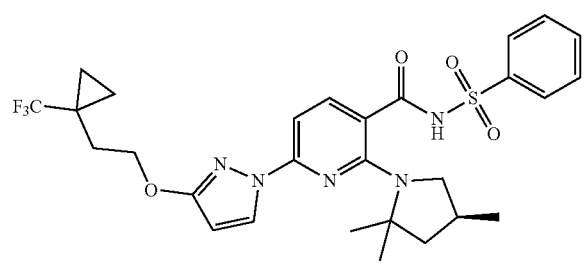 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of Compound II once daily or 50 mg of Compound II twice daily:

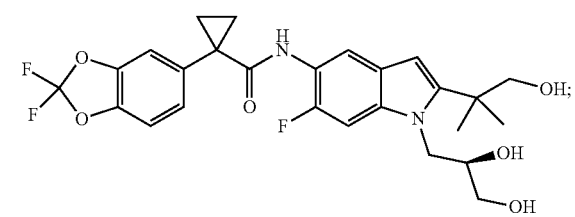 [SMILES: CC(C)(CO)c1cc2cc(NC(=O)C3(c4ccc5c(c4)OC(F)(F)O5)CC3)c(F)cc2n1C[C@@H](O)CO]

and
(C) 300 mg of Compound III twice daily:

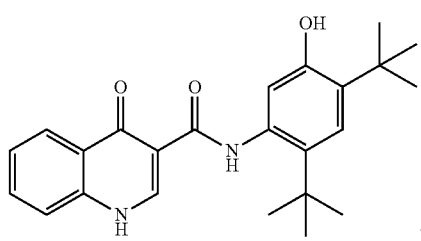

206. A method of treating cystic fibrosis comprising administering to a patient in need thereof:

(A) 400 mg of at least one compound chosen from Compound I and pharmaceutically acceptable salts thereof twice daily:

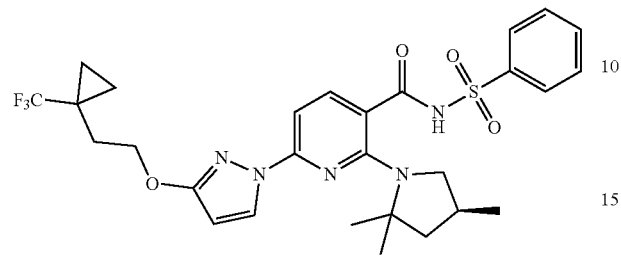

(B) 100 mg of Compound II once daily or 50 mg of Compound II twice daily:

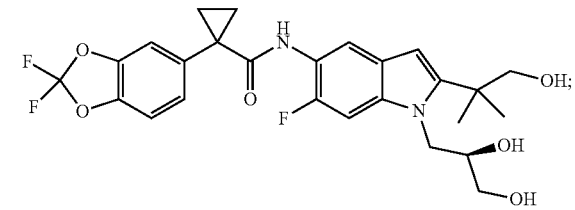 [SMILES: CC(C)(CO)c1cc2cc(NC(=O)C3(c4ccc5c(c4)OC(F)(F)O5)CC3)c(F)cc2n1C[C@@H](O)CO]

and
(C) 300 mg of Compound III twice daily:

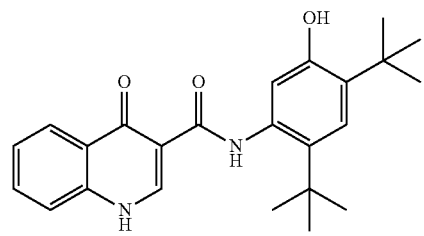

207. A method of treating cystic fibrosis comprising administering to a patient in need thereof:

(A) 400 mg of at least one compound chosen from Compound I and pharmaceutically acceptable salts thereof once daily:

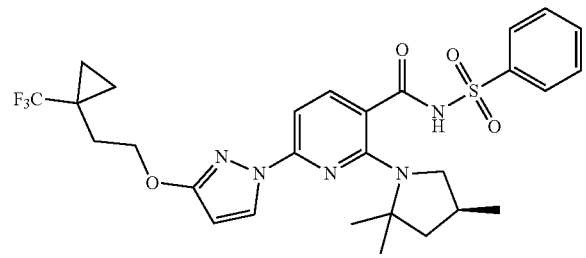 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of Compound II once daily or 50 mg of Compound II twice daily:

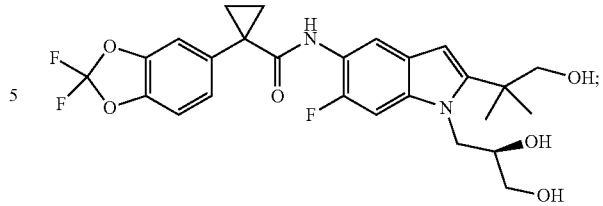

and
(C) 200 mg of Compound III-d once daily:

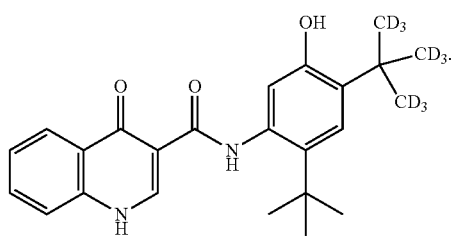 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

208. A method of treating cystic fibrosis comprising administering to a patient in need thereof:

(A) 240 mg of at least one compound chosen from Compound I and pharmaceutically acceptable salts thereof once daily:

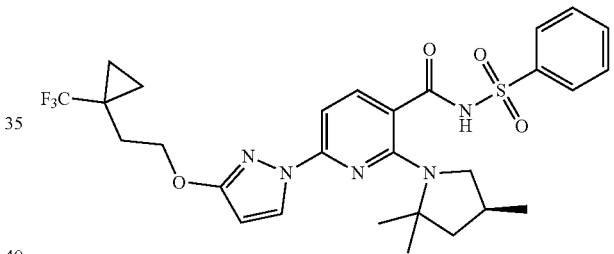

(B) 100 mg of Compound II once daily or 50 mg of Compound II twice daily:

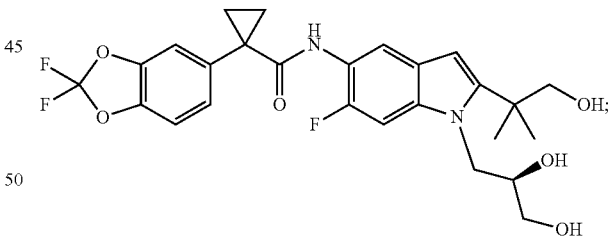

and
(C) 200 mg of Compound III-d once daily:

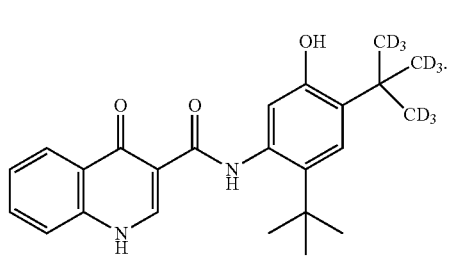 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

209. A method of treating cystic fibrosis comprising administering to a patient in need thereof:
(A) 400 mg of at least one compound chosen from Compound I and pharmaceutically acceptable salts thereof once daily:

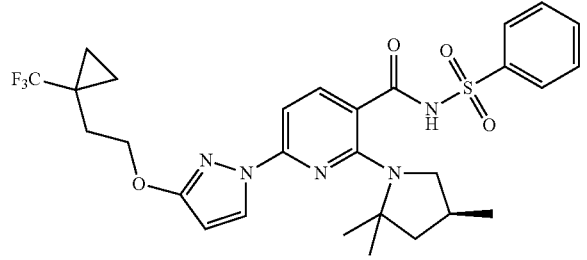 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

(B) 100 mg of Compound II once daily or 50 mg Compound II twice daily:

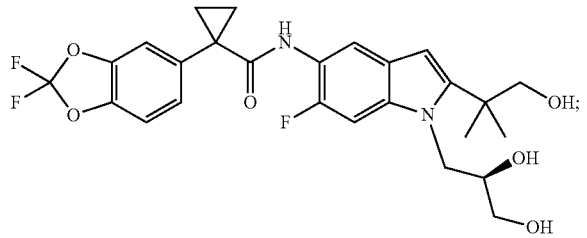 [SMILES: CC(C)(CO)c1cc2cc(NC(=O)C3(c4ccc5c(c4)OC(F)(F)O5)CC3)c(F)cc2n1C[C@@H](O)CO]

and
(C) 150 mg of Compound III-d once daily:

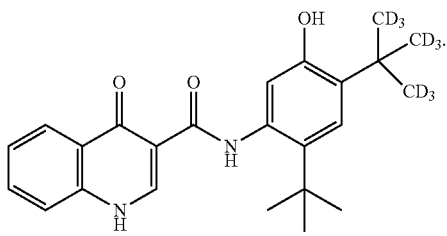 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

210. A method of treating cystic fibrosis comprising administering to a patient in need thereof:
(A) 240 mg of at least one compound chosen from Compound I and pharmaceutically acceptable salts thereof once daily:

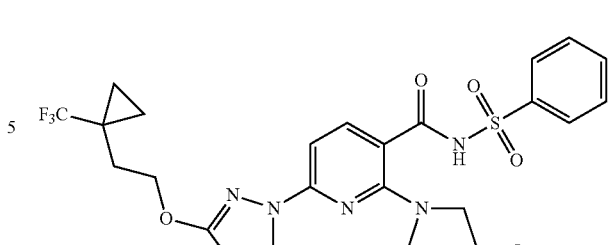

(B) 100 mg of Compound II once daily or 50 mg Compound II twice daily:

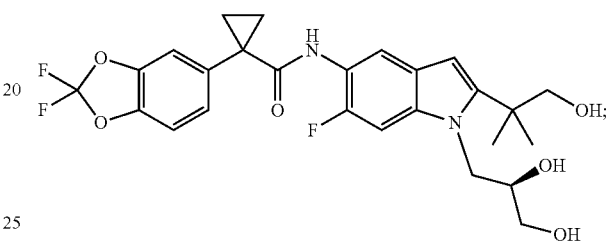

and
(C) 150 mg of Compound III-d once daily:

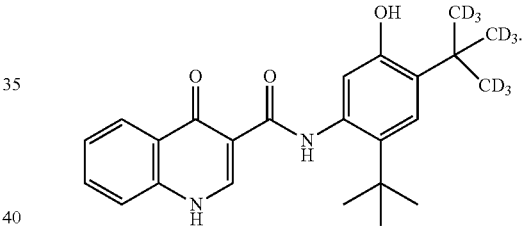

211. The method according to any one of embodiments 201-210, wherein said patient has cystic fibrosis is chosen from patients with F508del/minimal function genotypes, patients with F508del/F508del genotypes, patients with F508del/gating genotypes, patients with F508del/residual function genotypes.

212. The method according to embodiment 211, wherein the patient with a F508del/minimal function genotype has a minimal function mutation selected from:

| Mutation | | | | |
|---|---|---|---|---|
| S4X | C276X | G542X | R792X | E1104X |
| G27X | Q290X | G550X | E822X | R1158X |
| Q39X | G330X | Q552X | W846X | R1162X |
| W57X | W401X | R553X | Y849X | S1196X |
| E60X | Q414X | E585X | R851X | W1204X |
| R75X | S434X | G673X | Q890X | L1254X |
| E92X | S466X | Q685X | S912X | S1255X |
| Q98X | S489X | R709X | Y913X | W1282X |
| Y122X | Q493X | K710X | W1089X | Q1313X |
| E193X | W496X | L732X | Y1092X | E1371X |
| L218X | C524X | R764X | W1098X | Q1382X |
| Q220X | Q525X | R785X | R1102X | Q1411X |
| 185+1G→T | 711+5G→A | 1717-8G→A | 2622+1G→A | 3121-1G→A |
| 296+1G→A | 712-1G→T | 1717-1G→A | 2790-1G→C | 3500-2A→G |

-continued

| Mutation | | | | |
|---|---|---|---|---|
| 405+1G→A | 1248+1G→A | 1811+1G→C | 3040G→C | 3600+2insT |
| 405+3A→C | 1249-1G→A | 1811+1.6kbA→G | (G970R) | 3850-1G→A |
| 406-1G→A | 1341+1G→A | 1812-1G→A | 3120G→A | 4005+1G→A |
| 621+1G→T | 1525-2A→G | 1898+1G→A | 3120+1G→A | 4374+1G→T |
| 711+1G→T | 1525-1G→A | 1898+1G→C | 3121-2A→G | |
| 182delT | 1119delA | 1782delA | 2732insA | 3876delA |
| 306insA | 1138insG | 1824delA | 2869insG | 3878delG |
| 365-366insT | 1154insTC | 2043delG | 2896insAG | 3905insT |
| 394delTT | 1161delC | 2143delT | 2942insT | 4016insT |
| 442delA | 1213delT | 2183AA→G [a] | 2957delT | 4021dupT |
| 444delA | 1259insA | 2184delA | 3007delG | 4040delA |
| 457TAT→G | 1288insTA | 2184insA | 3028delA | 4279insA |
| 541delC | 1471delA | 2307insA | 3171delC | 4326delTC |
| 574delA | 1497delGG | 2347delG | 3659delC | |
| 663delT | 1548delG | 2585delT | 3737delA | |
| 935delA | 1609del CA | 2594delGT | 3791delC | |
| 1078delT | 1677delTA | 2711delT | 3821delT | |
| CFTRdele2, 3 | 1461ins4 | | 2991del32 | |
| CFTRdele22, 23 | 1924del7 | | 3667ins4 | |
| 124del23bp | 2055del9→A | | 4010del4 | |
| 852del22 | 2105-2117del13insAGAAA | | 4209TGTT→AA | |
| 991del5 | 2721del11 | | | |
| A46D[b] | V520F | Y569D[b] | N1303K | |
| G85E | A559T[b] | L1065P | | |
| R347P | R560T | R1066C | | |
| L467P[b] | R560S | L1077P[b] | | |
| I507del | A561E | M1101K | | |

213. The method according to embodiment 211, wherein the patient with a F508del/gating genotype has a gating mutation selected from G178R, S549N, S549R, G551D, G551S, G1244E, S1251N, S1255P, and G1349D.

214. The method according to embodiment 211, wherein the patient with a F508del/residual function genotype has a residual function mutation selected from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, K1060T, R117H, S1235R, I1027T, R668C, G576A, M470V, L997F, R75Q, R1070Q, R31C, D614G, G1069R, R1162L, E56K, A1067T, E193K, and K1060T.

215. The method according to any one of embodiments 201-214, wherein the absolute change in said patient's percent predicted forced expiratory volume in one second (ppFEV$_1$) after 15 days of administration of said at least one compound chosen from Compound I and pharmaceutically acceptable salts thereof; Compound II; and Compound III ranges from 3% to 40% relative to the ppFEV1 of the patient prior to said administration.

216. The method according to embodiment 211, wherein said patient has one F508del mutation and one minimal function mutation, and wherein patient has not taken any of said at least one compound chosen from Compound I and pharmaceutically acceptable salts thereof; Compound II; and Compound III.

217. The method according to embodiment 211, wherein said patient has two copies of F508del mutation, and wherein patient has taken Compound II and Compound III, but not any of said at least one compound chosen from Compound I and pharmaceutically acceptable salts thereof.

218. The method according to any one of embodiments 201-210, wherein said absolute change in said patient's ppFEV$_1$ ranges from 3% to 35%.

219. The method according to any one of embodiments 201-210, wherein said at least one compound chosen from Compound I and pharmaceutically acceptable salts thereof is comprised in a first pharmaceutical composition; said Compound II is comprised in a second pharmaceutical composition; and said Compound III or Compound III-d is comprised in a third pharmaceutical composition.

220. The method according to any one of embodiments 201-210, wherein said at least one compound chosen from Compound I and pharmaceutically acceptable salts thereof is comprised in a first pharmaceutical composition; and said Compound II and said Compound III or said Compound III and said Compound III-d are comprised in a second pharmaceutical composition.

221. The method according to embodiment 216, wherein said second pharmaceutical composition comprises a half of the daily dose of said Compound III, and the other half of the daily dose of Compound III is administered to said patient in a third pharmaceutical composition.

222. The method according to any one of embodiments 201-210, wherein said at least one compound chosen from Compound I and pharmaceutically acceptable salts thereof is comprised in a first pharmaceutical composition; said Compound II is comprised in a second pharmaceutical composition; and said Compound III or Compound III-d is comprised in the first pharmaceutical composition.

223. The method according to any one of embodiments 201-210, wherein said at least one compound chosen from Compound I and pharmaceutically acceptable salts thereof; said Compound II; and said Compound III or Compound III-d are comprised in a first pharmaceutical composition.

224. The method according to embodiment 219, wherein the first pharmaceutical composition is administered to the patient twice daily.

225. The method according to any one of embodiments 181-191, wherein the absolute change in said patient's percent predicted forced expiratory volume in one second (ppFEV1) after 15 days of administration of said at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof ranges from 3% to 40% relative to the ppFEV1 of the patient prior to said administration.

226. The method according to any one of embodiments 181-193 and 225, wherein said absolute change in said patient's ppFEV1 ranges from 3% to 35%.

227. The method according to any one of embodiments 201-210, wherein the absolute change in said patient's percent predicted forced expiratory volume in one second (ppFEV1) after 15 days of administration of said at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof ranges from 3% to 40% relative to the ppFEV1 of the patient prior to said administration.

228. The method according to any one of embodiment 201-210 and 227, wherein said absolute change in said patient's ppFEV1 ranges from 3% to 35%.

Methods of Preparing Compounds

General Experimental Procedures

Reagents and starting materials were obtained by commercial sources unless otherwise stated and were used without purification. Proton and carbon NMR spectra were acquired on either of a Bruker Biospin DRX 400 MHz FTNMR spectrometer operating at a $^1H$ and $^{13}C$ resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters. Final purity of compounds was determined by reversed phase UPLC using an Acquity UPLC BEH C18 column (50×2.1 mm, 1.7 μm particle) made by Waters (pn: 186002350), and a dual gradient run from 1-99% mobile phase B over 3.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were obtained using a single quadrupole mass spectrometer with a mass accuracy of 0.1 Da and a minimum resolution of 1000 amu across the detection range using electrospray ionization (ESI) using the hydrogen ion ($H^+$). Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30 m×0.25 mm×0.25 um_df) column, with a 2.0 mL/min flow rate ($H_2$ carrier gas), at an injection temperature of 220° C. and an oven temperature of 120° C., 15 minutes. Compounds I, II, III, and III-d can be prepared by any suitable method in the art, for example, PCT Publication Nos. WO 2011/133751 and WO 2015/160787 and U.S. Pat. No. 8,865,902.

Example 1: Synthesis of Compound I

Part A: Synthesis of (4S)-2,2,4-trimethylpyrrolidine hydrochloride

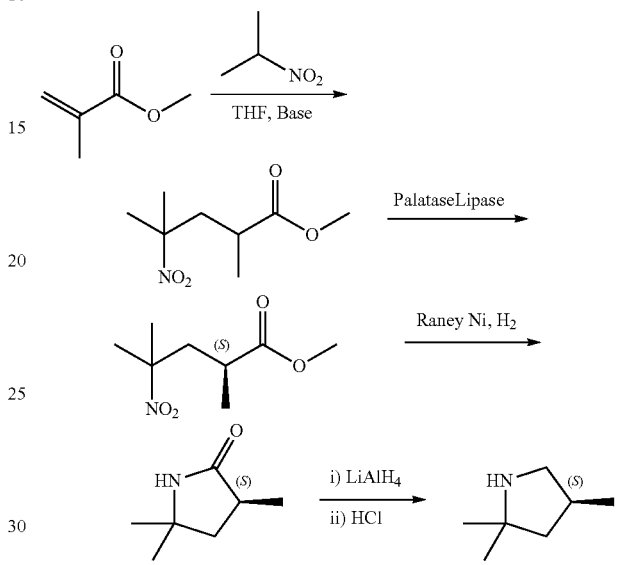

Step 1: Synthesis of methyl-2,4-dimethyl-4-nitro-pentanoate

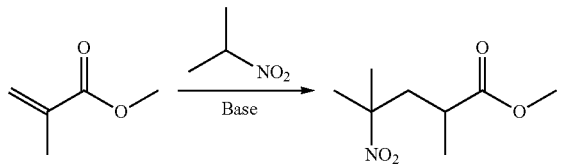

Tetrahydrofuran (THF, 4.5 L) was added to a 20 L glass reactor and stirred under $N_2$ at room temperature. 2-Nitropropane (1.5 kg, 16.83 mol) and 1,8-diazabicyclo[5.4.0]undec-7-ene (DBU) (1.282 kg, 8.42 mol) were then charged to the reactor, and the jacket temperature was increased to 50° C. Once the reactor contents were close to 50° C., methyl methacrylate (1.854 kg, 18.52 mol) was added slowly over 100 minutes. The reaction temperature was maintained at or close to 50° C. for 21 hours. The reaction mixture was concentrated in vacuo then transferred back to the reactor and diluted with methyl tert-butyl ether (MTBE) (14 L). 2 M HCl (7.5 L) was added, and this mixture was stirred for 5 minutes then allowed to settle. Two clear layers were visible—a lower yellow aqueous phase and an upper green organic phase. The aqueous layer was removed, and the organic layer was stirred again with 2 M HCl (3 L). After separation, the HCl washes were recombined and stirred with MTBE (3 L) for 5 minutes. The aqueous layer was removed, and all of the organic layers were combined in the reactor and stirred with water (3 L) for 5 minutes. After separation, the organic layers were concentrated in vacuo to afford a cloudy green oil. This was dried with MgSO$_4$ and filtered to afford methyl-2,4-dimethyl-4-nitro-pentanoate as a clear green oil (3.16 kg, 99% yield). $^1$H NMR (400 MHz, Chloroform-d) δ 3.68 (s, 3H), 2.56-2.35 (m, 2H), 2.11-2.00 (m, 1H), 1.57 (s, 3H), 1.55 (s, 3H), 1.19 (d, J=6.8 Hz, 3H).

Step 2: Synthesis of methyl (2S)-2,4-dimethyl-4-nitro-pentanoate

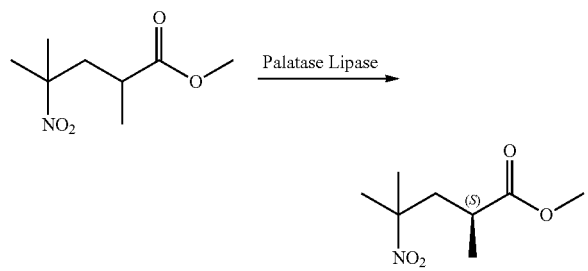

A reactor was charged with purified water (2090 L; 10 vol) and then potassium phosphate monobasic (27 kg, 198.4 moles; 13 g/L for water charge). The pH of the reactor contents was adjusted to pH 6.5 (±0.2) with 20% (w/v) potassium carbonate solution. The reactor was charged with racemic methyl-2,4-dimethyl-4-nitro-pentanoate (209 kg; 1104.6 moles), and Palatase 20000 L lipase (13 L, 15.8 kg; 0.06 vol).

The reaction mixture was adjusted to 32±2° C. and stirred for 15-21 hours, and pH 6.5 was maintained using a pH stat with the automatic addition of 20% potassium carbonate solution. When the racemic starting material was converted to >98% ee of the S-enantiomer, as determined by chiral GC, external heating was switched off. The reactor was then charged with MTBE (35 L; 5 vol), and the aqueous layer was extracted with MTBE (3 times, 400-1000 L). The combined organic extracts were washed with aqueous Na$_2$CO$_3$ (4 times, 522 L, 18% w/w 2.5 vol), water (523 L; 2.5 vol), and 10% aqueous NaCl (314 L, 1.5 vol). The organic layer was concentrated in vacuo to afford methyl (2S)-2,4-dimethyl-4-nitro-pentanoate as a mobile yellow oil (>98% ee, 94.4 kg; 45% yield).

Step 3: Synthesis of (3S)-3,5,5-trimethylpyrrolidin-2-one

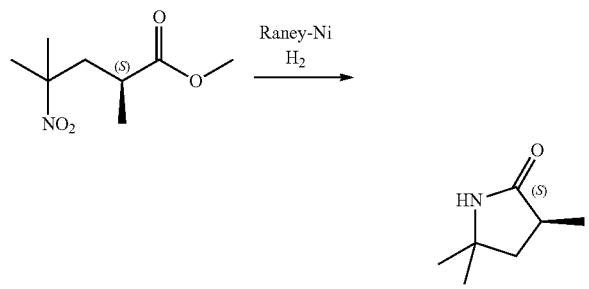

A 20 L reactor was purged with N2. The vessel was charged sequentially with DI water-rinsed, damp Raney® Ni (2800 grade, 250 g), methyl (2S)-2,4-dimethyl-4-nitro-pentanoate (1741 g, 9.2 mol), and ethanol (13.9 L, 8 vol). The reaction was stirred at 900 rpm, and the reactor was flushed with H$_2$ and maintained at ~2.5 bar. The reaction mixture was then warmed to 60° C. for 5 hours. The reaction mixture was cooled and filtered to remove Raney nickel, and the solid cake was rinsed with ethanol (3.5 L, 2 vol). The ethanolic solution of the product was combined with a second equal sized batch and concentrated in vacuo to reduce to a minimum volume of ethanol (~1.5 volumes). Heptane (2.5 L) was added, and the suspension was concentrated again to ~1.5 volumes. This was repeated 3 times; the resulting suspension was cooled to 0-5° C., filtered under suction, and washed with heptane (2.5 L). The product was dried under vacuum for 20 minutes then transferred to drying trays and dried in a vacuum oven at 40° C. overnight to afford (3S)-3,5,5-trimethylpyrrolidin-2-one as a white crystalline solid (2.042 kg, 16.1 mol, 87%). $^1$H NMR (400 MHz, Chloroform-d) δ 6.39 (s, 1H), 2.62 (ddq, J=9.9, 8.6, 7.1 Hz, 1H), 2.17 (dd, J=12.4, 8.6 Hz, 1H), 1.56 (dd, J=12.5, 9.9 Hz, 1H), 1.31 (s, 3H), 1.25 (s, 3H), 1.20 (d, J=7.1 Hz, 3H).

Step 4: Synthesis of (4S)-2,2,4-trimethylpyrrolidine hydrochloride

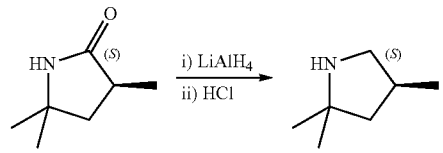

A glass lined 120 L reactor was charged with lithium aluminium hydride pellets (2.5 kg, 66 mol) and dry THF (60 L) and warmed to 30° C. The resulting suspension was charged with (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C., then cautiously quenched with the addition of ethyl acetate (EtOAc) (1.0 L, 10 moles), followed by a mixture of THF (3.4 L) and water (2.5 kg, 2.0 eq), and then a mixture of water (1.75 kg) with 50% aqueous sodium hydroxide (750 g, 2 equiv water with 1.4 equiv sodium hydroxide relative to aluminum), followed by 7.5 L water. After the addition was complete, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C. The resultant solution was concentrated by vacuum distillation to a slurry. Isopropanol (8 L) was added and the solution was concentrated to near dryness by vacuum distillation. Isopropanol (4 L) was added, and the product was slurried by warming to about 50° C. MTBE (6 L) was added, and the slurry was cooled to 2-5° C. The product was collected by filtration and rinsed with 12 L MTBE and dried in a vacuum oven (55° C./300 torr/N$_2$ bleed) to afford (4S)-2,2,4-trimethylpyrrolidine.HCl as a white, crystalline solid (6.21 kg, 75% yield). $^1$H NMR (400 MHz, DMSO-d6) δ 9.34 (br d, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Part B: Synthesis of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound I)

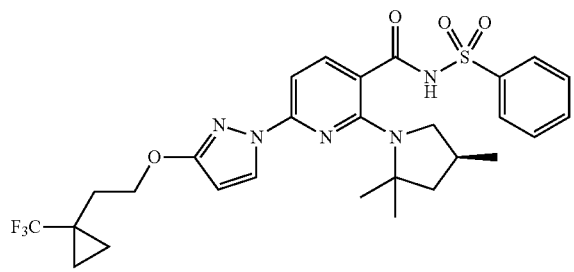

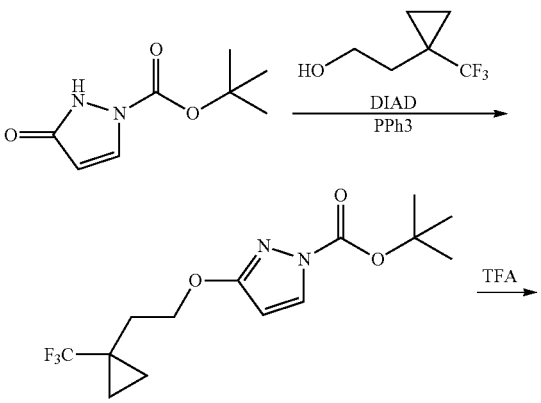

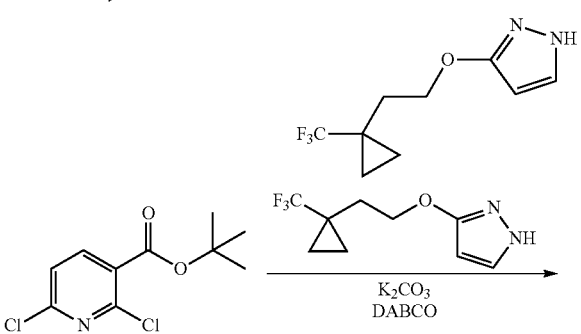

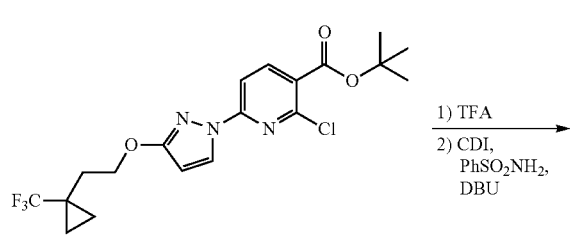

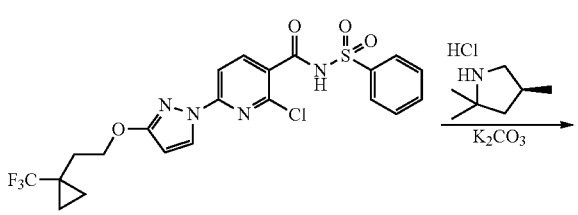

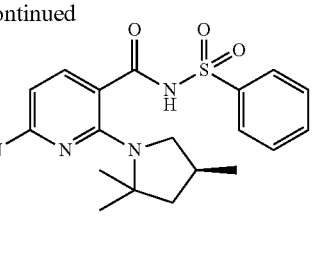

Synthesis of Starting Materials:

Synthesis of tert-Butyl 2,6-dichloropyridine-3-carboxylate

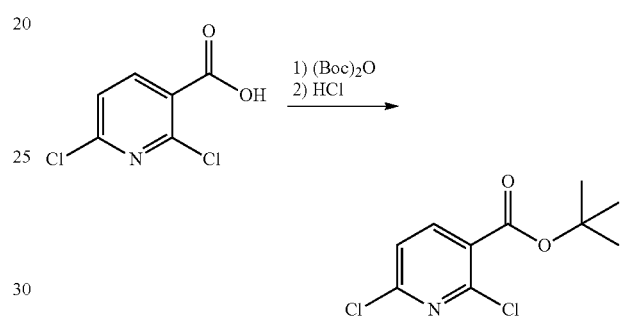

A solution of 2,6-dichloropyridine-3-carboxylic acid (10 g, 52.08 mmol) in THF (210 mL) was treated successively with di-tert-butyl dicarbonate (17 g, 77.89 mmol) and 4-(dimethylamino)pyridine (3.2 g, 26.19 mmol) and stirred overnight at room temperature. At this point, HCl 1N (400 mL) was added, and the mixture was stirred vigorously for about 10 minutes. The product was extracted with ethyl acetate (2×300 mL), and the combined organic layers were washed with water (300 mL) and brine (150 mL) and dried over sodium sulfate and concentrated under reduced pressure to give 12.94 g (96% yield) of tert-butyl 2,6-dichloropyridine-3-carboxylate as a colorless oil. ESI-MS m/z calc. 247.02, found 248.1 (M+1)$^+$; Retention time: 2.27 minutes. $^1$H NMR (300 MHz, CDCl$_3$) ppm 1.60 (s, 9H), 7.30 (d, J=7.9 Hz, 1H), 8.05 (d, J=8.2 Hz, 1H).

Synthesis of tert-Butyl 3-oxo-2,3-dihydro-1H-pyrazole-1-carboxylate

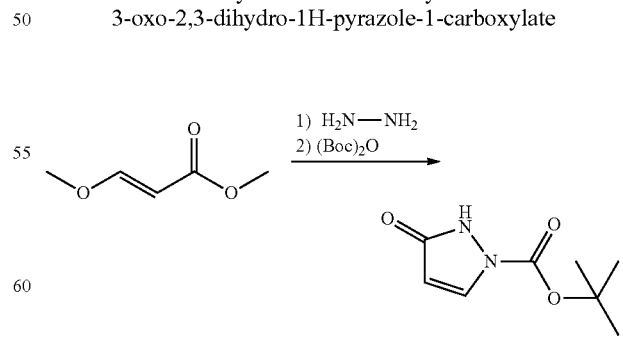

A 50 L Syrris controlled reactor was started, and the jacket was set to 20° C., with stirring at 150 rpm, reflux condenser (10° C.) and nitrogen purge. MeOH (2.860 L) and methyl (E)-3-methoxyprop-2-enoate (2.643 kg, 22.76 mol) were added, and the reactor was capped. The reaction was heated to an internal temperature of 40° C., and the system was set to hold jacket temp at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethyamine (2.483 kg, 3.420 L, 24.54 mol) was added portion-wise, maintaining reaction temp <30° C. A solution of boc anhydride (4.967 kg, 5.228 L, 22.76 mol) in MeOH (2.860 L) was added portion-wise maintaining temperature <45° C. The reaction mixture was stirred at 20° C. for 16 h. The reaction solution was partially concentrated to remove MeOH, resulting in a clear, light amber oil. The resulting oil was transferred to the 50 L reactor, stirred and water (7.150 L) and heptane (7.150 L) were added. The additions caused a small amount of the product to precipitate. The aqueous layer was drained into a clean container, and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol) and added dropwise. The jacket was set to 0° C. to absorb the quench exotherm. After the addition was complete (pH=5), the reaction mixture was stirred for 1 h. The solid was collected by filtration and washed with water (7.150 L), and washed a second time with water (3.575 L). The crystalline solid was transferred into a 20 L rotovap bulb, and heptane (7.150 L) was added. The mixture was slurried at 45° C. for 30 mins, and 1-2 volumes of solvent were distilled off. The slurry in the rotovap flask was filtered, and the solids were washed with heptane (3.575 L). The solid was further dried in vacuo (50° C., 15 mbar) to give tert-butyl 5-oxo-1H-pyrazole-2-carboxylate (2921 g, 71%) as a coarse, crystalline solid. $^1$H NMR (400 MHz, DMSO-d6) δ 10.95 (s, 1H), 7.98 (d, J=2.9 Hz, 1H), 5.90 (d, J=2.9 Hz, 1H), 1.54 (s, 9H).

Synthesis of 2-[1-(trifluoromethyl)cyclopropyl]ethanol

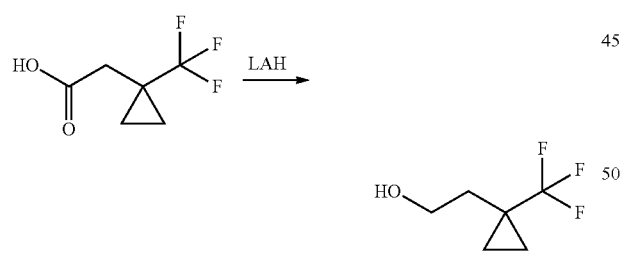

To a solution of lithium aluminum hydride (293 mg, 7.732 mmol) in THF (10.00 mL) in an ice-bath, 2-[1-(trifluoromethyl)cyclopropyl]acetic acid (1.002 g, 5.948 mmol) in THF (3.0 mL) was added dropwise over a period of 30 minutes keeping the reaction temperature below 20° C. The mixture was allowed to gradually warm to ambient temperature and was stirred for 18 h. The mixture was cooled with an ice-bath and sequentially quenched with water (294 mg, 295 µL, 16.36 mmol), NaOH (297 µL of 6 M, 1.784 mmol), and then water (884.0 µL, 49.07 mmol) to afford a granular solid in the mixture. The solid was filtered off using celite, and the precipitate was washed with ether. The filtrate was further dried with MgSO$_4$ and filtered and concentrated in vacuo to afford the product with residual THF and ether. The mixture was taken directly into the next step without further purification.

Step 1: tert-Butyl 3-[2-[1-(trifluoromethyl)cyclopropyl]ethoxy]pyrazole-1-carboxylate

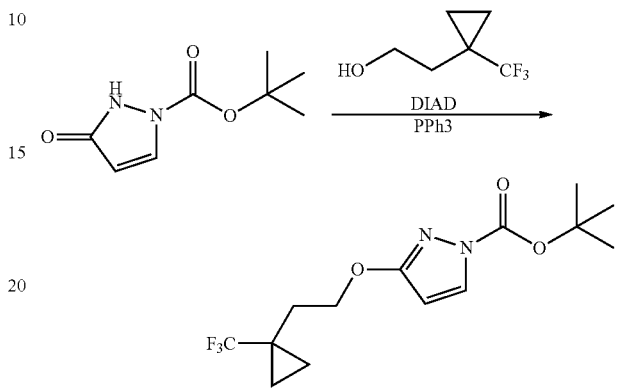

tert-Butyl 5-oxo-1H-pyrazole-2-carboxylate (1.043 g, 5.660 mmol), 2-[1-(trifluoromethyl)cyclopropyl]ethanol (916 mg, 5.943 mmol), and triphenyl phosphine (1.637 g, 6.243 mmol) were combined in THF (10.48 mL) and the reaction was cooled in an ice-bath. Diisopropyl azodicarboxylate (1.288 g, 1.254 mL, 6.368 mmol) was added dropwise to the reaction mixture, and the reaction was allowed to warm to room temperature for 16 hours. The mixture was evaporated, and the resulting material was partitioned between ethyl acetate (30 mL) and 1N sodium hydroxide (30 mL). The organic layer was separated, washed with brine (30 mL), dried over sodium sulfate, and concentrated. The crude material was purified by silica gel chromatography eluting with a gradient of ethyl acetate in hexanes (0-30%) to give tert-butyl 3-[2-[1-(trifluoromethyl)cyclopropyl]ethoxy]pyrazole-1-carboxylate (1.03 g, 57%). ESI-MS m/z calc. 320.13, found 321.1 (M+1)$^+$; Retention time: 0.72 minutes.

Step 2: 3-[2-[1-(Trifluoromethyl)cyclopropyl]ethoxy]-1H-pyrazole

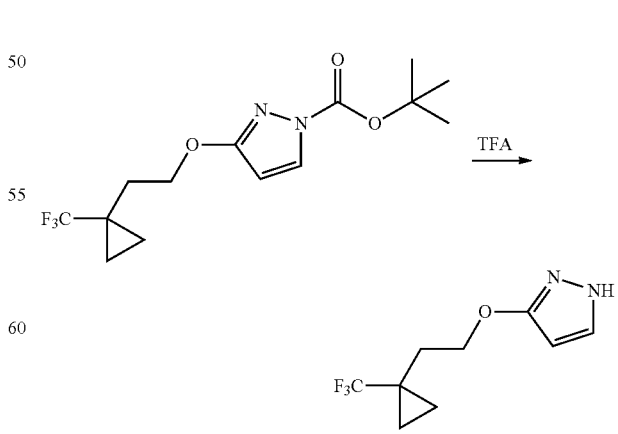

tert-Butyl-3-[2-[1-(trifluoromethyl)cyclopropyl]ethoxy] pyrazole-1-carboxylate (1.03 g, 3.216 mmol) was dissolved in dichloromethane (10.30 mL) with trifluoroacetic acid (2.478 mL, 32.16 mmol), and the reaction was stirred at room temperature for 2 hours. The reaction was evaporated, and the resulting oil was partitioned between ethyl acetate (10 mL) and a saturated sodium bicarbonate solution. The organic layer was separated, washed with brine, dried over sodium sulfate, and evaporated to give 3-[2-[1-(trifluoromethyl)cyclopropyl]ethoxy]-1H-pyrazole (612 mg, 86%). ESI-MS m/z calc. 220.08, found 221.0 (M+1)+; Retention time: 0.5 minutes. $^1$H NMR (400 MHz, DMSO-d6) δ 11.86 (s, 1H), 7.50 (t, J=2.1 Hz, 1H), 5.63 (t, J=2.3 Hz, 1H), 4.14 (t, J=7.1 Hz, 2H), 2.01 (t, J=7.1 Hz, 2H), 0.96-0.88 (m, 2H), 0.88-0.81 (m, 2H).

Step 3: tert-Butyl 2-chloro-6-[3-[2-[1-(trifluoromethyl)cyclopropyl]ethoxy]pyrazol-1-yl]pyridine-3-carboxylate

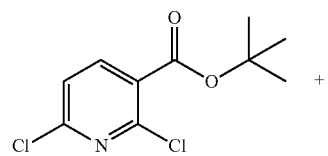
+
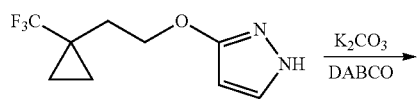
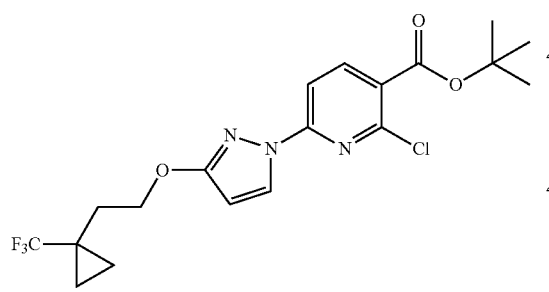

tert-Butyl 2,6-dichloropyridine-3-carboxylate (687 mg, 2.770 mmol), 3-[2-[1-(trifluoromethyl)cyclopropyl]ethoxy]-1H-pyrazole (610 mg, 2.770 mmol), and freshly ground potassium carbonate (459 mg, 3.324 mmol) were combined in anhydrous DMSO (13.75 mL). 1,4-diazabicyclo[2.2.2]octane (DABCO, 62 mg, 0.5540 mmol) was added, and the mixture was stirred at room temperature under nitrogen for 16 hours. The reaction mixture was diluted with water (20 mL) and stirred for 15 minutes. The resulting solid was collected and washed with water. The solid was dissolved in dichloromethane and dried over magnesium sulfate. The mixture was filtered and concentrated to give tert-butyl 2-chloro-6-[3-[2-[1-(trifluoromethyl)cyclopropyl]ethoxy]pyrazol-1-yl]pyridine-3-carboxylate (1.01 g, 84%). ESI-MS m/z calc. 431.12, found 432.1 (M+1)+; Retention time: 0.88 minutes.

Step 4: 2-Chloro-6-[3-[2-[1-(trifluoromethyl)cyclopropyl]ethoxy]pyrazol-1-yl]pyridine-3-carboxylic acid

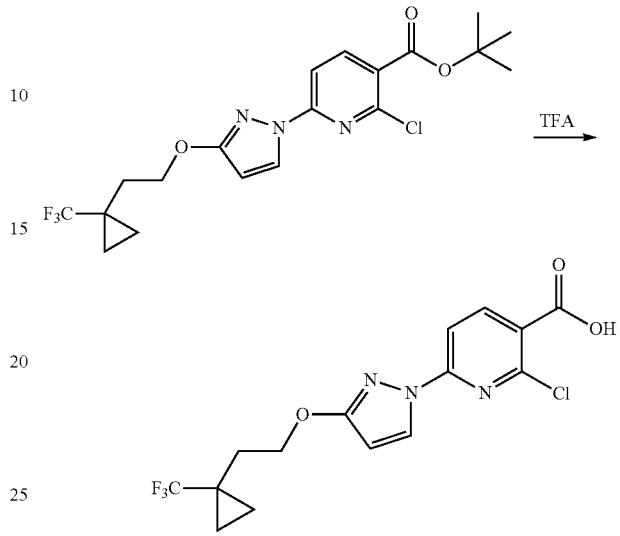

tert-Butyl 2-chloro-6-[3-[2-[1-(trifluoromethyl)cyclopropyl]ethoxy]pyrazol-1-yl]pyridine-3-carboxylate (1.01 g, 2.339 mmol) and trifluoroacetic acid (1.8 mL, 23.39 mmol) were combined in dichloromethane (10 mL) and heated at 40° C. for 3 h. The reaction was concentrated. Hexanes were added, and the mixture was concentrated again to give 2-chloro-6-[3-[2-[1-(trifluoromethyl)cyclopropyl]ethoxy]pyrazol-1-yl]pyridine-3-carboxylic acid (873 mg, 99%) ESI-MS m/z calc. 375.06, found 376.1 (M+1)+; Retention time: 0.69 minutes.

Step 5: N-(Benzenesulfonyl)-2-chloro-6-[3-[2-[1-(trifluoromethyl)cyclopropyl]ethoxy]pyrazol-1-yl]pyridine-3-carboxamide

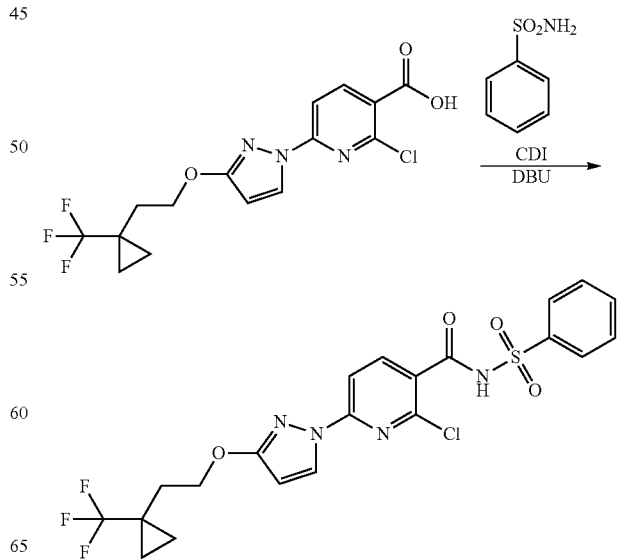

A solution of 2-chloro-6-[3-[2-[1-(trifluoromethyl)cyclopropyl]ethoxy]pyrazol-1-yl]pyridine-3-carboxylic acid (0.15 g, 0.3992 mmol) and carbonyl diimidazole (77 mg, 0.4790 mmol) in THF (2.0 mL) was stirred for one hour, and benzenesulfonamide (81 mg, 0.5190 mmol) and DBU (72 µL, 0.4790 mmol) were added. The reaction was stirred for 16 hours, acidified with 1 M aqueous citric acid, and extracted with ethyl acetate. The combined extracts were dried over sodium sulfate and evaporated. The residue was purified by silica gel chromatography eluting with a gradient of methanol in dichloromethane (0-5%) to give N-(benzenesulfonyl)-2-chloro-6-[3-[2-[1-(trifluoromethyl)cyclopropyl]ethoxy]pyrazol-1-yl]pyridine-3-carboxamide (160 mg, 78%). ESI-MS m/z calc. 514.07, found 515.1 (M+1)$^+$; Retention time: 0.74 minutes.

Step 6: N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

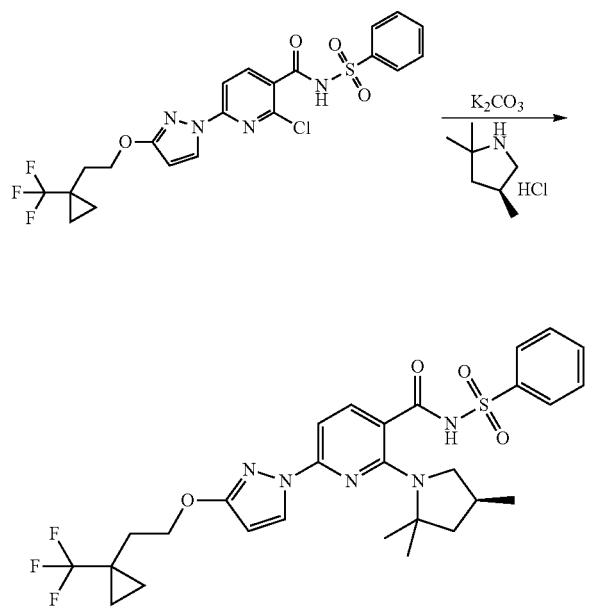

A mixture of N-(benzenesulfonyl)-2-chloro-6-[3-[2-[1-(trifluoromethyl)cyclopropyl] ethoxy]pyrazol-1-yl]pyridine-3-carboxamide (160 mg, 0.3107 mmol), (4S)-2,2,4-trimethylpyrrolidine hydrochloride salt (139 mg, 0.9321 mmol), and potassium carbonate (258 mg, 1.864 mmol) in DMSO (1.5 mL) was stirred at 130° C. for 17 hours. The reaction mixture was acidified with 1 M aqueous citric acid and extracted with ethyl acetate. The combined extracts were dried over sodium sulfate and evaporated to yield a crude product that was purified by reverse-phase HPLC utilizing a gradient of 10-99% acetonitrile in 5 mM aqueous HCl to yield N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (87 mg, 47%). ESI-MS m/z calc. 591.21, found 592.3 (M+1)$^+$; Retention time: 2.21 minutes. $^1$H NMR (400 MHz, DMSO-d6) δ 12.48 (s, 1H), 8.19 (d, J=2.8 Hz, 1H), 8.04-7.96 (m, 2H), 7.81 (d, J=8.2 Hz, 1H), 7.77-7.70 (m, 1H), 7.70-7.62 (m, 2H), 6.92 (d, J=8.2 Hz, 1H), 6.10 (d, J=2.8 Hz, 1H), 4.31 (t, J=7.0 Hz, 2H), 2.42 (t, J=10.5 Hz, 1H), 2.28 (dd, J=10.2, 7.0 Hz, 1H), 2.17-2.01 (m, 3H), 1.82 (dd, J=11.9, 5.5 Hz, 1H), 1.52 (d, J=9.4 Hz, 6H), 1.36 (t, J=12.1 Hz, 1H), 1.01-0.92 (m, 2H), 0.92-0.85 (m, 2H), 0.65 (d, J=6.3 Hz, 3H).

Preparation of a Spray Dried Dispersion (SDD) of Compound I

A spray dried dispersion of Compound I was prepared using Buchi Mini Spray Dryer B290. HPMCAS-HG (6.0 grams) was dissolved in 200 mL of MeOH/DCM (1/1), and Compound I (6.0 grams) was added and stirred for 30 minutes forming a clear solution. The resulting solution was spray dried under the following conditions resulting in a 50% Compound 1/50% HPMCAS-HG spray dried dispersion (Yield: 80%, Solid load: 6%).

| | Conditions |
|---|---|
| Inlet Temperature (° C.) | 77 |
| Outlet Temperature (° C.) | 39 |
| Nitrogen Pressure (PSI) | 95 |
| Aspirator (%) | 100 |
| Pump (%) | 30 |
| Rotameter (mm) | 60 |
| Filter Pressure (mBar) | −50 |
| Condenser Temperature (° C.) | −10 |

Powder X-Ray Diffraction

The powder x-ray diffraction measurements were performed using PANalytical's X-pert Pro diffractometer at room temperature with copper radiation (1.54060 Å). The incident beam optic was comprised of a variable divergence slit to ensure a constant illuminated length on the sample and on the diffracted beam side; a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s.

FIG. 1 shows the XRPD spectrum of a SDD of 50% Compound I in HPMCAS-HG, and shows that compound I is amorphous in the SDD.

Modulated Differential Scanning calorimetry (MDSC)

MDSC was used to determine the glass transition temperature of the amorphous material. MDSC was performed using TA Discovery DSC differential scanning calorimeter (TA Instruments, New Castle, Del.). The instrument was calibrated with indium. Samples of approximately 1-3 mg were weighed into hermetic pans that were crimped using lids with one hole. The MDSC sample was scanned from −20° C. to 210° C. at a heating rate of 2° C./min with +/−1° C. of modulation within 1 minute. Data was collected and analyzed by TA Instruments Trios Software (TA Instruments, New Castle, Del.).

Figure 2:
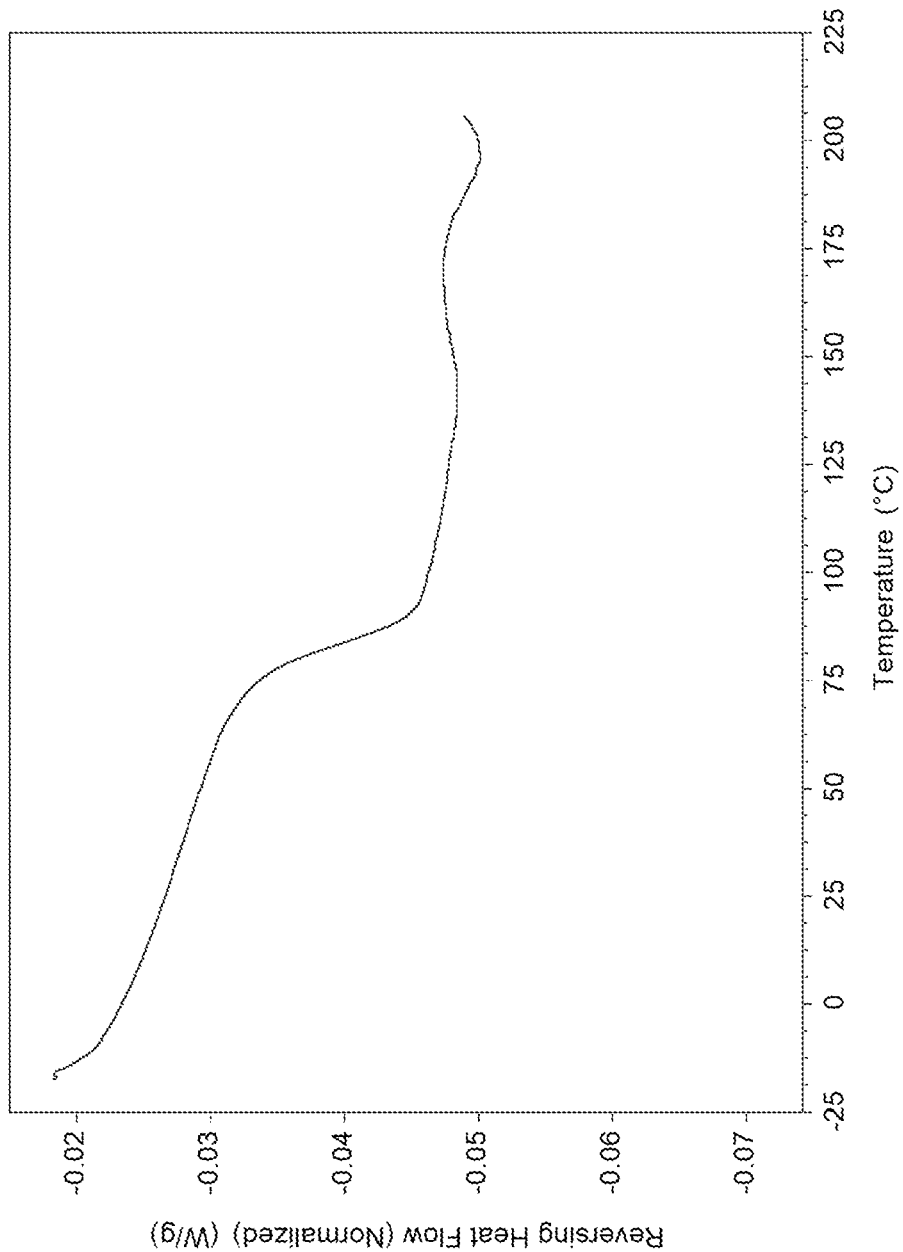
FIG. 2 is a Modulated Differential Scanning calorimetry (MDSC) spectrum of a spray dried dispersion of Compound I with HPMCAS-HG.

FIG. 2 shows a MDSC spectrum of a SDD of 50% Compound I in HPMCAS-HG, and shows that the SDD has an onset temperature of about 75.6° C., a midpoint temperature of about 82.7° C., and an offset temperature of about 89.7° C.

83

Example 2: Synthesis of Compound II: (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide

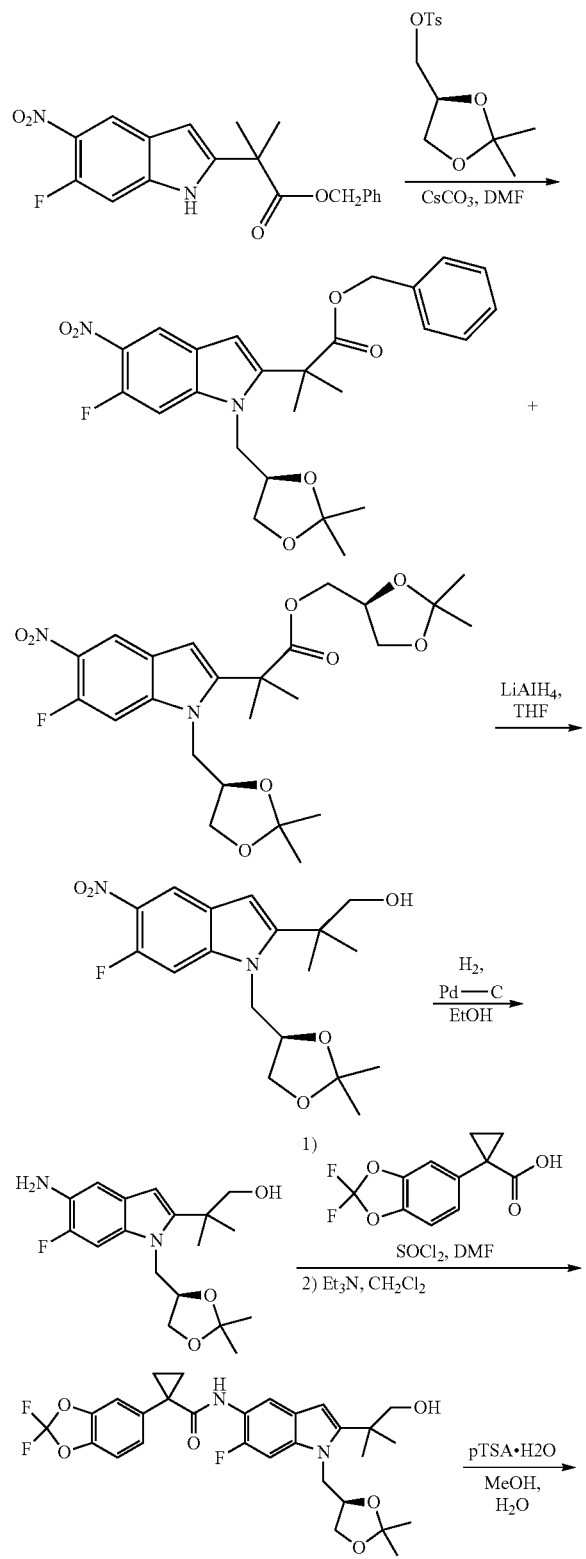

84

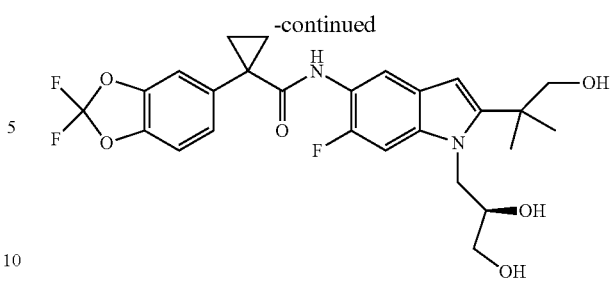

Step 1: (R)-Benzyl 2-(1-((2,2-dimethyl-1,3-dioxolan-4-yl)methyl)-6-fluoro-5-nitro-1H-indol-2-yl)-2-methylpropanoate and ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate Cesium carbonate (8.23 g, 25.3 mmol) was added to a mixture of benzyl 2-(6-fluoro-5-nitro-1H-indol-2-yl)-2-methylpropanoate (3.0 g, 8.4 mmol) and (S)-(2,2-dimethyl-1,3-dioxolan-4-yl)methyl 4-methylbenzenesulfonate (7.23 g, 25.3 mmol) in DMF (17 mL). The reaction was stirred at 80° C. for 46 hours under a nitrogen atmosphere. The mixture was then partitioned between ethyl acetate and water. The aqueous layer was extracted with ethyl acetate. The combined ethyl acetate layers were washed with brine, dried over MgSO4, filtered and concentrated. The crude product, a viscous brown oil which contains both of the products shown above, was taken directly to the next step without further purification. (R)-Benzyl 2-(1-((2,2-dimethyl-1,3-dioxolan-4-yl)methyl)-6-fluoro-5-nitro-1H-indol-2-yl)-2-methylpropanoate, ESI-MS m/z calc. 470.2, found 471.5 (M+1)$^+$. Retention time 2.20 minutes. ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate, ESI-MS m/z calc. 494.5, found 495.7 (M+1)$^+$. Retention time 2.01 minutes.

Step 2: (R)-2-(1-((2,2-dimethyl-1,3-dioxolan-4-yl)methyl)-6-fluoro-5-nitro-1H-indol-2-yl)-2-methylpropan-1-ol The crude reaction mixture obtained in step (A) was dissolved in THF (42 mL) and cooled in an ice-water bath. LiAlH4 (16.8 mL of 1 M solution, 16.8 mmol) was added drop-wise. After the addition was complete, the mixture was stirred for an additional 5 minutes. The reaction was quenched by adding water (1 mL), 15% NaOH solution (1 mL) and then water (3 mL). The mixture was filtered over Celite, and the solids were washed with THF and ethyl acetate. The filtrate was concentrated and purified by column chromatography (30-60% ethyl acetate-hexanes) to obtain (R)-2-(1-((2,2-dimethyl-1,3-dioxolan-4-yl)methyl)-6-fluoro-5-nitro-1H-indol-2-yl)-2-methylpropan-1-ol as a brown oil (2.68 g, 87% over 2 steps). ESI-MS m/z calc. 366.4, found 367.3 (M+1)$^+$. Retention time 1.68 minutes. $^1$H NMR (400 MHz, DMSO-d6) δ 8.34 (d, J=7.6 Hz, 1H), 7.65 (d, J=13.4 Hz, 1H), 6.57 (s, 1H), 4.94 (t, J=5.4 Hz, 1H), 4.64-4.60 (m, 1H), 4.52-4.42 (m, 2H), 4.16-4.14 (m, 1H), 3.76-3.74 (m, 1H), 3.63-3.53 (m, 2H), 1.42 (s, 3H), 1.38-1.36 (m, 6H) and 1.19 (s, 3H) ppm Step 3: (R)-2-(5-amino-1-((2,2-dimethyl-1,3-dioxolan-4-yl)methyl)-6-fluoro-1H-indol-2-yl)-2-methylpropan-1-ol (R)-2-(1-((2,2-dimethyl-1,3-dioxolan-4-yl)methyl)-6-fluoro-5-nitro-1H-indol-2-yl)-2-methylpropan-1-ol (2.5 g, 6.82 mmol) was dissolved in ethanol (70 mL) and the reaction was flushed with N₂. Then Pd—C (250 mg, 5% wt) was added. The reaction was flushed with nitrogen again and then stirred under H₂ (atm). After 2.5 hours only partial conversion to the product was observed by LCMS. The reaction was filtered through Celite and concentrated. The residue was re-subjected to the conditions above. After 2 hours LCMS indicated complete conversion to product. The reaction mixture was filtered through Celite. The filtrate was concentrated to yield the product as a black solid (1.82 g, 79%). ESI-MS m/z calc. 336.2, found 337.5 (M+1)⁺. Retention time 0.86 minutes. ¹H NMR (400 MHz, DMSO-d6) δ 7.17 (d, J=12.6 Hz, 1H), 6.76 (d, J=9.0 Hz, 1H), 6.03 (s, 1H), 4.79-4.76 (m, 1H), 4.46 (s, 2H), 4.37-4.31 (m, 3H), 4.06 (dd, J=6.1, 8.3 Hz, 1H), 3.70-3.67 (m, 1H), 3.55-3.52 (m, 2H), 1.41 (s, 3H), 1.32 (s, 6H) and 1.21 (s, 3H) ppm.

Step 4: (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide DMF (3 drops) was added to a stirring mixture of 1-(2,2-difluorobenzo[d][1,3]dioxol-5-yl)cyclopropanecarboxylic acid (1.87 g, 7.7 mmol) and thionyl chloride (1.30 mL, 17.9 mmol). After 1 hour a clear solution had formed. The solution was concentrated under vacuum and then toluene (3 mL) was added and the mixture was concentrated again. The toluene step was repeated once more and the residue was placed on high vacuum for 10 minutes. The acid chloride was then dissolved in dichloromethane (10 mL) and added to a mixture of (R)-2-(5-amino-1-((2,2-dimethyl-1,3-dioxolan-4-yl)methyl)-6-fluoro-1H-indol-2-yl)-2-methylpropan-1-ol (1.8 g, 5.4 mmol) and triethylamine (2.24 mL, 16.1 mmol) in dichloromethane (45 mL). The reaction was stirred at room temperature for 1 hour. The reaction was washed with 1N HCl solution, saturated NaHCO₃ solution and brine, dried over MgSO₄ and concentrated to yield the product as a black foamy solid (3 g, 100%). ESI-MS m/z calc. 560.6, found 561.7 (M+1)⁺. Retention time 2.05 minutes. ¹H NMR (400 MHz, DMSO-d6) δ 8.31 (s, 1H), 7.53 (s, 1H), 7.42-7.40 (m, 2H), 7.34-7.30 (m, 3H), 6.24 (s, 1H), 4.51-4.48 (m, 1H), 4.39-4.34 (m, 2H), 4.08 (dd, J=6.0, 8.3 Hz, 1H), 3.69 (t, J=7.6 Hz, 1H), 3.58-3.51 (m, 2H), 1.48-1.45 (m, 2H), 1.39 (s, 3H), 1.34-1.33 (m, 6H), 1.18 (s, 3H) and 1.14-1.12 (m, 2H) ppm Step 5: (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide (3.0 g, 5.4 mmol) was dissolved in methanol (52 mL). Water (5.2 mL) was added followed by p-TsOH.H₂O (204 mg, 1.1 mmol). The reaction was heated at 80° C. for 45 minutes. The solution was concentrated and then partitioned between ethyl acetate and saturated NaHCO₃ solution. The ethyl acetate layer was dried over MgSO₄ and concentrated. The residue was purified by column chromatography (50-100% ethyl acetate-hexanes) to yield the product as a cream colored foamy solid. (1.3 g, 47%, ee >98% by SFC). ESI-MS m/z calc. 520.5, found 521.7 (M+1)⁺. Retention time 1.69 minutes. ¹H NMR (400 MHz, DMSO-d6) δ 8.31 (s, 1H), 7.53 (s, 1H), 7.42-7.38 (m, 2H), 7.33-7.30 (m, 2H), 6.22 (s, 1H), 5.01 (d, J=5.2 Hz, 1H), 4.90 (t, J=5.5 Hz, 1H), 4.75 (t, J=5.8 Hz, 1H), 4.40 (dd, J=2.6, 15.1 Hz, 1H), 4.10 (dd, J=8.7, 15.1 Hz, 1H), 3.90 (s, 1H), 3.65-3.54 (m, 2H), 3.48-3.33 (m, 2H), 1.48-1.45 (m, 2H), 1.35 (s, 3H), 1.32 (s, 3H) and 1.14-1.11 (m, 2H) ppm.

Example 3: Synthesis of Compound III: N-(2,4-di-tert-butyl-5-hydroxyphenyl)-4-oxo-1,4-dihydroquinoline-3-carboxamide Part A: Synthesis of 4-oxo-1,4-dihydroquinoline-3-carboxylic acid

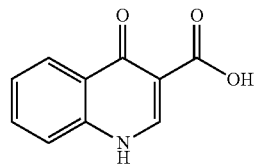 [SMILES: O=C(O)c1c[nH]c2ccccc2c1=O]

Step 1: 2-Phenylaminomethylene-malonic acid diethyl ester

A mixture of aniline (25.6 g, 0.275 mol) and diethyl 2-(ethoxymethylene)malonate (62.4 g, 0.288 mol) was heated at 140-150° C. for 2 h. The mixture was cooled to room temperature and dried under reduced pressure to afford 2-phenylaminomethylene-malonic acid diethyl ester as a solid, which was used in the next step without further purification. ¹H NMR (DMSO-d₆) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

Step 2: 4-Hydroxyquinoline-3-carboxylic acid ethyl ester

A 1 L three-necked flask fitted with a mechanical stirrer was charged with 2-phenylaminomethylene-malonic acid diethyl ester (26.3 g, 0.100 mol), polyphosphoric acid (270 g) and phosphoryl chloride (750 g). The mixture was heated to 70° C. and stirred for 4 h. The mixture was cooled to room temperature and filtered. The residue was treated with aqueous Na₂CO₃ solution, filtered, washed with water and dried. 4-Hydroxyquinoline-3-carboxylic acid ethyl ester was obtained as a pale brown solid (15.2 g, 70%). The crude product was used in next step without further purification.

Step 3: 4-Oxo-1,4-dihydroquinoline-3-carboxylic acid

4-Hydroxyquinoline-3-carboxylic acid ethyl ester (15 g, 69 mmol) was suspended in sodium hydroxide solution (2N, 150 mL) and stirred for 2 h at reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid as a pale white solid (10.5 g, 92%). ¹H NMR (DMSO-d₆) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

Part B: Synthesis of N-(2,4-di-tert-butyl-5-hydroxy-phenyl)-4-oxo-1,4-dihydroquinoline-3-carboxamide

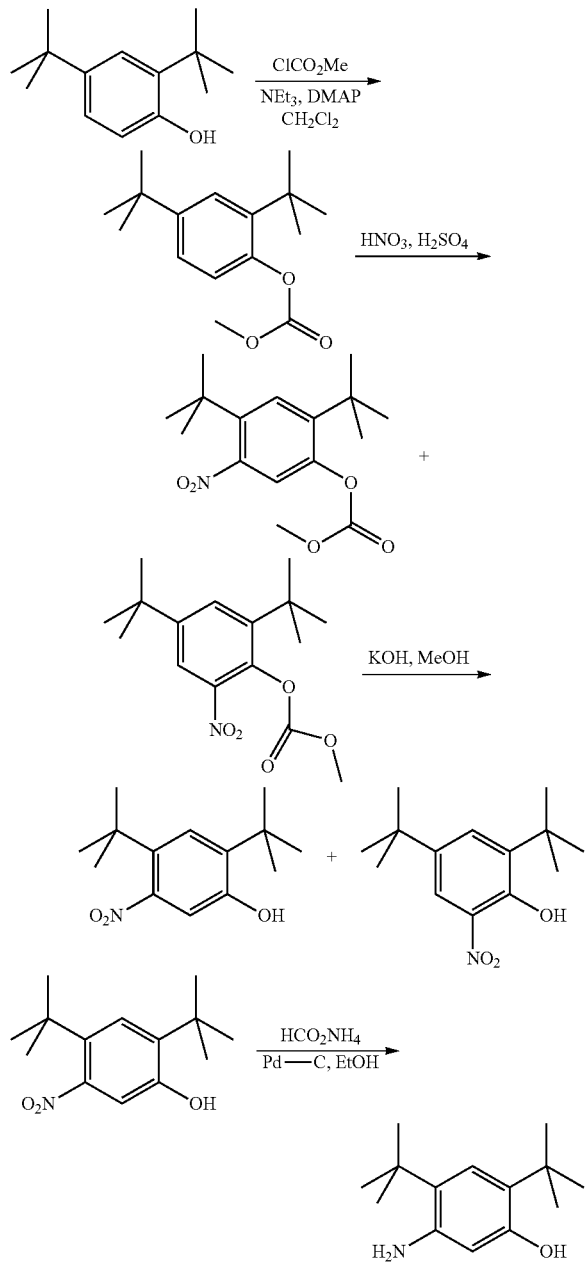

Step 1: Carbonic acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), Et$_3$N (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate-hexanes (~4 L) as the eluent. The combined filtrates were concentrated to yield carbonic acid 2,4-di-tert-butyl-phenyl ester methyl ester as a yellow oil (132 g, quant.). $^1$H NMR (400 MHz, DMSO-d$_6$) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Step 2: Carbonic acid 2,4-di-tert-butyl-5-nitro-phenyl ester methyl ester and Carbonic acid 2,4-di-tert-butyl-6-nitro-phenyl ester methyl ester To a stirring mixture of carbonic acid 2,4-di-tert-butyl-phenyl ester methyl ester (4.76 g, 180 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried (MgSO$_4$), concentrated and purified by column chromatography (0-10% ethyl acetate-hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

Step 3: 2,4-Di-tert-butyl-5-nitro-phenol and 2,4-Di-tert-butyl-6-nitro-phenol

The mixture of carbonic acid 2,4-di-tert-butyl-5-nitro-phenyl ester methyl ester and carbonic acid 2,4-di-tert-butyl-6-nitro-phenyl ester methyl ester (4.2 g, 14.0 mmol) was dissolved in MeOH (65 mL) before KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO$_4$), concentrated and purified by column chromatography (0-5% ethyl acetate-hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: $^1$H NMR (400 MHz, DMSO-d$_6$) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: $^1$H NMR (400 MHz, CDCl$_3$) δ 11.48 (s, 1H), 7.98 (d, J=2.5 Hz, 1H), 7.66 (d, J=2.4 Hz, 1H), 1.47 (s, 9H), 1.34 (s, 9H).

Step 4: 5-Amino-2,4-di-tert-butyl-phenol

To a refluxing solution of 2,4-di-tert-butyl-5-nitro-phenol (1.86 g, 7.40 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-d$_6$) δ 8.64 (s, 1H, OH), 6.84 (s, 1H), 6.08 (s, 1H), 4.39 (s, 2H, NH$_2$), 1.27 (m, 18H); HPLC ret. time 2.72 min, 10-99% CH$_3$CN, 5 min run; ESI-MS 222.4 m/z [M+H]$^+$.

Step 5: N-(5-hydroxy-2,4-di-tert-butyl-phenyl)-4-oxo-1H-quinoline-3-carboxamide

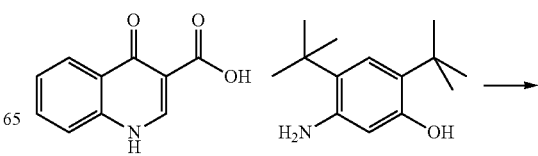

-continued

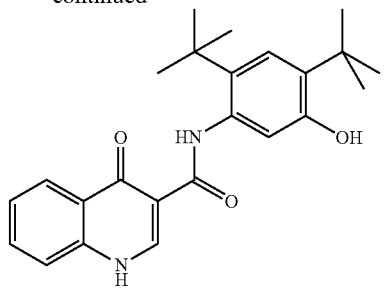

To a suspension of 4-oxo-1,4-dihydroquinolin-3-carboxylic acid (35.5 g, 188 mmol) and HBTU (85.7 g, 226 mmol) in DMF (280 mL) was added Et$_3$N (63.0 mL, 451 mmol) at ambient temperature. The mixture became homogeneous and was allowed to stir for 10 min before 5-amino-2,4-di-tert-butyl-phenol (50.0 g, 226 mmol) was added in small portions. The mixture was allowed to stir overnight at ambient temperature. The mixture became heterogeneous over the course of the reaction. After all of the acid was consumed (LC-MS analysis, MH+ 190, 1.71 min), the solvent was removed in vacuo. EtOH was added to the orange solid material to produce a slurry. The mixture was stirred on a rotovap (bath temperature 65° C.) for 15 min without placing the system under vacuum. The mixture was filtered and the captured solid was washed with hexanes to provide a white solid that was the EtOH crystalate. Et$_2$O was added to the solid obtained above until a slurry was formed. The mixture was stirred on a rotovapor (bath temperature 25° C.) for 15 min without placing the system under vacuum. The mixture was filtered and the solid captured. This procedure was performed a total of five times. The solid obtained after the fifth precipitation was placed under vacuum overnight to provide N-(5-hydroxy-2,4-di-tert-butyl-phenyl)-4-oxo-1H-quinoline-3-carboxamide as a white powdery solid (38 g, 52%). HPLC ret. time 3.45 min, 10-99% CH$_3$CN, 5 min run; $^1$H NMR (400 MHz, DMSO-d$_6$) δ 12.88 (s, 1H), 11.83 (s, 1H), 9.20 (s, 1H), 8.87 (s, 1H), 8.33 (dd, J=8.2, 1.0 Hz, 1H), 7.83-7.79 (m, 1H), 7.76 (d, J=7.7 Hz, 1H), 7.54-7.50 (m, 1H), 7.17 (s, 1H), 7.10 (s, 1H), 1.38 (s, 9H), 1.37 (s, 9H); ESI-MS m/z calc'd 392.21; found 393.3 [M+H]$^+$.

Example 4: Synthesis of N-(2-(tert-Butyl)-4-(tert-butyl-d)-5-hydroxyphenyl)-4-oxo-1,4-dihydroquinoline-3-carboxamide (Compound III-d)

Step 1. 2-(tert-Butyl-d$_9$)-4-(tert-butyl)-6-d-phenol

To a solution of 4-tert-butyl phenol (3.43 g, 22.7 mmol) and tert-butyl alcohol-d10 (3.00 mL, 31.8 mmol, 98 atom % D, Cambridge Isotope Laboratories, Inc.) in dichloromethane (40.0 mL) was added D$_2$SO$_4$ (1.50 mL, 99.5 atom % D, Sigma-Aldrich). The reaction was stirred at room temperature for 15 hours then was diluted with water and extracted with dichloromethane (3×100 mL). The organic layers were combined, washed with saturated NaHCO$_3$, dried (Na$_2$SO$_4$), filtered, and concentrated in vacuo. The resulting oil was purified by column chromatography (SiO$_2$, 0-15% ethyl acetate/heptanes) to afford 2-(tert-Butyl-d$_9$)-4-(tert-butyl)-6-d-phenol (4.04 g, 83% yield) as a clear oil. $^1$HNMR (d$_6$-DMSO, 400 MHz) δ 9.04 (s, 1H), 7.12 (d, J=2.4 Hz, 1H), 6.98 (dd, J=3.8, 2.5 Hz, 1H), 6.67 (d, J=8.3 Hz, 0.3H), 1.22 (s, 10H).

Step 2. 2-(tert-Butyl-d$_9$)-4-(tert-butyl)-6-d-phenyl methyl carbonate

To a solution of 2-(tert-Butyl-d$_9$)-4-(tert-butyl)-6-d-phenol (4.04 g, 18.8 mmol), triethylamine (5.24 mL, 37.6 mmol) and N,N-dimethylaminopyridine (115 mg, 0.940 mmol) in CH$_2$Cl$_2$ (40.0 mL) at 0° C. was added methyl chloroformate (2.17 mL, 28.2 mmol). The reaction was stirred at room temperature for 15 hours and additional trimethylamine (1.30 mL, 9.33 mmol) and methyl chloroformate (0.550 mL, 7.15 mmol) were added. After stirring for an additional 1 hour the reaction was diluted with 10% ethyl acetate/heptanes and filtered through a silica plug. The silica plug was then rinsed with additional 10% ethyl acetate/heptanes. The filtrate was combined and concentrated in vacuo to provide 2-(tert-Butyl-d$_9$)-4-(tert-butyl)-6-d-phenyl methyl carbonate (4.69 g, 91% yield) as a light yellow oil which was carried forward without purification. $^1$H NMR (d$_6$-DMSO, 400 MHz) δ 7.33 (d, J=2.4 Hz, 1H), 7.30-7.20 (m, 1H), 7.06 (d, J=8.5 Hz, 0.3H), 3.84 (d, J=0.7 Hz, 3H), 1.28 (s, 9H).

Step 3. 2-(tert-Butyl-d$_9$)-4-(tert-butyl)-6-d-5-nitro-phenol

To a solution of 2-(tert-Butyl-d$_9$)-4-(tert-butyl)-6-d-phenyl methyl carbonate (4.69 g, 17.2 mmol) in sulfuric acid (2.00 mL) at 0° C. was added a 1:1 mixture of sulfuric acid and nitric acid (4.00 mL) dropwise. The reaction was then stirred at room temperature for two hours then slowly added to ice water with vigorous stirring. The resulting slurry was extracted with ethyl acetate (3×100 mL) and the combined organic layers were dried (Na$_2$SO$_4$), filtered, and concentrated to afford an amber oil containing a mixture of regioisomers. This crude oil was then taken up in MeOH (100 mL) and KOH (3.50 g) was added. The reaction was stirred at room temperature for 2 hours then was acidified to pH=2 with concentrated HCl. The resulting solution was extracted with diethyl ether (3×100 mL), dried (MgSO$_4$), filtered, and concentrated. The residue was then purified via column chromatography (SiO$_2$, 0-5% ethyl acetate/heptanes) to afford 2-(tert-Butyl-d$_9$)-4-(tert-butyl)-6-d-5-nitro-phenol (1.33 g, 30%) as a light yellow solid. MS (ESI) 260.2 [(M−H)$^-$].

Step 4. 5-Amino-2-(tert-butyl-d$_9$)-4-(tert-butyl)-6-d-phenol

A solution of 2-(tert-Butyl-d$_9$)-4-(tert-butyl)-6-d-5-nitro-phenol (1.33 g, 5.11 mmol) and ammonium formate (1.29 g, 20.4 mmol) in ethanol (60.0 mL) was heated to reflux. At this time, 10% Pd/C (650 mg, 50% wet) was added in small portions and the reaction continued to stir at reflux for two hours. The reaction was then cooled to room temperature, diluted with THF, filtered through Celite® and concentrated in vacuo to afford 5-Amino-2-(tert-butyl-d9)-4-(tert-butyl)-6-d-phenol (1.19 g, 100%) as a pink solid. MS (ESI) 232.3 [(M+H)$^+$].

Step 5. 5-Amino-2-(tert-butyl-d$_9$)-4-(tert-butyl)-phenol

5-Amino-2-(tert-butyl-d$_9$)-4-(tert-butyl)-6-dphenol (298 mg, 1.29 mmol) was dissolved in 5M HCl in 2-propanol (20 mL) and the reaction was stirred at room temperature for 15 hours. The reaction was then concentrated in vacuo and taken back up in 5M HCl in 2-propanol (20 mL). After stirring for an additional 15 hours at room temperature, the reaction was concentrated in vacuo and diluted with saturated aqueous sodium bicarbonate (100 mL). The resulting aqueous solution was extracted with dichloromethane (3×50 mL). The organic layers were combined, dried ($Na_2SO_4$), filtered and concentrated in vacuo to afford 5-Amino-2-(tert-butyl-$d_9$)-4-(tert-butyl)-phenol (240 mg, 81%) as a pink solid. $^1$H NMR ($d_6$-DMSO, 400 MHz) δ 8.62 (s, 1H), 6.83 (s, 1H), 6.08 (s, 1H), 1.27 (s, 9H).

Step 6. N-(2-(tert-Butyl)-4-(tert-butyl-$d_9$)-5-hydroxyphenyl)-4-oxo-1,4-dihydroquinoline-3-carboxamide (Compound III-d)

To a solution of 5-Amino-2-(tert-butyl-$d_9$)-4-(tert-butyl)-phenol (240 mg, 1.04 mmol), 4-oxo-1,4-dihydroquinoline-3-carboxylic acid (purchased from Matrix Scientific, 99 mg, 0.521 mmol) and N,N-diisopropylethylamine (181 μl, 1.04 mmol) in DMF (6.00 mL) was added HATU (198 mg, 0.521 mmol). The reaction was stirred at room temperature for three hours then was diluted with saturated $NaHCO_3$ and extracted with ethyl acetate (3×50 mL). The combined organic extracts were washed with water (3×20 mL), dried ($Na_2SO_4$), filtered, and concentrated in vacuo. The resulting residue was purified via column chromatography ($SiO_2$, 0-70% ethyl acetate/heptanes) to afford N-(2-(tert-Butyl)-4-(tert-butyl-$d_9$)-5-hydroxyphenyl)-4-oxo-1,4-dihydroquinoline-3-carboxamide (Compound III-d) (80 mg, 38% Yield) as a white solid. $^1$H NMR ($d_6$-DMSO, 400 MHz) δ 12.88 (s, 1H), 11.81 (s, 1H), 9.19 (s, 1H), 8.86 (s, 1H), 8.32 (dd, J=8.1, 1.4 Hz, 1H), 7.86-7.77 (m, 1H), 7.75 (d, J=8.2 Hz, 1H), 7.51 (s, 1H), 7.15 (s, 1H), 7.09 (s, 1H) 1.37 (s, 9H); MS (ESI) 402.3 [(M+H)$^+$].

Example 5: Assays for Detecting and Measuring F508del-CFTR Modulator Properties of Compounds Membrane Potential Optical Methods for Assaying Properties of F508del-CFTR Modulators An optical assay was employed to measure changes in membrane potential to determine the CFTR modulator properties of compounds. The assay utilized fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response was the creation of a chloride ion gradient in conjunction with channel activation and concurrent with compound treatment by a single liquid addition step after the cells had previously been loaded with a voltage sensing dye.

Assay Procedure

NIH3T3 mouse fibroblasts stably expressing F508del were used for optical measurements of membrane potential. The cells were maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 12,000 cells/well in 384-well matrigel-coated plates. For the correction assay, the cells were cultured at 37° C. for 18-24 hours and loaded with a voltage sensing dye. The cells were then activated and treated with Compound I. After 18-24 hours, fluorescence from the voltage sensing dye in the cells was measured to assess changes in the membrane potential as a read out for increase in functional F508del CFTR in the NIH3T3 cells.

Using this method, Compound I had an EC50 of less than 3 μM and a % Efficacy of ≥100% relative to Compound II.

Ussing Chamber Assay

Ussing chamber experiments were performed on polarized airway epithelial cells expressing F508del to further characterize the F508del modulators identified in the optical assay above. Non-CF and CF airway epithelia were isolated from bronchial tissue, cultured using methods well known in the art, and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF human bronchial epithelial (HBE) cells were isolated from non-smokers that did not have any known lung disease. CF-HBE cells were isolated from patients homozygous for F508del (F508del/F508del-HBE) or heterozygous for F508del and a mutation associated with minimal CF transmembrane conductance regulator (CFTR) function (MF) that is not expected to respond to Compound II, Compound III, Compound III-d, and the combination of Compound II and III, or Compound II and III-d (F508del/MF-HBE).

HBE cells grown on Costar® Snapwell™ cell culture inserts were mounted in an Ussing chamber (Physiologic Instruments, Inc., San Diego, Calif.), and the transepithelial resistance and short-circuit current in the presence of a basolateral to apical Cl$^-$ gradient ($I_{SC}$) were measured using a voltage-clamp system (Department of Bioengineering, University of Iowa, Iowa). Briefly, HBE cells were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$, 10 glucose, 10 HEPES (pH adjusted to 7.35 with NaOH).

Ussing Chamber Assay Procedure

A basolateral to apical membrane Cl$^-$ concentration gradient was set up as follows. Normal Ringer's solution was used on the basolateral membrane, whereas apical NaCl was replaced by equimolar sodium gluconate (titrated to pH 7.4 with NaOH) to give a large Cl$^-$ concentration gradient across the epithelium. Compound I was added either to the basolateral side 18-24 hrs prior to assay or to the apical side during the assay. Forskolin (10 μM) was added to the apical side during the assay to stimulate CFTR-mediated Cl$^-$ transport. Chloride current was measured to assess the increase in functional CFTR in the cell membrane.

Example 6: Chloride Transport Experiments

In one Ussing Chamber experiment with F508del/F508del-HBE cells, Compound I enhanced chloride transport. The effect of Compound I on chloride transport was additive to the effect of Compound II. In addition, F508del-CFTR delivered to the cell surface by either Compound I alone or in combination with Compound II was potentiated by Compound III. The triple combination of Compound I/Compound II/Compound III provided a superior (approximately 3-fold) increase in chloride transport compared to the 3 dual regimens under most conditions tested.

Example 7: F508del-CFTR Processing and Trafficking In Vitro Experiments

In vitro, Compound I improved the processing and trafficking of F508del-CFTR, thereby increasing the quantity of functional F508del-CFTR protein at the cell surface. The CFTR protein delivered to the cell surface by Compound I alone or in combination with Compound II (Compound I/Compound II) was potentiated by Compound III. In human bronchial epithelial (HBE) cells studied in vitro, the triple combination of Compound I, Compound II, and Compound III (Compound I/Compound II/Compound III) increased CFTR chloride transport more than any of the dual combinations (Compound I/Compound II, Compound I/Compound III, and Compound II/Compound III) or individual components (Compound I, Compound II, and Compound III) under most conditions studied.

Processing and trafficking of F508del-CFTR was directly monitored by the appearance of a 170 to 180 kDa band Such monitoring established that Compound I is a CFTR corrector, as it facilitates the processing and trafficking of F508del-CFTR to increase the amount of functional F508del-CFTR at the cell surface.

Incubation of F508del/F508del-HBE cells for 16 to 24 hours with 1 μM Compound I alone or in combination with 3 μM Compound II resulted in an increase in steady-state levels, reaching 6.5-fold and 18.7-fold of untreated levels, respectively.

Example 8: Safety and Efficacy Study 1 of Compound I

In healthy subjects Compound I monotherapy was shown to be safe and well tolerated at multiple doses up to 400 mg qd for 10 days.

To evaluate the safety and efficacy of Compound I in combination with Compound III and in triple combination ("TC") with Compound II and Compound III in subjects with cystic fibrosis, a randomized, double-blind, placebo- and Compound II/III-controlled, 3-part, multicenter study is conducted. Part 1 involves subjects with F508del/MF (F/MF) genotypes, Part 2 with F508del/F508del (F/F) genotype, Part 3 with F508del/gating (F/G) genotypes, Part 4 with F508del/Residual Function (RF) genotype, and Part 5 involves subjects with F508del/MF (F/MF) genotypes dosed twice daily. A F508del/gating (F/G) genotype means the patient is heterozygous for F508del with a second CFTR allele carrying a mutation conferring a gating defect clinically demonstrated to be Compound III-responsive.

Each of Parts 1-4 includes a Treatment Period and a 4-week safety follow-up period after that Treatment Period. Parts 1, 2, 3, and 4 of the study include a Treatment Period comprised of 2 dosing periods—a Compound I dosing period (Period 1) and a Compound I washout period (Period 2). Parts 3 and 4 also include a 4-week Run-in Period prior to Treatment Period 1. The patients are administered Compound II (100 mg qd/Compound III 150 mg q12h) during the Run-in-Period.

For all Parts, to be eligible to enter into the Treatment Period, after the screening pereiod, subjects have to have stable CF disease and have remained on stable CF medication regimen during the 28 days before the Day 1 Visit and must not have had an acute non-CF illness within 14 days before the Day 1 Visit.

The Compound I dosing period (Period 1) is 4 weeks. The total treatment duration (Period 1+Period 2) is approximately 5 weeks for Part 1, 8 weeks for Part 2, and 8 weeks for Parts 3 and 4.

The Treatment arms and doses by study Part, of Compound I, Compound II, and Compound III, are shown below. The following definitions apply to the dosing regimens below: "q12h" means every 12 hours; "qd" means once daily.

|  | Period 1 | | | Period 2 | |
| --- | --- | --- | --- | --- | --- |
|  | Compound I Dosage | Compound II Dosage | Compound III Dosage | Compound II Dosage | Compound III Dosage |
| Part 1 | | | | | |
| TC-high | 400 mg qd | 100 mg qd | 150 mg q12h | 100 mg qd | 150 mg q12h |
| TC-mid | 240 mg qd | 100 mg qd | 150 mg q12h | 100 mg qd | 150 mg q12h |
| TC-low | 80 mg qd | 100 mg qd | 150 mg q12h | 100 mg qd | 150 mg q12h |
| DC-high | 400 mg qd | Placebo | 150 mg q12h | Placebo | 150 mg q12h |
| Triple placebo | Placebo | Placebo | Placebo | Placebo | Placebo |
| Part 2 | | | | | |
| Cpd II/III | Placebo | 100 mg qd | 150 mg q12h | 100 mg qd | 150 mg q12h |
| TC-high | 400 mg qd | 100 mg qd | 150 mg q12h | 100 mg qd | 150 mg q12h |
| DC-high | 400 mg qd | Placebo | 150 mg q12h | 100 mg qd | 150 mg q12h |
| Part 3 | | | | | |
| Cpd II/III | Placebo | 100 mg qd | 150 mg q12h | 100 mg qd | 150 mg q12h |
| TC-high | 400 mg qd | 100 mg qd | 150 mg q12h | 100 mg qd | 150 mg q12h |
| Part 4 | | | | | |
| Cpd II/III | Placebo | 100 mg qd | 150 mg q12h | 100 mg qd | 150 mg q12h |
| TC-high | 400 mg qd | 100 mg qd | 150 mg q12h | 100 mg qd | 150 mg q12h |
| Part 5 | | | | | |
| Placebo | Placebo | Placebo | Placebo | | |
| TC-high | 160 or 240 mg q12h | 50 mg q12h | 150 mg q12h | | |

Compounds I, II, and III are administered orally within 30 minutes of the start of a fat-containing meal or snack, such as a standard "CF" meal or snack or a standard meal. A standard "CF" meal or snack includes food that contains fat, such as eggs, butter, peanut butter, cheese pizza, whole-milk dairy products (such as whole milk, cheese, and yogurt), etc.

Compound I is in the form of 80-mg tablet(s). Compound II is in the form of 50 mg tablet(s). Compound III is in the form of 150-mg tablet(s). Compound II and III can also be in the form of fixed-dose tablet(s) comprising 100-mg Compound II/150-mg Compound III.

Primary endpoints for the study include: safety and tolerability assessments based on adverse events (AEs), clinical laboratory values, standard 12-lead ECGs, vital signs, and pulse oximetry; and efficacy assessment based on absolute change in percent predicted forced expiratory volume in 1 second (ppFEV$_1$) from baseline through daily 29 Visit. Secondary endpoints include: absolute change in sweat chloride concentrations from baseline through the Day 29 Visit; relative change in ppFEV$_1$ from baseline through the Day 29 Visit; absolute change in Cystic Fibrosis Questionnaire-Revised (CFQ-R) respiratory domain score from baseline at the Day 29 Visit; and PK parameters of Compounds I, II, and III.

Results of Part 1

In the Part 1, as shown in the tables below, for 4 weeks of Compound I in triple combination with Compound II and Compound III in subjects heterozygous for F508del and a minimal function mutation (F/MF)[1] with ages 18 and older resulted in statistically significant and clinically meaningful improvements in ppFEV$_1$ (10.2-13.3 percentage points) and sweat chloride (43.7-51.4 mmol/L).

In particular, at Day 29, there was a mean absolute improvement in ppFEV$_1$ of +10.2, +11.6, and +13.3 percentage points from baseline in those respectively receiving triple combination regimens of Compound I (80 mg qd), Compound II (100 mg qd) and Compound III (150 mg, q12h); Compound I (240 mg qd), Compound II (100 mg qd) and Compound III (150 mg, q12h); and Compound I (400 mg qd), Compound II (100 mg qd) and Compound III (150 mg, q12h). For those receiving placebo, there was a mean absolute increase in ppFEV$_1$ of +0.3.

| | Placebo<br>N = 10 | Compound I<br>(80 mg, qd)/<br>Compound II<br>(100 mg, qd)/<br>Compound III<br>(150 mg, q12 h)<br>N = 11 | Compound I<br>(240 mg, qd)/<br>Compound II<br>(100 mg, qd)/<br>Compound III<br>(150 mg, q12 h)<br>N = 20 | Compound I<br>(400 mg, qd)/<br>Compound II<br>(100 mg, qd)/<br>Compound III<br>(150 mg, q12 h)<br>N = 22 |
|---|---|---|---|---|
| Baseline ppFEV1; Mean (SD) | 53.9 (12.0) | 57.9 (10.8) | 58.0 (16.8) | 59.6 (15.4) |
| Mean Absolute Within-Group Change from Baseline Through Day 29[#] (SD) | 0.3 (2.8) | 10.2 (2.7) | 11.6 (2.1) | 13.3 (1.9) |
| p-value (within-treatment)[#] | 0.9053 | 0.0004 | <0.0001 | <0.0001 |

[#]All p-values are within group p-values based on mixed effect models; values expressed as 'Through Day 29' are the average of Day 15 and Day 29 measures.

At Day 29, there was a mean decrease in sweat chloride of −45.8, −437, and −51.4 mmol/L from baseline in those respectively receiving triple combination regimens of Compound I (80 mg qd), Compound II (100 mg qd) and Compound III (150 mg, q12h); Compound I (240 mg qd), Compound II (100 mg qd) and Compound III (150 mg, q12h); and Compound I (400 mg qd), Compound II (100 mg qd) and Compound III (150 mg, q12h). For those receiving placebo, there was a mean absolute increase in sweat chloride of 2.9.

| | Placebo<br>N = 10 | Compound I<br>(80 mg, qd)/<br>Compound II<br>(100 mg, qd)/<br>Compound III<br>(150 mg q12 h)<br>N = 11 | Compound I<br>(240 mg, qd)/<br>Compound II<br>(100 mg, qd)/<br>Compound III<br>(150 mg, q12 h)<br>N = 20 | Compound I<br>(400 mg, qd)/<br>Compound II<br>(100 mg, qd)/<br>Compound III<br>(150 mg, q12 h)<br>N = 22 |
|---|---|---|---|---|
| Baseline SwCl; Mean (SD) | 98.2 (13.3) | 102.7 (7.0) | 100.5 (9.0) | 100.7 (11.6) |
| Mean Absolute Within-Group Change from Baseline Through Day 29[#] (SD) | 2.9 (4.6) | −45.8 (4.4) | −43.7 (3.5) | −51.4 (3.2) |

-continued

|  | Placebo<br>N = 10 | Compound I<br>(80 mg, qd)/<br>Compound II<br>(100 mg, qd)/<br>Compound III<br>(150 mg q12 h)<br>N = 11 | Compound I<br>(240 mg, qd)/<br>Compound II<br>(100 mg, qd)/<br>Compound III<br>(150 mg, q12 h)<br>N = 20 | Compound I<br>(400 mg, qd)/<br>Compound II<br>(100 mg, qd)/<br>Compound III<br>(150 mg, q12 h)<br>N = 22 |
|---|---|---|---|---|
| p-value (within-treatment)# | 0.5338 | <0.0001 | <0.0001 | <0.0001 |

All p-values are within group p-values based on mixed effect models; values expressed as 'Through Day 29' are the average of Day 15 and Day 29 measures.

A secondary endpoint in the triple combination study Part 1 measured mean absolute change in the respiratory domain of CFQ-R validated patient-reported outcome measure, at Day 29. The mean absolute improvements for patients who received the triple combination were 24.6 points (80 mg Compound 1), 19.8 points (240 mg Compound I) and 21.8 points (400 mg Compound I). The improvement for those who received placebo was 4.7 points. The CFQ-R results reported are based on a mixed effect models not adjusted for baseline CFQR.

An overview of treatment emergent adverse events ("TEAB") after 29 days is provided below.

ages 18 and older resulted in statistically significant and clinically meaningful improvements in ppFEV$_1$ (9.7 percentage points) and sweat chloride (42.2 mmol/L).

In particular, at Day 29, there was a mean absolute improvement in ppFEV$_1$ of +9.7 percentage points from baseline in those receiving triple combination regimens of Compound I (400 mg qd), Compound II (100 mg qd) and Compound III (150 mg, q12h). For those receiving placebo along with Compound II (100 mg qd) and Compound III (150 mg, q12h), there was a mean absolute increase in ppFEV$_1$ of 0.0.

|  | Placebo<br>N = 10 | Compound I<br>(80 mg, qd)/<br>Compound II<br>(100 mg, qd)/<br>Compound III<br>(150 mg, q12 h)<br>N = 11 | Compound I<br>(240 mg, qd)/<br>Compound II<br>(100 mg, qd)/<br>Compound III<br>(150 mg, q12 h)<br>N = 20 | Compound I<br>(400 mg, qd)/<br>Compound II<br>(100 mg, qd)/<br>Compound III<br>(150 mg, q12 h)<br>N = 22 | Compound I<br>Triple<br>Combination<br>Total<br>N = 53 |
|---|---|---|---|---|---|
| Subjects with any TEAE | 9 (90.0) | 9 (81.8) | 14 (70.0) | 17(77.3) | 40 (75.5) |
| Subjects with Severe TEAE | 0 | 0 | 1 | 1 | 2 |
| Subjects with Serious TEAE | 3 | 1 | 3 | 0 | 4 |
| Subjects with TEAE leading to treatment discontinuation | 0 | 0 | 0 | 0 | 0 |
| Subjects with TEAE leading to drug interruption | 0 | 0 | 1 | 0 | 1 |

In summary, in Part 1 of the study, the triple combination regimen was generally well tolerated. The majority of adverse events were mild or moderate. Serious adverse events were reported in seven patients: three patients in the placebo group (2 with infective pulmonary exacerbations and 1 with decreased pulmonary function test) and four in the triple combination groups (3 with infective pulmonary exacerbations and 1 with influenza), None of these serious adverse events were considered related to treatment and none resulted in treatment discontinuation. The most common adverse events (>10%), regardless of treatment group, were cough, headache, oropharyngeal (throat) pain and sputum increased. There were no discontinuations due to adverse events. One patient interrupted treatment due to an adverse event in the triple combination treatment groups (rash). The rash resolved upon interrupting treatment and this patient subsequently restarted and completed triple combination treatment without any further rash.

Results of Part 2

In Part 2, as shown in the tables below, 4 weeks of Compound I in triple combination with Compound II and Compound III in subjects homozygous for F508del with

|  | Placebo/<br>Compound II<br>(100 mg, qd)/<br>Compound III<br>(150 mg, q12 h)<br>N = 11 | Compound I<br>(400 mg, qd)/<br>Compound II<br>(100 mg, qd)/<br>Compound III<br>(150 mg, q12 h)<br>N = 48 |
|---|---|---|
| Baseline ppFEV1; Mean (SD) | 60.0 (12.6) | 58.6 (13.3) |
| Mean Absolute Within-Group Change from Baseline Through Day 29# (SE) | 0.0 (1.9) | 9.7 (1.5) |
| p-value (within-treatment)# | 0.9926 | <0.0001 |

All p-values are within group p-values based on mixed effect models; values expressed as 'Through Day 29' are the average of Day 15 and Day 29 measures.

At Day 29, there was a mean decrease in sweat chloride of −42.2 mmol/L from baseline in those receiving triple combination regimens of Compound 1 (400 mg qd), Compound II (100 mg qd) and Compound III (150 mg, q12h).

For those receiving placebo along with Compound II (100 mg qd) and Compound III (150 mg, q12h), there was a mean absolute increase in sweat chloride of +3.0.

|   | Placebo/<br>Compound II<br>(100 mg, qd)/<br>Compound III<br>(150 mg, q12 h)<br>N = 41 | Compound I<br>(400 mg, qd)/<br>Compound II<br>(100 mg, qd)/<br>Compound III<br>(150 mg, q12 h)<br>N = 18 |
|---|---|---|
| Baseline SwCl; Mean (SB) | 96.6 (11.4) | 91.9 (11.6) |
| Mean Absolute Within-Group Change from Baseline Through Day 29[#] (SE) | 3.0 (2.8) | −42.2 (2.2) |
| p-value (within-treatment)[#] | 0.2977 | <0.0001 |

[#]All p-values are within group p-values based on mixed effect models; values expressed as 'Through Day 29' are the average of Day 15 and Day 29 measures.

A secondary endpoint in the triple combination study Part 2 measured mean absolute change in the respiratory domain of CFQ-R validated patient-reported outcome measure, at Day 29. The mean absolute improvement for patients who received the triple combination was 20.1 points. The improvement for those who received placebo rather than Compound I was 2.0 points. The CFQ-R results reported are based on a mixed effect models not adjusted for baseline CFQR.

An overview of treatment emergent adverse events ("TEAS") after 29 days is provided below.

|   | Placebo/<br>Compound II<br>(100 mg, qd)/<br>Compound III<br>(150 mg, q12 h)<br>N = 11 | Compound I<br>(400 mg, qd)/<br>Compound II<br>(100 mg, qd)/<br>Compound III<br>(150 mg, q12 h)<br>N = 18 |
|---|---|---|
| Subjects with any TEAE | 8 (72.7) | 14 (77.8) |
| Subjects with Severe TEAE |  |  |
| Subjects with Serious TEAE | 1[a] | 0 |
| Subjects with TEAE leading to treatment discontinuation | 0 | 0 |
| Subjects with TEAE leading to drug interruption | 0 | 0 |

[a]PEx
[b] Abdominal pain
[c] Elevated AST/CK

In summary, in Part 2 of the study, the triple combination regimen was generally well tolerated. There were no serious adverse events in the triple combination arm, and all adverse events in the triple combination arm were mild or moderate. There were no treatment discontinuations or interruptions. The most common adverse events (>10%), regardless of treatment group, were cough, infective pulmonary exacerbation, nasal congestion, nausea, sputum increased, vomiting and headache.

Example 9: Safety and Efficacy Study 2 of Compound 1

To evaluate the safety and efficacy of Compound I in triple combination ("TC") with Compound II and Compound III-d in subjects with cystic fibrosis, a randomized, double-blind, triple placebo-controlled study was conducted with subjects with F508del/MF (F/MF) genotypes (e.g., heterozygous for F508del with a second CFTR allele carrying a MF mutation described in Table C).

The Treatment arm and doses of Compound. I, Compound H, and Compound III-d are shown below. The following definitions apply to the dosing regimens below: "q12h" means every 12 hours; "qd" means once daily.

|   | Treatment Period | | |
|---|---|---|---|
|   | Compound I | Compound II | Compound III-d |
| TC2-high | 400 mg qd | 100 mg qd | 200 mg qd |
| Triple placebo | Placebo | Placebo | Placebo |

Primary endpoints for the study include: safety and tolerability assessments based on adverse events (AEs), clinical laboratory values, standard 12-lead ECGs, vital signs, and pulse oximetry; and efficacy assessment based on absolute change in percent predicted forced expiratory volume in 1 second (ppFEV$_1$) from baseline through daily 29 Visit. Secondary endpoints include: absolute change in sweat chloride concentrations from baseline through the Day 29 Visit; relative change in ppFEV$_1$ from baseline through the Day 29 Visit; absolute change in Cystic Fibrosis Questionnaire-Revised (CFQ-R) respiratory domain score from baseline at the Day 29 Visit; and PK parameters of Compounds I, II, and III-d.

Results

As shown in the table below, for 4 weeks of Compound I in triple combination with Compound II and Compound III-d in subjects heterozygous for F508del and a minimal function mutation (F/MF) with ages 18 and older resulted in statistically significant and clinically meaningful improvements in ppFEV$_1$ (12.2 percentage points) and sweat chloride (38.1 mmol/L).

In particular, at Day 29, there was a mean absolute improvement in ppFEV$_1$ of +12.2 percentage points from baseline in those receiving triple combination regimens of Compound I (400 mg qd), Compound II (100 mg qd) and Compound III-d (200 tug, qd). For those receiving triple placebo, there was a mean absolute change in ppFEV$_1$ of −5.0. For those in the Part 1, "TC-high" arm discussed above, who received triple combination regimens of Compound I (400 mg qd), Compound II (100 mg qd) and Compound III (150 mg, q12h), there was a mean absolute change in ppFEV$_1$ of +13.3.

|   | Triple<br>Placebo<br>N = 6 | Compound I<br>(400 mg, qd)/<br>Compound II<br>(100 mg, qd)/<br>Compound III-d<br>(200 mg, qd)<br>N = 19 | PART D, TC-high -<br>Compound I<br>(400 mg, qd)/<br>Compound II<br>(100 mg, qd)/<br>Compound III<br>(150 mg, q12 h)<br>N = 22 |
|---|---|---|---|
| Baseline ppFEV1; Mean (SD) | 53.0 (12.3) | 59.8 (12.6) | 59.6 (15.4) |

|  | Triple Placebo N = 6 | Compound I (400 mg, qd)/ Compound II (100 mg, qd)/ Compound III-d (200 mg, qd) N = 19 | PART D, TC-high - Compound I (400 mg, qd)/ Compound II (100 mg, qd)/ Compound III (150 mg, q12 h) N = 22 |
|---|---|---|---|
| Mean Absolute Within-Group Change from Baseline Through Day 29[#] (SE) | −5.0 (3.4) | 12.2 (1.9) | 13.3 (1.9) |
| p-value (within-treatment)[#] | 0.1561 | <0.0001 | <0.0001 |

[#]All p-values are within group p-values based on mixed effect models; values expressed as 'Through Day 29' are the average of Day 15 and Day 29 measures.

At Day 29, there was a mean decrease in sweat chloride of −33.6 mmol/L from baseline in those receiving triple combination regimens of Compound I (200 mg qd), Compound II (100 mg qd) and Compound III-d (150 mg, qd). For those receiving triple placebo, there was a mean absolute decrease in sweat chloride of −2.2. For those in Part D, TC-high who received triple combination regimens of Compound I (200 mg qd), Compound II (100 mg qd) and Compound III (150 mg, q12h), there was a mean absolute decrease in sweat chloride of −39.1.

|  | Triple Placebo N = 6 | Compound I (400 mg, qd)/ Compound II (100 mg, qd)/ Compound III-d (200 mg, qd) N = 19 | PART D, TC-high - Compound I (400 mg, qd)/ Compound II (100 mg, qd)/ Compound III (150 mg, q12 h) N = 22 |
|---|---|---|---|
| Baseline SwCl; Mean (SD) | 96.6 (4.3) | 101.2 (9.5) | 100.7 (11.6) |
| Mean Absolute Within-Group Change from Baseline Through Day 29[#] (SD) | −13 (5.3) | −38.1 (3.0) | −51.4 (3.2) |
| p-value (within-treatment)[#] | 0.8077 | <0.0001 | <0.0001 |

[#]All p-values are within group p-values based on mixed effect models; values expressed as 'Through Day 29' are the average of Day 15 and Day 29 measures.

A secondary endpoint in the triple combination measured mean absolute change in the respiratory domain of CFQ-Rat Day 29, The mean absolute improvement for patients who received the triple combination with Compound III-d was 14.7 points. The improvement for those who received triple placebo was −4.1 points. The improvement for those in Part 1, TC-high who received triple combination with Compound III was 21.0 points. The CFQ-R results reported are based on a mixed effect models not adjusted for baseline CFQR.

An overview of treatment ergent adverse events ("TEAE") after 29 days is provided below.

|  | Triple Placebo N = 6 | Compound I (400 mg, qd)/ Compound II (100 mg, qd)/ Compound III-d (200 mg, qd) N = 19 | PART D, TC-high - Compound I (400 mg, qd)/ Compound II (100 mg, qd)/ Compound III (150 mg, q12 h) N = 22 |
|---|---|---|---|
| Subjects with any TEAE | 6 (100.0) | 15 (78.9) | 17 (77.3) |
| Subjects with Severe TEAE | 1 | 3[a, b, c] | 1[$] |

-continued

|  | Triple Placebo N = 6 | Compound I (400 mg, qd)/ Compound II (100 mg, qd)/ Compound III-d (200 mg, qd) N = 19 | PART D, TC-high - Compound I (400 mg, qd)/ Compound II (100 mg, qd)/ Compound III (150 mg, q12 h) N = 22 |
|---|---|---|---|
| Subjects with Serious TEAE | 3 | 7[c, d] | 0 |
| Subjects with TEAE leading to treatment discontinuation | 0 | 1[b] | 0 |
| Subjects with TEAE leading to drug interruption | 0 | 2[a, b] | 0 |

[a]Laceration; and same subject had rash ted to interruption
[b]Vertigo, Vomiting; and the same subject had rash led to interruption, later discontinued due to drug hypersensitivity (eye swelling)
[c]Pyrexia, Dyspnoea and Pleuritic pain
[d]PEx and Pneumonia
[$]Pyrexia/Oropharyngeal pain/Foot fracture In summary, the triple combination regimen was generally well tolerated. The majority of adverse events were mild or moderate. There were 2 dose interruptions—both due to rash, There was I treatment discontinuation due to drug hypersensitivity in one of the subjects who had interrupted dose due to rash. A total of 2 subjects treated with the triple combination including Compound III-d had serious AEs, all of which occurred after the triple combination treatment period.

Example 10: Safety and Efficacy Study 3 of Compound I

The safety and tolerability of single and multiple ascending doses 10 mg-240 mg of Compound. I alone and in triple combination with Compound II and Compound III (Compound II 100 mg qd/Compound III 150 mg $q_{12}$h) in healthy volunteers were evaluated in a randomized, double-blind, placebo-controlled study.

It also evaluated the safety and tolerability of Compound I as part of a triple combination for two weeks in people with CF ages 18 and older who have one F508del mutation and one minimal function mutation (3 in placebo and 9 in Compound I 120 mg q12q). In this part of the study, sweat chloride was evaluated as an additional endpoint, and the absolute change in ppFEV$_1$ was evaluated as part of the safety analysis.

| Screening 4 weeks | Treatment Period 2 weeks | Safety Follow-up 3-5 weeks |
|---|---|---|
| N = 9 | Compound I + Compound II + Compound III | |
| N = 3 | Triple Placebo | |

Compound I 120 mg q12 h/Compound II 50 mg q12 h/Compound III 150 mg q12 h

At Day 15, there was a mean absolute improvement in ppFEV$_1$ of +9.6 percentage points from baseline in those receiving the triple combination regimen of Compound I (120 mg q12h), Compound II and Compound III, and a mean decrease in sweat chloride of −41.6 mmol/L. For those receiving placebo, there was a mean absolute decrease in ppFEV$_1$ of −0.4 and a mean decrease in sweat chloride of −11.0.

|  | Placebo N = 3 | Compound I/ Compound II/ Compound III N = 9* |
|---|---|---|
| Baseline ppFEV1; Mean (SD) | 44.9 (9.6) | 48.0 (12.7) |
| Mean Change at Day 15 (SD) | −0.4 (1.0) | 9.6 (10.0) |
| D-value (within-treatment)[#] | 0.5398 | 0.0304 |

[#]one-sample t-test
*N = 8 for triple combo at Day 15

|  | Placebo N = 3 | Compound I/ Compound II/ Compound III N = 9* |
|---|---|---|
| Baseline Sweat Chloride; Mean (SD) | 104.3 (4.9) | 107.7 (10.5) |
| Mean Change at Day 15 (SD) | −11.0 (12.5) | −41.6 (10.3) |
| p-value (within-treatment)[#] | 0.2667 | <0.0001 |

[#]one-sample t-test
*N = 8 for triple combo at Day 15

An overview of treatment emergent adverse events ("TEAE") after 15 days is provided below.

|  | Placebo N = 3 n(%) | Compound I/ Compound II/ Compound III N = 9 n(%) |
|---|---|---|
| Subjects with any TEAE | 0 | 8 (88.9) |
| Subjects with Severe TEAE | 0 | 0 |
| Subjects with Serious TEAE | 0 | 2 (22.2) |
| Subjects with TEAE leading to treatment discontinuation | 0 | 0 |
| Subjects with TEAE leading to drug interruption | 0 | 0 |

Example 11: Safety and Efficacy Study 3 of Compound I

In Study 3A, the following TC and DC arms will be studied in 100 subjects ages 12 and older with cystic fibrosis who are homozygous for the F508del mutation (F/F). The total study duration is approximately 16 weeks (4 weeks for screening, followed by 4 weeks for the Compound II/Compound III Run-in Period, followed by 4 weeks for the Treatment Period, which is followed by 4 weeks for the safety follow-up period). In the Compound II/Compound III Run-in Period, all subjects will receive Compound II 100 mg once daily (qd)/Compound III 150 mg every 12 hours (q12h). After completing the Compound II/Compound III Run-in Period, subjects will be randomized to the TC arm or placebo/DC arm (approximately 50 patients in each arm) for the Treatment Period. The Treatment arms and doses to be evaluated are shown in the table below.

| Treatment Arm | Compound II/Compound III Run-in period | | | Treatment Arm | Treatment Period | | |
|---|---|---|---|---|---|---|---|
| | Compound I Dose | Compound II Dose | Compound III Dose | | Compound I Dose | Compound II Dose | Compound III Dose |
| Triple Combo (TC) | 0 mg | 100 mg qd | 150 mg q12 h | Triple Combo (TC) | 240 mg qd | 100 mg qd | 150 mg q12 h |
| Compound II/Compound III (DC) | 0 mg | 100 mg qd | 150 mg q12 h | Compound II/Compound III | 0 mg | 100 mg qd | 150 mg q12 h |

The primary endpoint of the study is the mean absolute change in lung function (ppFEV$_1$) from baseline at week four of triple combination treatment compared to those who received placebo, tezacaftor and ivacaftor. Secondary endpoints will also be measured at week four and include changes in patient-reported outcomes as measured by the respiratory domain of the Cystic Fibrosis Questionnaire-Revised (CFQ-R) and change in sweat chloride, among others.

In Study 3B, the following TC and DC arms will be studied in subjects with cystic fibrosis (CF) who are heterozygous for the F508del mutation and an MF mutation (F/MF subjects). The total study duration is approximately 32 weeks (4 weeks for the screening period, followed by 24 weeks for the Treatment Period, which is followed by 4 weeks for the safety follow-up period). Unlike in Study 3A, there is no Run-in Period in Study 3B. Subjects will be randomized to the TC arm or triple placebo arm. The doses to be evaluated are shown in the table below.

| Treatment Arms and Doses | | | |
|---|---|---|---|
| Treatment Arm | Compound I Dose | Compound II Dose | Compound III Dose |
| TC | 240 mg qd | 100 mg qd | 150 mg q12 h |
| Triple placebo | 0 mg | 0 mg | 0 mg | q12 h: every 12 hours;
qd: once daily;
TC: triple combination

Example 12: Safety and Efficacy Study 4 of Compound I

To evaluate the long-term safety and efficacy of Compound I, in Study 4, patients who complete the Treatment Period in Study 3A or 3B will receive the TC at the same doses evaluated in Study 3A or 3B. The total study duration is approximately 100 weeks (including a 96-week Treatment Period (not including the 4 weeks for Study 3A or 3B) followed by a 4 week safety follow-up period).

Example 13: Preclinical Toxicology Data

Preclinical reproductive toxicology studies of Compound I showed no adverse findings of note.

OTHER EMBODIMENTS

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A method of treating cystic fibrosis comprising administering daily to a patient in need thereof:
   (A) 80 mg to 400 mg of at least one compound chosen from Compound I:

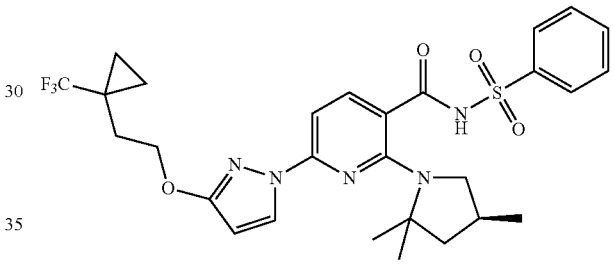

and pharmaceutically acceptable salts thereof; and
   (B) at least one compound chosen from:
      (i) Compound II:

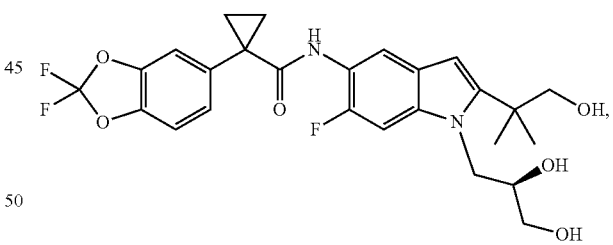

and pharmaceutically acceptable salts thereof,
      (ii) Compound III:

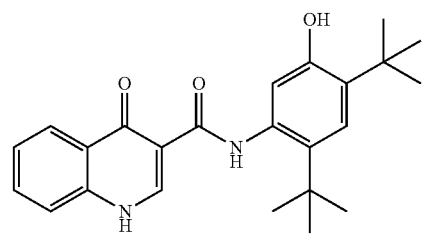 [SMILES: CC(C)(C)c1cc(C(C)(C)C)c(NC(=O)c2c[nH]c3ccccc3c2=O)cc1O]

and pharmaceutically acceptable salts thereof, or Compound III-d:

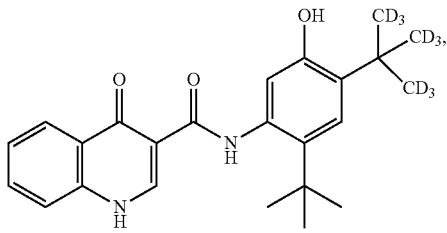 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

and pharmaceutically acceptable salts thereof, and (iii) Compound IV:

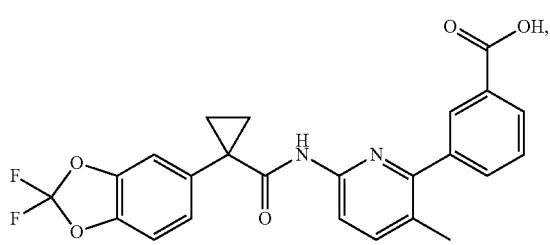 [SMILES: Cc1ccc(NC(=O)C2(c3ccc4c(c3)OC(F)(F)O4)CC2)nc1-c1cccc(C(=O)O)c1]

and pharmaceutically acceptable salts thereof.

2. The method according to claim 1, comprising administering to said patient:

(A) at least one compound chosen from Compound I and pharmaceutically acceptable salts thereof; and at least one compound chosen from Compound II and pharmaceutically acceptable salts thereof;

(B) at least one compound chosen from Compound I and pharmaceutically acceptable salts thereof; and at least one compound chosen from (i) Compound III and pharmaceutically acceptable salts thereof, or (ii) Compound III-d and pharmaceutically acceptable salts thereof; or (C) at least one compound chosen from Compound I and a pharmaceutically acceptable salts thereof; and at least one compound chosen from Compound IV and pharmaceutically acceptable salts thereof.

3. The method according to claim 1, comprising administering to said patient:

(A) at least one compound chosen from Compound I and pharmaceutically acceptable salts thereof;

(B) at least one compound chosen from (i) Compound III and pharmaceutically acceptable salts thereof, or (ii) Compound III-d and pharmaceutically acceptable salts thereof; and (C) at least one compound chosen from Compound IV and pharmaceutically acceptable salts thereof.

4. The method of according to claim 1, comprising administering to said patient:

(A) at least one compound chosen from Compound I and pharmaceutically acceptable salts thereof;

(B) at least one compound chosen from Compound II and pharmaceutically acceptable salts thereof; and (C) at least one compound chosen from Compound III and pharmaceutically acceptable salts thereof.

5. The method of according to claim 1, comprising administering to said patient:

(A) at least one compound chosen from Compound I and pharmaceutically acceptable salts thereof;

(B) at least one compound chosen from Compound II and pharmaceutically acceptable salts thereof; and (C) at least one compound chosen from Compound III-d and pharmaceutically acceptable salts thereof.

6. The method according to claim 1, wherein 120 mg to 240 mg of Compound I or a pharmaceutically acceptable salt thereof is administered daily.

7. The method according to claim 1, wherein 120 mg to 360 mg of Compound I or a pharmaceutically acceptable salt thereof is administered daily.

8. The method according to claim 1, wherein 120 mg of Compound I or a pharmaceutically acceptable salt thereof is administered daily.

9. The method according to claim 1, wherein 240 mg of Compound I or a pharmaceutically acceptable salt thereof is administered daily.

10. The method according to claim 1 wherein 120 mg of Compound I or a pharmaceutically acceptable salt thereof per dosing is administered twice daily.

11. The method according to claim 1, wherein 50 mg to 150 mg of Compound II or a pharmaceutically acceptable salt thereof is administered daily.

12. The method according to claim 1, wherein 100 mg of Compound II or a pharmaceutically acceptable salt thereof is administered daily.

13. The method according to claim 1, wherein:

(i) 50 mg to 600 mg of Compound III or a pharmaceutically acceptable salt thereof is administered daily; or (ii) 50 mg to 600 mg of Compound III-d or a pharmaceutically acceptable salt thereof is administered daily.

14. The method according to claim 1, wherein: (i) 125 mg to 300 mg of Compound III or a pharmaceutically acceptable salt thereof is administered daily; or (ii) 125 mg to 300 mg of Compound III-d or a pharmaceutically acceptable salt thereof is administered daily.

15. The method according to claim 1, wherein: (i) 75 mg of Compound III or a pharmaceutically acceptable salt thereof per dosing is administered twice daily; or (ii) 100 mg of Compound III-d or a pharmaceutically acceptable salt thereof is administered per dosing once daily.

16. The method according to claim 1, wherein 400 mg to 1,000 mg of Compound IV or a pharmaceutically acceptable salt thereof is administered daily.

17. The method according to claim 1, wherein:

(A) 50 mg to 200 mg of at least one compound chosen from Compound II and pharmaceutically acceptable salts thereof is administered daily and/or 150 mg to 600 mg of at least one compound chosen from Compound III and pharmaceutically acceptable salts thereof is administered daily; or (B) 50 mg to 200 mg of at least one compound chosen from Compound II and pharmaceutically acceptable salts thereof is administered daily and/or 100 mg to 400 mg of at least one compound chosen from Compound III-d and pharmaceutically acceptable salts thereof is administered daily.

18. The method according to claim 1, wherein the at least one compound chosen from Compound I and pharmaceutically acceptable salts thereof is Compound I.

19. The method according to claim 1, wherein the at least one compound chosen from Compound I and pharmaceutically acceptable salts thereof is a pharmaceutically acceptable salt of Compound I.

20. A method of treating cystic fibrosis comprising administering daily to a patient in need thereof:

(A) 50 mg to 300 mg of Compound I:

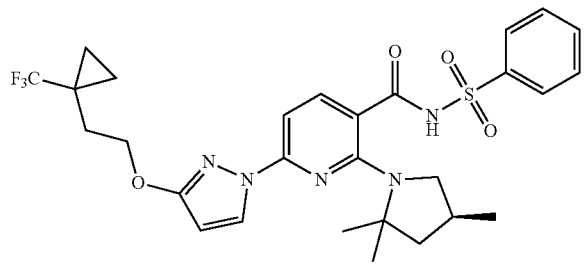 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

or a pharmaceutically acceptable salt thereof daily; 50 mg of Compound II:

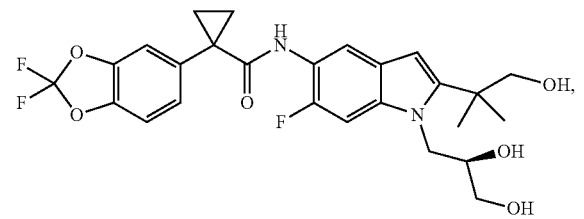 [SMILES: CC(C)(CO)c1cc2cc(NC(=O)C3(c4ccc5c(c4)OC(F)(F)O5)CC3)c(F)cc2n1C[C@@H](O)CO]

or a pharmaceutically acceptable salt thereof; and 150 mg or 300 mg of Compound III:

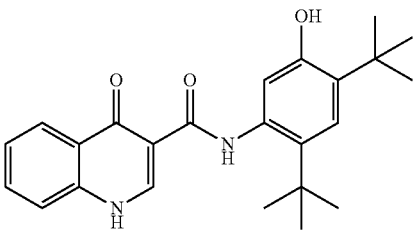 [SMILES: CC(C)(C)c1cc(C(C)(C)C)c(NC(=O)c2c[nH]c3ccccc3c2=O)cc1O]

or a pharmaceutically acceptable salt thereof; or (B) 50 mg to 300 mg of Compound I or a pharmaceutically acceptable salt thereof; 50 mg of Compound II or a pharmaceutically acceptable salt thereof; and 150 mg, 200 mg, or 300 mg of Compound III-d:

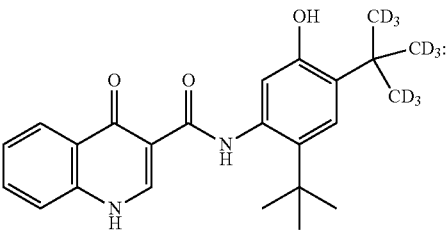

or a pharmaceutically acceptable salt thereof.

21. The method according to claim 20, wherein:

(A) 120 mg of Compound I or a pharmaceutically acceptable salt thereof; 50 mg of Compound II or a pharmaceutically acceptable salt thereof; and 150 mg of Compound III or a pharmaceutically acceptable salt thereof are administered daily; or (B) 120 mg of Compound I or a pharmaceutically salt thereof; 50 mg of Compound II or a pharmaceutically acceptable salt thereof; and 100 mg of Compound III-d or a pharmaceutically acceptable salt thereof are administered once daily.

* * * * *